United States Patent
Dück

(10) Patent No.: US 11,873,293 B2
(45) Date of Patent: Jan. 16, 2024

(54) ORGANIC MOLECULES FOR OPTOELECTRONIC DEVICES

(71) Applicant: Samsung Display Co., Ltd., Yongin-si (KR)

(72) Inventor: Sebastian Dück, Heidelberg (DE)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/811,668

(22) Filed: Jul. 11, 2022

(65) Prior Publication Data

US 2022/0380351 A1    Dec. 1, 2022

Related U.S. Application Data

(63) Continuation of application No. 16/737,046, filed on Jan. 8, 2020, now Pat. No. 11,384,070.

(30) Foreign Application Priority Data

Jan. 10, 2019 (EP) ..................... 19151254

(51) Int. Cl.
C07D 403/14    (2006.01)
H10K 71/16    (2023.01)
H10K 85/60    (2023.01)

(52) U.S. Cl.
CPC ......... *C07D 403/14* (2013.01); *H10K 71/164* (2023.02); *H10K 85/654* (2023.02); *H10K 85/6572* (2023.02)

(58) Field of Classification Search
None
See application file for complete search history.

(56) References Cited

U.S. PATENT DOCUMENTS

2015/0041784 A1*  2/2015  Shizu ............... C09K 11/06
                                                        544/102
2017/0186962 A1   6/2017  Ren et al.

FOREIGN PATENT DOCUMENTS

EP    3421461 A1    1/2019
JP    2016-033115 A  3/2016

* cited by examiner

*Primary Examiner* — Gregory D Clark
(74) *Attorney, Agent, or Firm* — Lewis Roca Rothgerber Christie LLP

(57) ABSTRACT

An organic molecule for use in optoelectronic devices having a structure of formula I Formula I

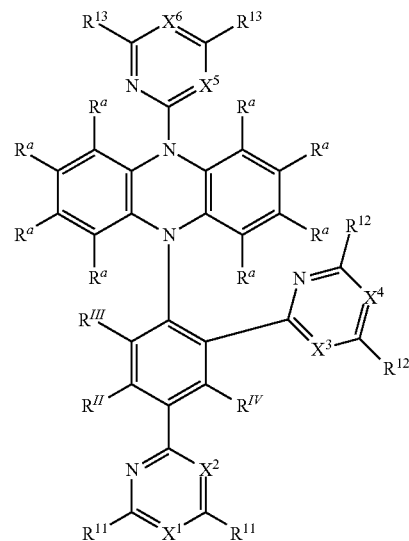

wherein
$X^1$ and $X^2$ are at each occurrence independently selected from the group consisting of $CR^{21}$ and N;
$X^3$ and $X^4$ are at each occurrence independently selected from the group consisting of $CR^{22}$ and N:
$X^5$ and $X^6$ are at each occurrence independently selected from the group consisting of $CR^{23}$ and N;
$R^{21}$, $R^{22}$, $R^{23}$ is at each occurrence independently selected from the group consisting of hydrogen, deuterium, $C_1$-$C_5$-alkyl, $C_2$-$C_8$-alkenyl, $C_2$-$C_8$-alkynyl, $C_6$-$C_{18}$-aryl, and $C_3$-$C_{17}$-heteroaryl; and (Continued)

at least one variable of $X^1$ and $X^2$ is N, at least one variable of $X^3$ and $X^4$ is N and at least one variable of $X^5$ and $X^6$ is N.

18 Claims, 1 Drawing Sheet

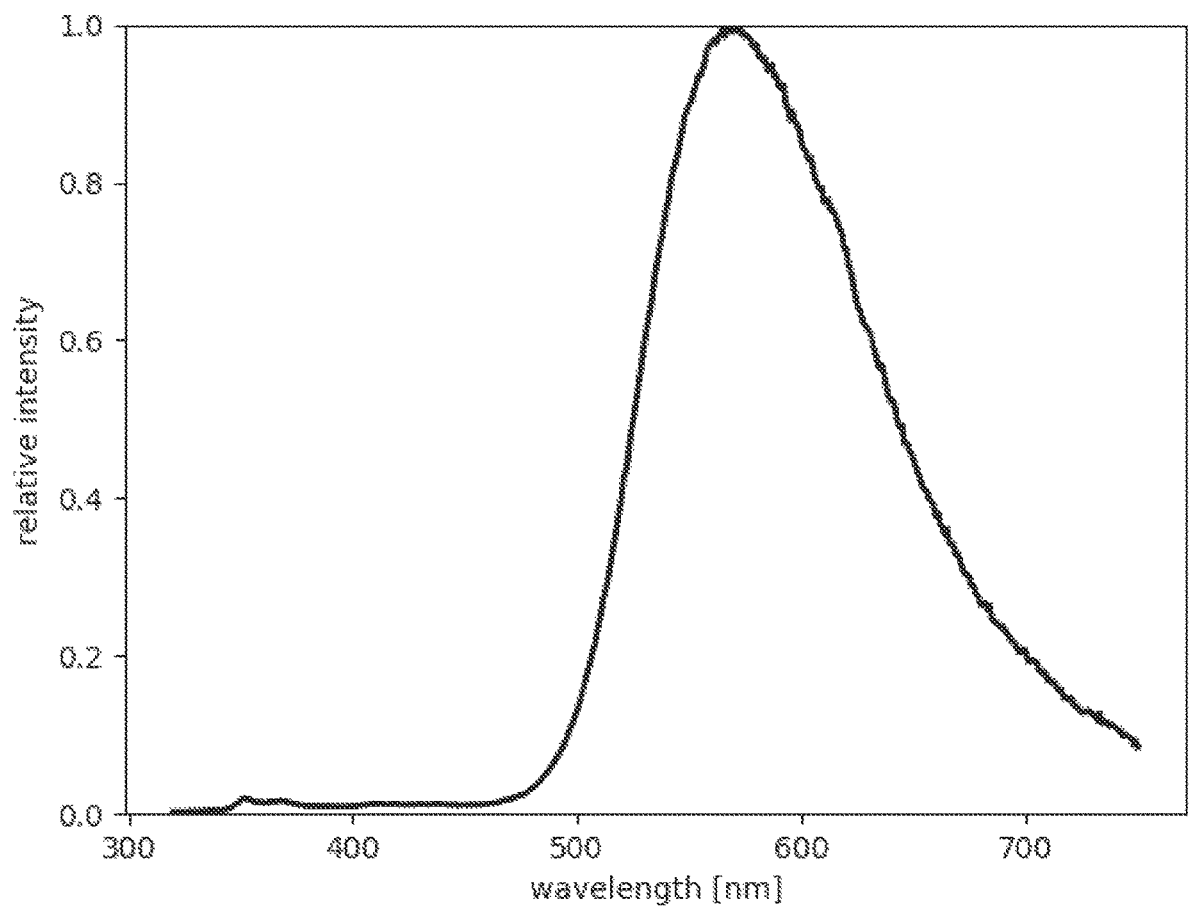

ORGANIC MOLECULES FOR OPTOELECTRONIC DEVICES

CROSS-REFERENCE TO RELATED APPLICATIONS

This application is a continuation of U.S. patent application Ser. No. 16/737,046, filed Jan. 8, 2020, which priority to and the benefit of European Patent Application No. 19151254.0, filed Jan. 10, 2019, the disclosures of all of which are incorporated by reference herein in their entirety.

FIELD OF THE INVENTION

The invention relates to organic molecules and their use in organic light-emitting diodes (OLEDs) and in other optoelectronic devices.

BRIEF DESCRIPTION OF THE DRAWINGS

Exemplary embodiments of the present invention will be described below in more detail, with reference to the accompanying drawings, of which:

FIG. 1 shows the emission spectrum of Example 1 (10% by weight) in 3,3-di(9H-carbazol-9-yl)biphenyl (mCBP).

DETAILED DESCRIPTION OF EXEMPLARY EMBODIMENTS OF THE INVENTION

Exemplary embodiments of the invention will now be discussed in further detail. This invention may, however, be embodied in many different forms and should not be construed as limited to the embodiments set forth herein.

The object of the present invention is to provide molecules which are suitable for use in optoelectronic devices.

This object is achieved by the invention which provides a new class of organic molecules.

The organic molecules of the invention are preferably purely organic molecules, i.e. they do not contain any metal ions, which is in contrast to metal complexes known for the use in optoelectronic devices. Therefore, according to the present invention, it is preferred that the organic molecules are free of metal atoms or metal ions. The pure organic molecules may, however, include metalloids, in particular, B, Si, Sn, Se, and/or Ge.

According to the present invention, the organic molecules exhibit emission maxima in the sky blue, green or yellow spectral range. The photoluminescence quantum yields of the organic molecules according to the invention are, in particular, 50% or more. The molecules of the invention exhibit in particular thermally activated delayed fluorescence (TADF). The use of the molecules according to the invention in an optoelectronic device, for example, an organic light-emitting diode (OLED), leads to higher efficiencies of the device. Corresponding OLEDs have a higher stability than OLEDs with known emitter materials and comparable color and/or by employing the molecules according to the invention in an OLED display, a more accurate reproduction of visible colors in nature, i.e. a higher resolution in the displayed image, is achieved. In particular, the molecules can be used in combination with a fluorescence emitter to enable so-called hyper-fluorescence.

The light-emitting organic molecules according to the invention comprise or consist of a structure of formula I,

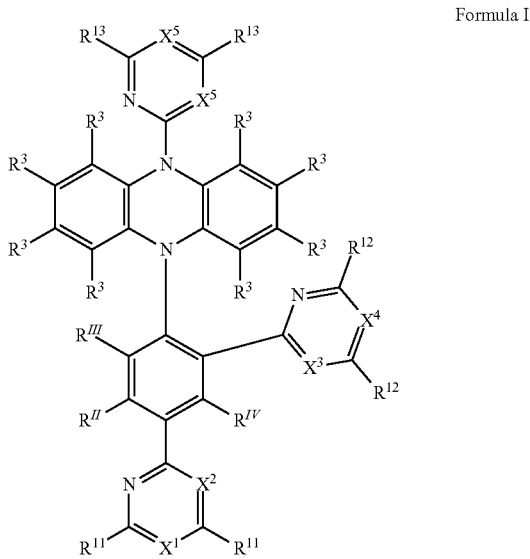

Formula I

In that formula:

$X^1$ and $X^2$ is at each occurrence independently from another selected from the group consisting of $CR^{21}$ and N.

$X^3$ and $X^4$ is at each occurrence independently from another selected from the group consisting of $CR^{22}$ and N.

$X^5$ and $X^6$ is at each occurrence independently from another selected from the group consisting of $CR^{23}$ and N.

$R^{11}$ is at each occurrence independently from another selected from the group consisting of: hydrogen, deuterium, $C_1$-$C_5$-alkyl,
wherein one or more hydrogen atoms are optionally substituted by deuterium; $C_2$-$C_8$-alkenyl,
wherein one or more hydrogen atoms are optionally substituted by deuterium; $C_2$-$C_8$-alkynyl,
wherein one or more hydrogen atoms are optionally substituted by deuterium; $C_6$-$C_{18}$-aryl,
which is optionally substituted with one or more substituents $R^6$; and $C_3$-$C_{17}$-heteroaryl,
which is optionally substituted with one or more substituents $R^6$.

$R^{12}$ is at each occurrence independently from another selected from the group consisting of: hydrogen, deuterium, $C_1$-$C_5$-alkyl,
wherein one or more hydrogen atoms are optionally substituted by deuterium; $C_2$-$C_8$-alkenyl,
wherein one or more hydrogen atoms are optionally substituted by deuterium; $C_2$-$C_8$-alkynyl,
wherein one or more hydrogen atoms are optionally substituted by deuterium; $C_6$-$C_{18}$-aryl,
which is optionally substituted with one or more substituents $R^6$; and $C_3$-$C_{17}$-heteroaryl,
which is optionally substituted with one or more substituents $R^6$.

$R^{13}$ is at each occurrence independently from another selected from the group consisting of hydrogen, deuterium, $C_1$-$C_5$-alkyl,
wherein one or more hydrogen atoms are optionally substituted by deuterium; $C_2$-$C_8$-alkenyl,
wherein one or more hydrogen atoms are optionally substituted by deuterium; $C_2$-$C_8$-alkynyl,
wherein one or more hydrogen atoms are optionally substituted by deuterium; $C_6$-$C_{18}$-aryl, which is optionally substituted with one or more substituents $R^6$; and $C_3$-$C_{17}$-heteroaryl,
which is optionally substituted with one or more substituents $R^6$;

$R^{21}$ is at each occurrence independently from another selected from the group consisting of:
hydrogen, deuterium, $C_1$-$C_5$-alkyl,
wherein one or more hydrogen atoms are optionally substituted by deuterium; $C_2$-$C_8$-alkenyl,
wherein one or more hydrogen atoms are optionally substituted by deuterium; $C_2$-$C_8$-alkynyl,
wherein one or more hydrogen atoms are optionally substituted by deuterium; $C_6$-$C_{18}$-aryl,
which is optionally substituted with one or more substituents $R^6$; and $C_3$-$C_{17}$-heteroaryl,
which is optionally substituted with one or more substituents $R^6$.

$R^{22}$ is at each occurrence independently from another selected from the group consisting of: hydrogen, deuterium, $C_1$-$C_5$-alkyl,
wherein one or more hydrogen atoms are optionally substituted by deuterium; $C_2$-$C_8$-alkenyl,
wherein one or more hydrogen atoms are optionally substituted by deuterium; $C_2$-$C_8$-alkynyl,
wherein one or more hydrogen atoms are optionally substituted by deuterium; $C_6$-$C_{18}$-aryl,
which is optionally substituted with one or more substituents $R^6$; and $C_3$-$C_{17}$-heteroaryl,
which is optionally substituted with one or more substituents $R^6$.

$R^{23}$ is at each occurrence independently from another selected from the group consisting of hydrogen, deuterium, $C_1$-$C_5$-alkyl,
wherein one or more hydrogen atoms are optionally substituted by deuterium; $C_2$-$C_8$-alkenyl,
wherein one or more hydrogen atoms are optionally substituted by deuterium; $C_2$-$C_8$-alkynyl,
wherein one or more hydrogen atoms are optionally substituted by deuterium; $C_6$-$C_{18}$-aryl,
which is optionally substituted with one or more substituents $R^6$; and $C_3$-$C_{17}$-heteroaryl,
which is optionally substituted with one or more substituents $R^6$;

$R^{II}$, $R^{III}$ and $R^{IV}$ is independently from another selected from the group consisting of: hydrogen, deuterium, $C_1$-$C_5$-alkyl,
wherein one or more hydrogen atoms are optionally substituted by deuterium; $C_2$-$C_8$-alkenyl,
wherein one or more hydrogen atoms are optionally substituted by deuterium; $C_2$-$C_8$-alkynyl,
wherein one or more hydrogen atoms are optionally substituted by deuterium; and $C_6$-$C_{18}$-aryl,
which is optionally substituted with one or more substituents $R^6$.

$R^a$ is at each occurrence independently from another selected from the group consisting of: hydrogen, deuterium, $N(R^5)_2$, $OR^5$, $Si(R^5)_3$, $B(OR^5)_2$, $OSOR^5$, $CF_3$, $CN$, $F$, $Br$, $I$, $C_1$-$C_{40}$-alkyl,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;
$C_1$-$C_{40}$-alkoxy,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;
$C_1$-$C_{40}$-thioalkoxy,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;
$C_2$-$C_{40}$-alkenyl,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;
$C_2$-$C_{40}$-alkynyl,
which is optionally substituted with one or more substituents $R^5$ and
wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;
$C_6$-$C_{60}$-aryl,
which is optionally substituted with one or more substituents $R^5$; and $C_3$-$C_{57}$-heteroaryl,
which is optionally substituted with one or more substituents $R^5$.

$R^5$ is at each occurrence independently from another selected from the group consisting of: hydrogen, deuterium, $N(R^6)_2$, $OR^6$, $Si(R^6)_3$, $B(OR^6)_2$, $OSO_2R^6$, $CF_3$, $CN$, $F$, $Br$, $I$, $C_1$-$C_{40}$-alkyl,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, $SO$, $SO_2$, $NR^6$, $O$, $S$ or $CONR^6$;
$C_1$-$C_{40}$-alkoxy,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, $SO$, $SO_2$, $NR^6$, $O$, $S$ or $CONR^6$;
$C_1$-$C_{40}$-thioalkoxy,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, $SO$, $SO_2$, $NR^6$, $O$, $S$ or $CONR^6$;
$C_2$-$C_{40}$-alkenyl,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, $SO$, $SO_2$, $NR^6$, $O$, $S$ or $CONR^6$;
$C_2$-$C_{40}$-alkynyl,
which is optionally substituted with one or more substituents $R^6$ and
wherein one or more non-adjacent $CH_2$-groups are optionally substituted by $R^6C{=}CR^6$, $C{\equiv}C$, $Si(R^6)_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

C$_6$-C$_{60}$-aryl,
which is optionally substituted with one or more substituents R$^6$; and C$_3$-C$_{57}$-heteroaryl,
which is optionally substituted with one or more substituents R$^6$.

R$^6$ is at each occurrence independently from another selected from the group consisting of hydrogen, deuterium, OPh, CF$_3$, CN, F, C$_1$-C$_5$-alkyl,
wherein optionally one or more hydrogen atoms are independently from each other substituted by deuterium, CN, CF$_3$, or F;

C$_1$-C$_5$-alkoxy,
wherein optionally one or more hydrogen atoms are independently from each other substituted by deuterium, CN, CF$_3$, or F;

C$_1$-C$_5$-thioalkoxy,
wherein optionally one or more hydrogen atoms are independently from each other substituted by deuterium, CN, CF$_3$, or F;

C$_2$-C$_5$-alkenyl,
wherein optionally one or more hydrogen atoms are independently from each other substituted by deuterium, CN, CF$_3$, or F;

C$_2$-C$_5$-alkynyl,
wherein optionally one or more hydrogen atoms are independently from each other substituted by deuterium, CN, CF$_3$, or F;

C$_6$-C$_{18}$-aryl,
which is optionally substituted with one or more C$_1$-C$_5$-alkyl substituents; C$_3$-C$_{17}$-heteroaryl,
which is optionally substituted with one or more C$_1$-C$_5$-alkyl substituents;

N(C$_6$-C$_{18}$-aryl)$_2$;
N(C$_3$-C$_{17}$-heteroaryl)$_2$; and
N(C$_3$-C$_{17}$-heteroaryl)(C$_6$-C$_{18}$-aryl).

The substituents R$^a$ or R$^5$, independently from each other, optionally form a mono- or polycyclic, aliphatic, aromatic and/or benzo-fused ring system with one or more substituents R$^a$ or R$^5$.

According to the invention,
at least one variable selected from the group consisting of X$^1$, X$^2$ is N, and
at least one variable selected from the group consisting of X$^3$, X$^4$ is N, and
at least one variable selected from the group consisting of X$^5$, X$^6$ is N.

In one embodiment, R$^{11}$, R$^{12}$, R$^{13}$, R$^{II}$, R$^{III}$ and R$^{IV}$ is independently from each other at each occurrence selected from the group consisting of H, methyl and phenyl (Ph), which is optionally substituted with one or more substituents independently from each other selected from the group consisting of Me, $^i$Pr, $^t$Bu, CN, CF$_3$, and Ph, R$^{21}$ is selected from the group consisting of H, methyl and phenyl, which is optionally substituted with one or more substituents independently from each other selected from the group consisting of Me, $^i$Pr, $^t$Bu, CN, CF$_3$, and Ph, if only one of X$^1$ and X$^2$ is N, R$^{22}$ is selected from the group consisting of H, methyl and phenyl, which is optionally substituted with one or more substituents independently from each other selected from the group consisting of Me, $^i$Pr, $^t$Bu, CN, CF$_3$, and Ph, if only one of X$^3$ and X$^4$ is N, and R$^{23}$ is at each occurrence independently from another selected from the group consisting of H, methyl and phenyl, which is optionally substituted with one or more substituents independently from each other selected from the group consisting of Me, $^i$Pr, $^t$Bu, CN, CF$_3$, and Ph, if only one of X$^5$ and X$^6$ is N.

In one embodiment, R$^{11}$, R$^{12}$, R$^{13}$, R$^{II}$, R$^{III}$ and R$^{IV}$ is independently from each other at each occurrence selected from the group consisting of H, methyl and phenyl, and R$^{21}$, R$^{22}$, R$^{23}$ is independently from each other at each occurrence selected from the group consisting of H, methyl and phenyl, if only one of X$^1$ and X$^2$ is N, only one of X$^3$ and X$^4$ is N, and only one of X$^5$ and X$^6$ is N, respectively.

In one embodiment, R$^{11}$, R$^{12}$ and R$^{13}$ is Ph, which is optionally substituted with one or more substituents independently from each other selected from the group consisting of Me, $^i$Pr, $^t$Bu, CN, CF$_3$, and Ph.

In one embodiment, R$^{11}$, R$^{12}$ and R$^{13}$ is Ph.

In one embodiment, R$^{21}$, R$^{22}$ and R$^{23}$ is H.

In one embodiment, R$^{11}$, R$^{12}$, R$^{13}$ is Ph at each occurrence and R$^{21}$, R$^{22}$, R$^{23}$, R$^{II}$, R$^{III}$ and R$^{IV}$ is H at each occurrence. Each of R$^{21}$, R$^{22}$, R$^{23}$ can be H, if from X$^1$ and X$^2$, X$^3$ and X$^4$, and X$^5$ and X$^6$, respectively, only one is N.

In one embodiment, X$^1$, and X$^2$ is N.
In one embodiment, X$^3$, and X$^4$ is N.
In one embodiment, X$^5$, and X$^6$ is N.
In one embodiment, X$^1$, X$^2$, X$^3$, X$^4$, X$^5$, and X$^6$ is N.
In one embodiment, X$^1$, X$^2$, X$^3$, X$^4$, X$^5$ is N, and X$^6$ is CR$^{23}$.
In one embodiment, X$^1$, X$^2$, X$^3$, X$^4$, X$^6$ is N, and X$^5$ is CR$^{23}$.
In one embodiment, X$^1$, X$^2$, X$^3$, X$^5$, X$^6$ is N and X$^4$ is CR$^{22}$.
In one embodiment, X$^1$, X$^2$, X$^4$, X$^5$, X$^6$ is N and X$^3$ is CR$^{22}$.
In one embodiment, X$^2$, X$^3$, X$^4$, X$^5$, X$^6$ is N and X$^1$ is CR$^{21}$.
In one embodiment, X$^1$, X$^3$, X$^4$, X$^5$, X$^6$ is N and X$^2$ is CR$^{21}$.
In one embodiment, X$^2$, X$^4$, X$^5$, X$^6$ is N, X$^1$ is CR$^{21}$, and X$^3$ is CR$^{22}$.
In one embodiment, X$^2$, X$^3$, X$^5$, X$^6$ is N, X$^1$ is CR$^{21}$, and X$^4$ is CR$^{22}$.
In one embodiment, X$^2$, X$^3$, X$^4$, X$^6$ is N, X$^1$ is CR$^{21}$, and X$^5$ is CR$^{23}$.
In one embodiment, X$^2$, X$^3$, X$^4$, X$^5$ is N, X$^1$ is CR$^{21}$, and X$^6$ is CR$^{23}$.
In one embodiment, X$^1$, X$^4$, X$^5$, X$^6$ is N, X$^2$ is CR$^{21}$, and X$^3$ is CR$^{22}$.
In one embodiment, X$^1$, X$^3$, X$^5$, X$^6$ is N, X$^2$ is CR$^{21}$, and X$^4$ is CR$^{22}$.
In one embodiment, X$^1$, X$^3$, X$^4$, X$^6$ is N, X$^2$ is CR$^{21}$, and X$^5$ is CR$^{23}$.
In one embodiment, X$^1$, X$^3$, X$^4$, X$^5$ is N, X$^2$ is CR$^{21}$, and X$^6$ is CR$^{23}$.
In one embodiment, X$^1$, X$^2$, X$^4$, X$^6$ is N, X$^3$ is CR$^{22}$, and X$^5$ is CR$^{23}$.
In one embodiment, X$^1$, X$^2$, X$^4$, X$^5$ is N, X$^3$ is CR$^{22}$, and X$^6$ is CR$^{23}$.
In one embodiment, X$^1$, X$^2$, X$^3$, X$^6$ is N, X$^4$ is CR$^{22}$, and X$^5$ is CR$^{23}$.
In one embodiment, X$^1$, X$^2$, X$^3$, X$^5$ is N, X$^4$ is CR$^{22}$, and X$^6$ is CR$^{23}$.
In one embodiment, X$^2$, X$^4$, X$^6$ is N, X$^1$ is CR$^{21}$, X$^3$ is CR$^{22}$, and X$^5$ is C$^{23}$.
In one embodiment, X$^2$, X$^4$, X$^5$ is N, X$^1$ is CR$^{21}$, X$^3$ is CR$^{22}$, and X$^6$ is C$^{23}$.
In one embodiment, X$^2$, X$^3$, X$^6$ is N, X$^1$ is CR$^{21}$, X$^4$ is CR$^{22}$, and X$^5$ is C$^{23}$.

In one embodiment, $X^2$, $X^3$, $X^5$ is N, $X^1$ is $CR^{21}$, $X^4$ is $CR^{22}$, and $X^6$ is $C^{23}$.

In one embodiment, $X^1$, $X^4$, $X^6$ is N, $X^2$ is $CR^{21}$, $X^3$ is $CR^{22}$, and $X^5$ is $C^{23}$.

In one embodiment, $X^1$, $X^4$, $X^5$ is N, $X^2$ is $CR^{21}$, $X^3$ is $CR^{22}$, and $X^6$ is $C^{23}$.

In one embodiment, $X^1$, $X^3$, $X^6$ is N, $X^2$ is $CR^{21}$, $X^4$ is $CR^{22}$, and $X^5$ is $C^{23}$.

In one embodiment, $X^1$, $X^3$, $X^5$ is N, $X^2$ is $CR^{21}$, $X^4$ is $CR^{22}$, and $X^6$ is $C^{23}$.

In one embodiment, $R^{II}$ is hydrogen.

In one embodiment, $R^{III}$ is hydrogen.

In one embodiment, $R^{IV}$ is hydrogen.

In one embodiment, $R^{II}$, $R^{III}$ and $R^{IV}$ is hydrogen.

In a further embodiment of the invention, $R^a$ is at each occurrence independently from another selected from the group consisting of:

hydrogen, Me,
$^i$Pr,
$^t$Bu,
CN, $CF_3$,
$SiMe_3$, $SiPh_3$,
Ph, which is optionally substituted with one or more substituents independently from each other selected from the group consisting of Me, $^i$Pr, $^t$Bu, CN, $CF_3$, and Ph,
pyridinyl, which is optionally substituted with one or more substituents independently from each other selected from the group consisting of Me, $^i$Pr, $^t$Bu, CN, $CF_3$, and Ph,
pyrimidinyl, which is optionally substituted with one or more substituents independently from each other selected from the group consisting of Me, $^i$Pr, $^t$Bu, CN, $CF_3$, and Ph,
carbazolyl, which is optionally substituted with one or more substituents independently from each other selected from the group consisting of Me, $^i$Pr, $^t$Bu, CN, $CF_3$, and Ph,
triazinyl, which is optionally substituted with one or more substituents independently from each other selected from the group consisting of Me, $^i$Pr, $^t$Bu, CN, $CF_3$, and Ph,
and $N(Ph)_2$.

In a further embodiment of the invention, $R^a$ is at each occurrence independently from another selected from the group consisting of:

hydrogen,
Me,
$^i$Pr,
$^t$Bu,
CN,
$CF_3$,
$SiMe_3$,
$SiPh_3$,
Ph, which is optionally substituted with one or more substituents independently from each other selected from the group consisting of Me, $^i$Pr, $^t$Bu, CN, $CF_3$, and Ph,
pyridinyl, which is optionally substituted with one or more substituents independently from each other selected from the group consisting of Me, Pr, $^t$Bu, CN, $CF_3$, and Ph,
pyrimidinyl, which is optionally substituted with one or more substituents independently from each other selected from the group consisting of Me, $^i$Pr, $^t$Bu, $CF_3$, and Ph, and
triazinyl, which is optionally substituted with one or more substituents independently from each other selected from the group consisting of Me, $^i$Pr, $^t$Bu, CN, $CF_3$, and Ph.

In one embodiment, $R^a$ is at each occurrence independently from another selected from the group consisting of hydrogen (H), methyl (Me), i-propyl ($CH(CH_3)_2$) ($^i$Pr), t-butyl ($^t$Bu), phenyl(Ph), CN, $CF_3$, and diphenylamine ($NPh_2$).

In one embodiment, $R^a$ is at each occurrence H.

In one embodiment of the invention, the organic molecules comprise or consist of a structure of formula III:

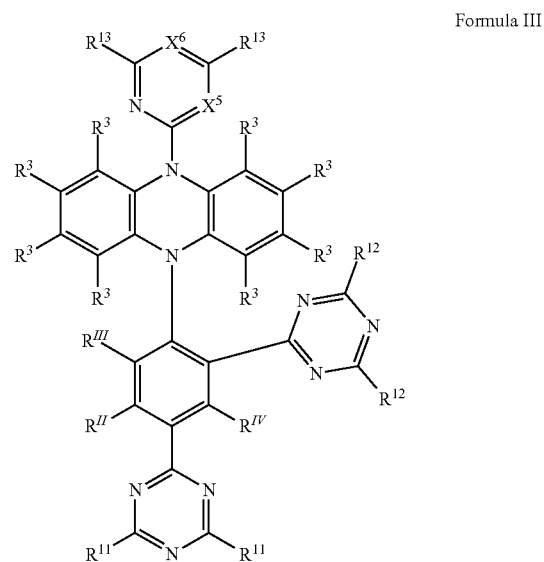

Formula III wherein the aforementioned definitions apply.

In a further embodiment of the invention, the organic molecules comprise or consist of a structure of formula IIIa:

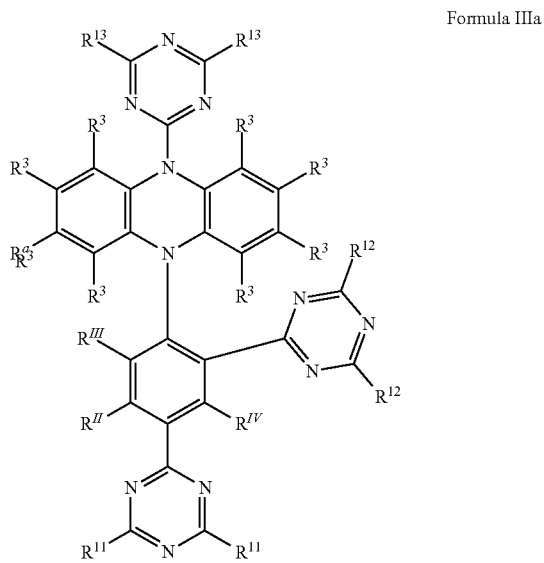

Formula IIIa wherein the aforementioned definitions apply.

In a further embodiment of the invention, the organic molecules comprise or consist of a structure of formula IIIb:

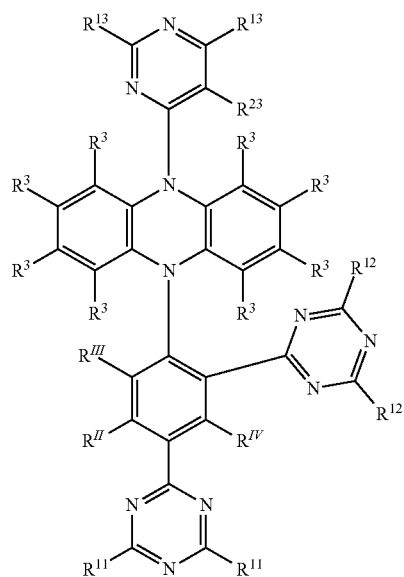

Formula IIIb wherein the aforementioned definitions apply.

In a further embodiment of the invention, the organic molecules comprise or consist of a structure of formula IIIc:

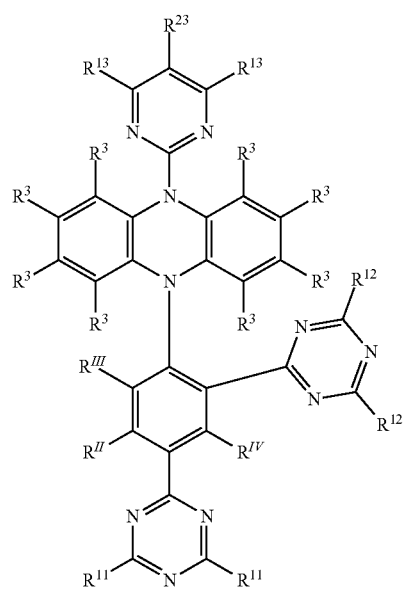

Formula IIIc wherein the aforementioned definitions apply.

In one embodiment of the invention, the organic molecules comprise or consist of formula IV:

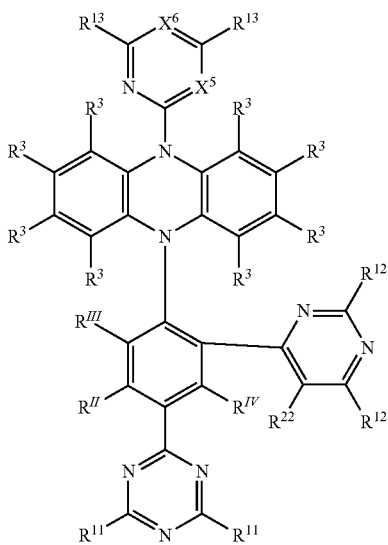

Formula IV wherein the aforementioned definitions apply.

In a further embodiment of the invention, the organic molecules comprise or consist of a structure of formula IVa:

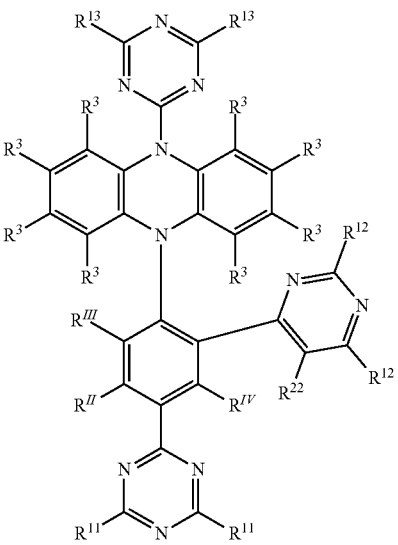

Formula IVa wherein the aforementioned definitions apply.

In a further embodiment of the invention, the organic molecules comprise or consist of a structure of formula IVb:

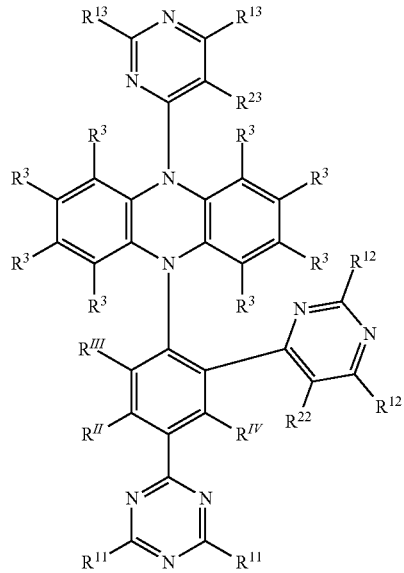

Formula IVb wherein the aforementioned definitions apply.

In a further embodiment of the invention, the organic molecules comprise or consist of a structure of formula IVc:

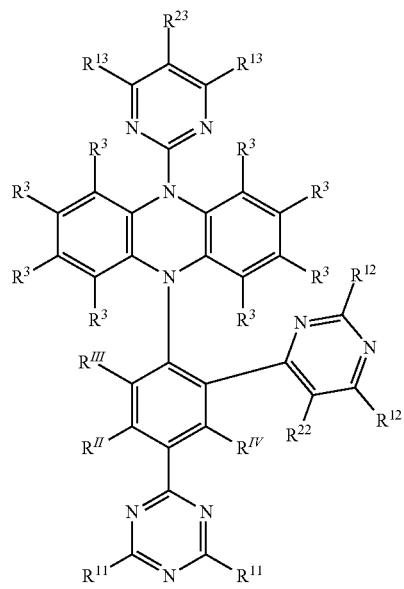

Formula IVc wherein the aforementioned definitions apply.

In one embodiment of the invention, the organic molecules comprise or consist of a structure of formula V:

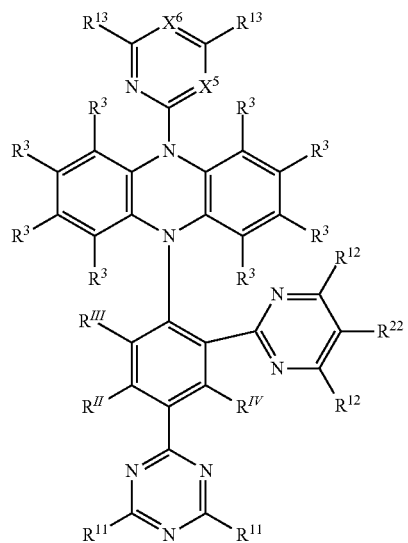

Formula V wherein the aforementioned definitions apply.

In a further embodiment of the invention, the organic molecule comprises or consists of a structure of formula Va:

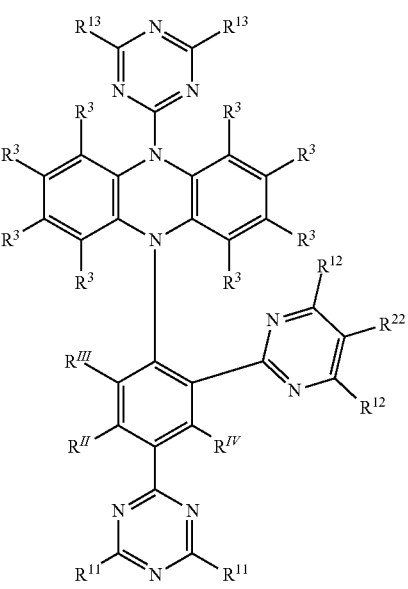

Formula Va wherein the aforementioned definitions apply.

In a further embodiment of the invention, the organic molecule comprises or consists of a structure of formula Vb:

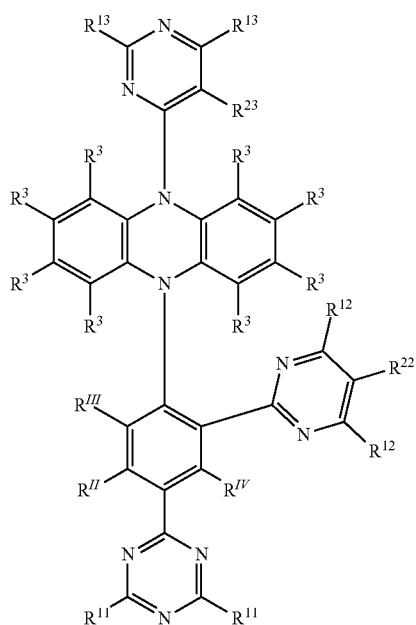

Formula Vb wherein the aforementioned definitions apply.

In a further embodiment of the invention, the organic molecules comprise or consist of a structure of formula Vc:

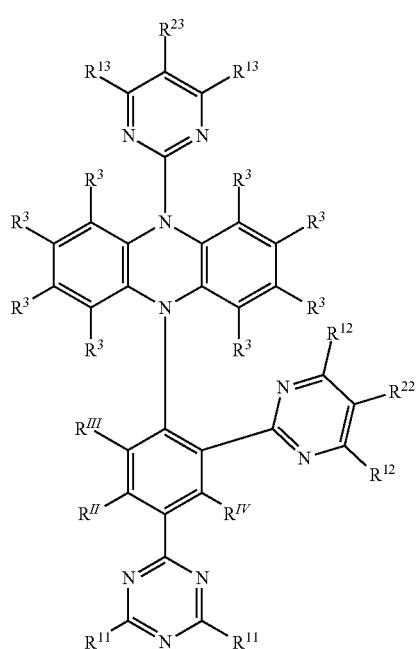

Formula Vc wherein the aforementioned definitions apply.

In one embodiment of the invention, the organic molecules comprise or consist of a structure of formula VI:

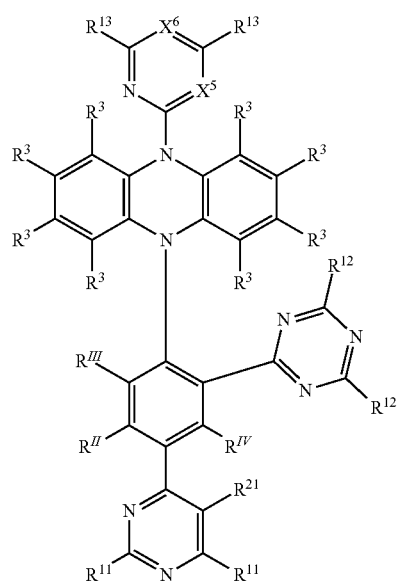

Formula VI wherein the aforementioned definitions apply.

In a further embodiment of the invention, the organic molecules comprise or consist of a structure of formula VIa:

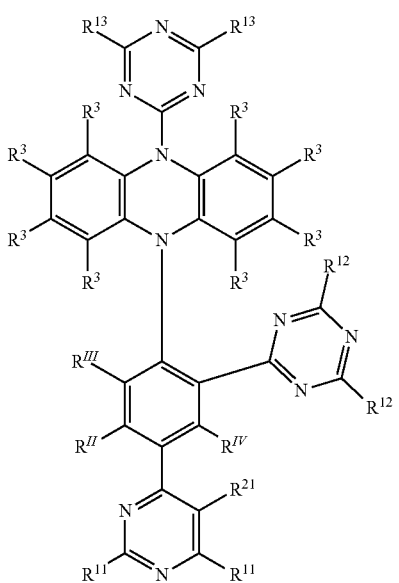

Formula VIa wherein the aforementioned definitions apply.

In a further embodiment of the invention, the organic molecules comprise or consist of a structure of formula VIb:

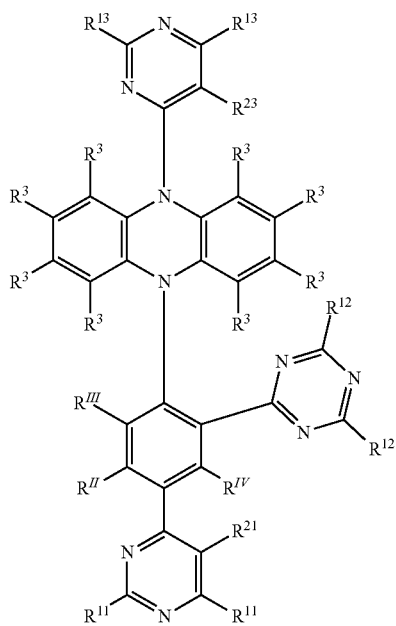

Formula VIb wherein the aforementioned definitions apply.

In a further embodiment of the invention, the organic molecules comprise or consist of a structure of formula VIc:

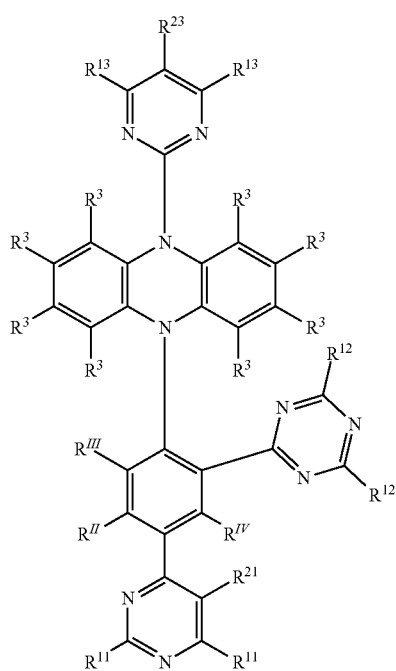

Formula VIc wherein the aforementioned definitions apply.

In another embodiment of the invention, the organic molecules comprise or consist of a structure of formula VII:

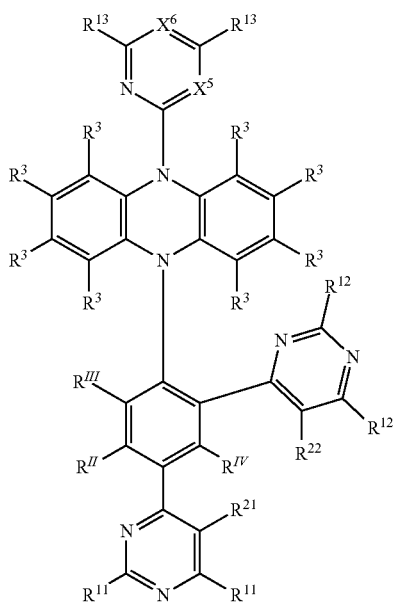

Formula VII wherein the aforementioned definitions apply.

In a further embodiment of the invention, the organic molecules comprise or consist of a structure of formula VIIa:

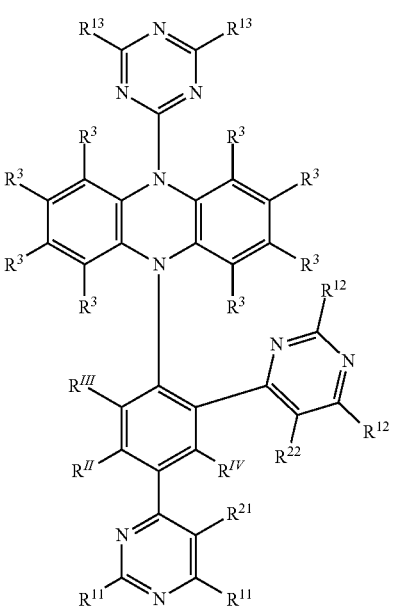

Formula VIIa wherein the aforementioned definitions apply.

In a further embodiment of the invention, the organic molecules comprise or consist of a structure of formula VIIb:

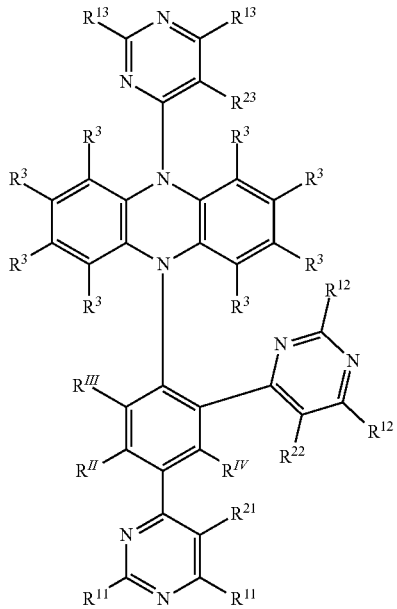

Formula VIIb wherein the aforementioned definitions apply.

In a further embodiment of the invention, the organic molecules comprise or consist of a structure of formula VIIc:

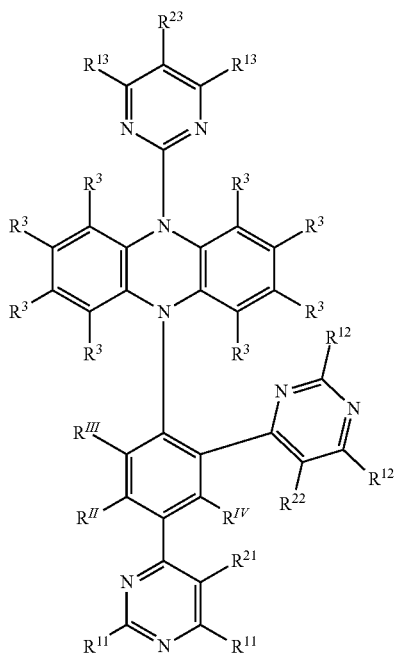

Formula VIIc wherein the aforementioned definitions apply.

In one embodiment of the invention, the organic molecules comprise or consist of a structure of formula VIII:

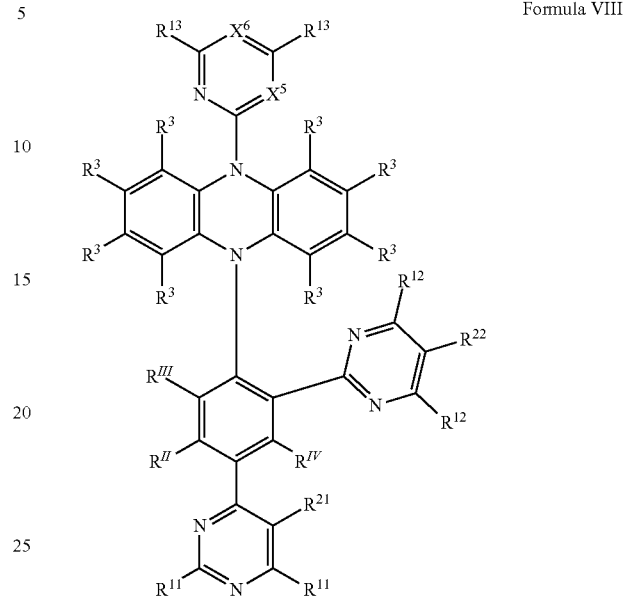

Formula VIII wherein the aforementioned definitions apply.

In a further embodiment of the invention, the organic molecules comprise or consist of a structure of formula VIIIa:

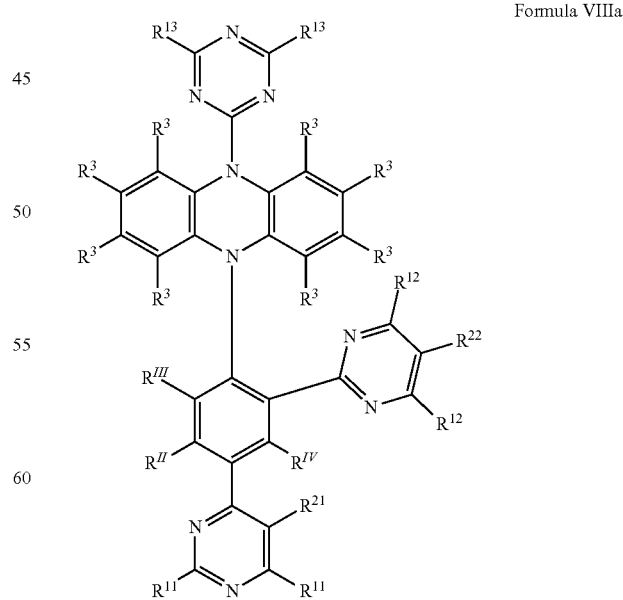

Formula VIIIa wherein the aforementioned definitions apply.

In a further embodiment of the invention, the organic molecules comprise or consist of a structure of formula VIIIb:

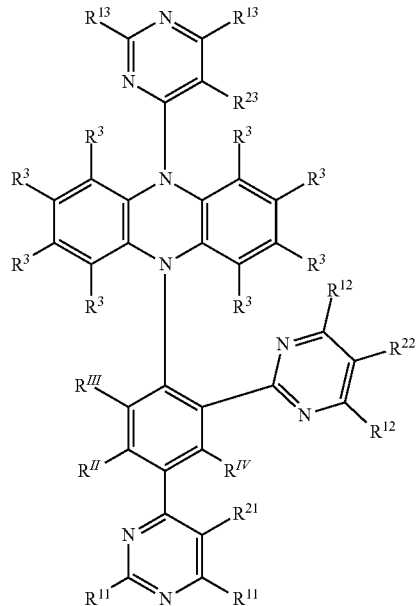

Formula VIIIb wherein the aforementioned definitions apply.

In a further embodiment of the invention, the organic molecules comprise or consist of a structure of formula VIIIc:

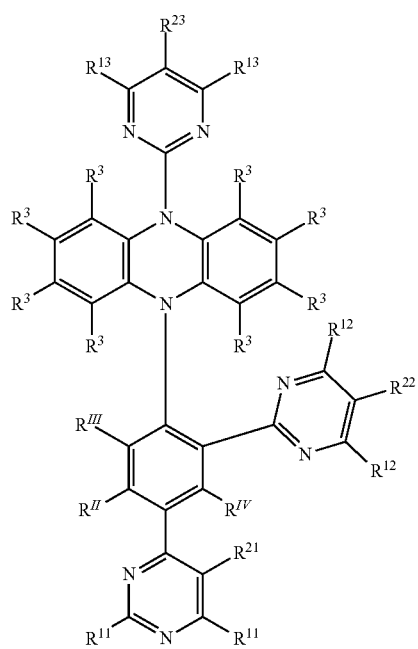

Formula VIIIc wherein the aforementioned definitions apply.

In one embodiment of the invention, the organic molecules comprise or consist of a structure of formula IX:

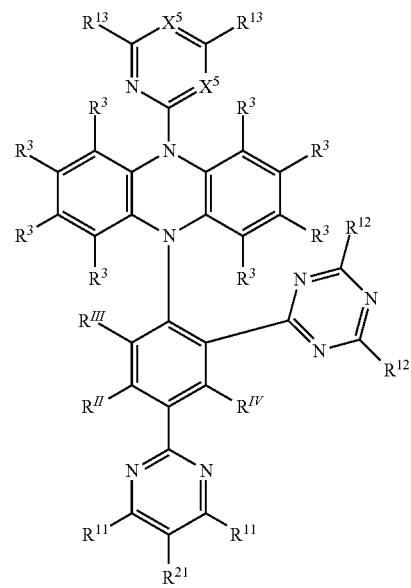

Formula IX wherein the aforementioned definitions apply.

In a further embodiment of the invention, the organic molecules comprise or consist of a structure of formula IXa:

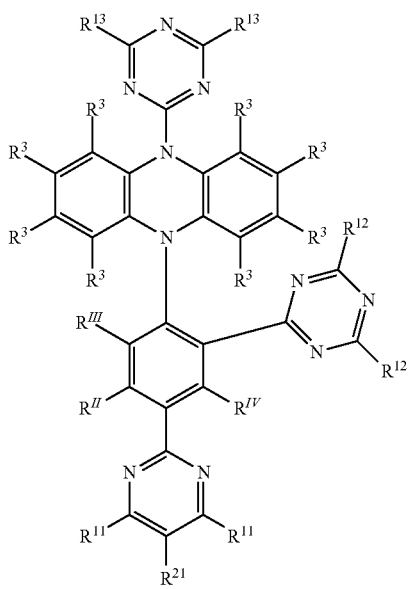

Formula IXa wherein the aforementioned definitions apply.

In a further embodiment of the invention, the organic molecules comprise or consist of a structure of formula IXb:

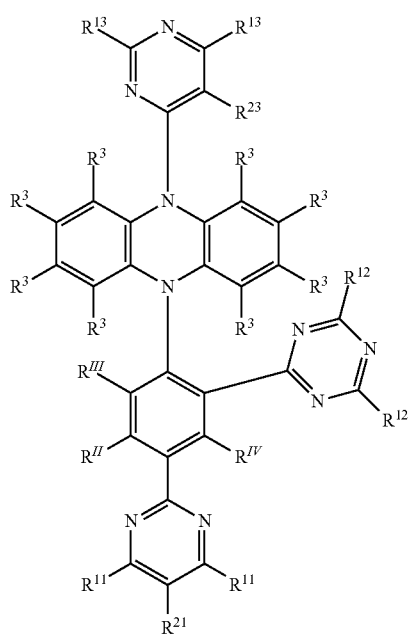

Formula IXb wherein the aforementioned definitions apply.

In a further embodiment of the invention, the organic molecules comprise or consist of a structure of formula IXc:

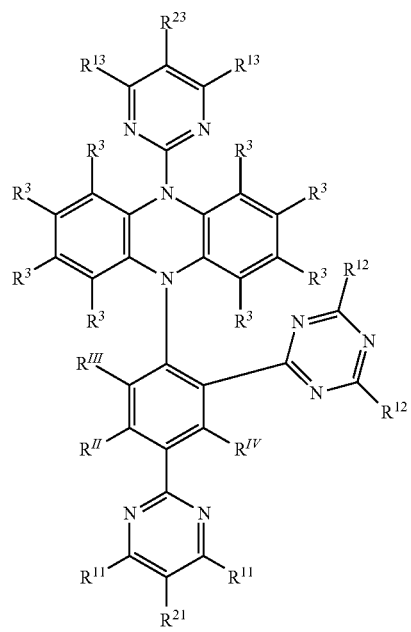

Formula IXc wherein the aforementioned definitions apply.

In one embodiment of the invention, the organic molecules comprise or consist of a structure of formula X:

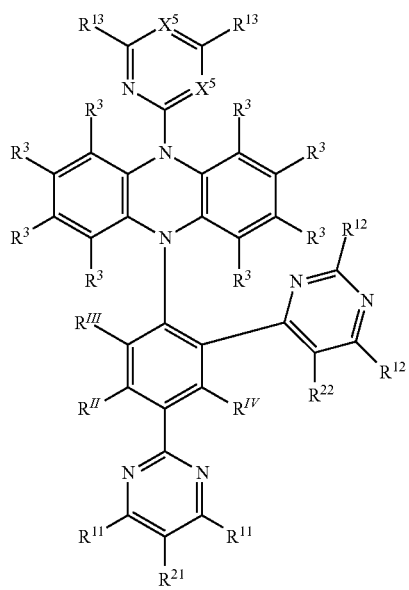

Formula X wherein the aforementioned definitions apply.

In a further embodiment of the invention, the organic molecules comprise or consist of a structure of formula Xa:

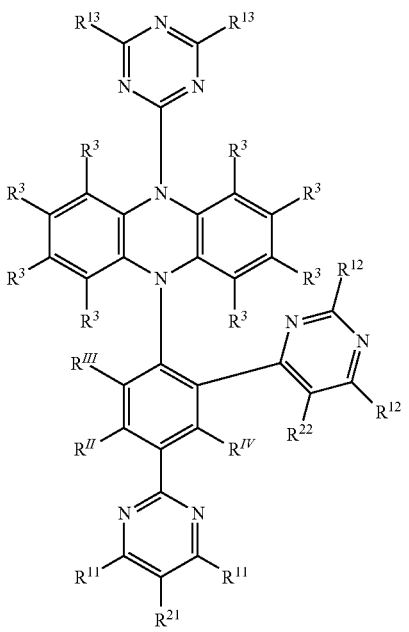

Formula Xa wherein the aforementioned definitions apply.

In a further embodiment of the invention, the organic molecules comprise or consist of a structure of formula Xb:

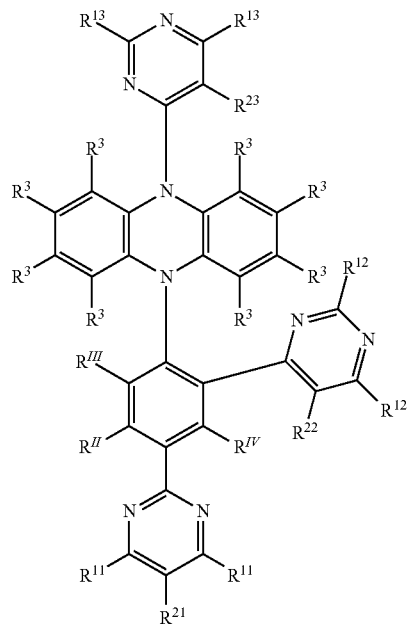

Formula Xb wherein the aforementioned definitions apply.

In a further embodiment of the invention, the organic molecules comprise or consist of a structure of formula Xc:

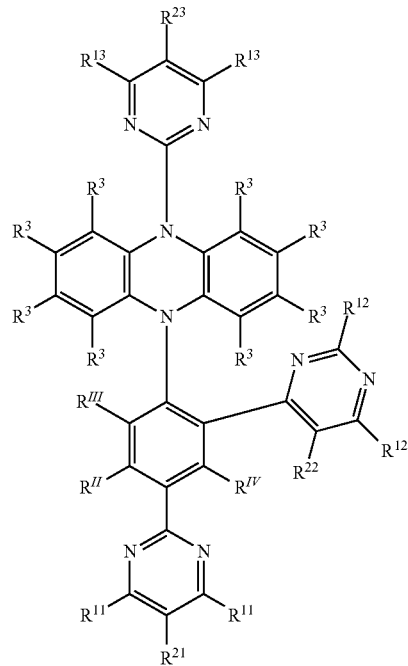

Formula Xc wherein the aforementioned definitions apply.

In one embodiment of the invention, the organic molecules comprise or consist of a structure of formula XI:

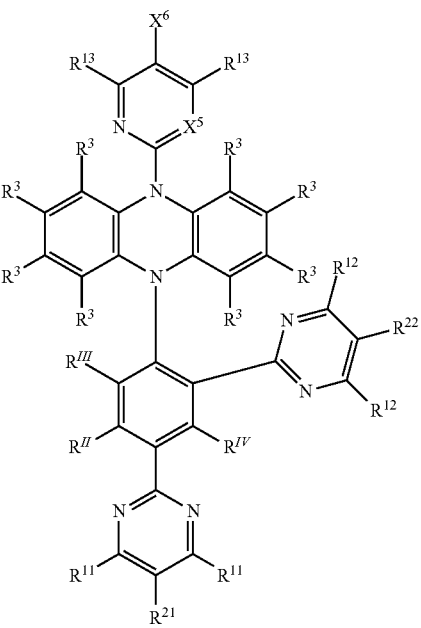

Formula XI wherein the aforementioned definitions apply.

In a further embodiment of the invention, the organic molecules comprise or consist of a structure of formula XIa:

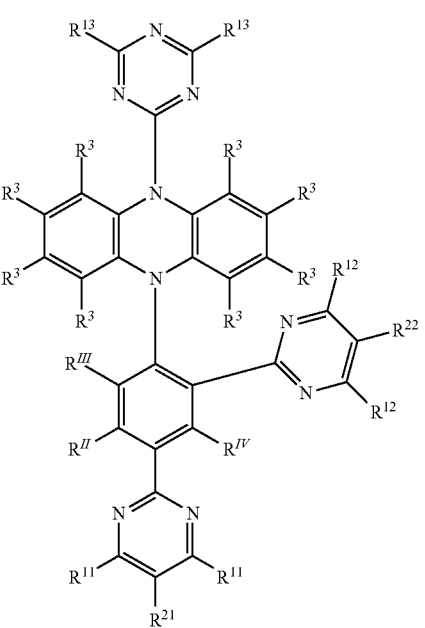

Formula XIa wherein the aforementioned definitions apply.

In a further embodiment of the invention, the organic molecules comprise or consist of a structure of formula XIb:

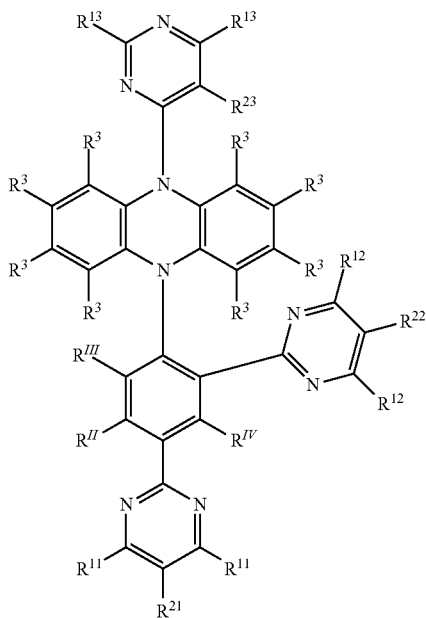

Formula XIb wherein the aforementioned definitions apply.

In a further embodiment of the invention, the organic molecules comprise or consist of a structure of a structure of formula XIc:

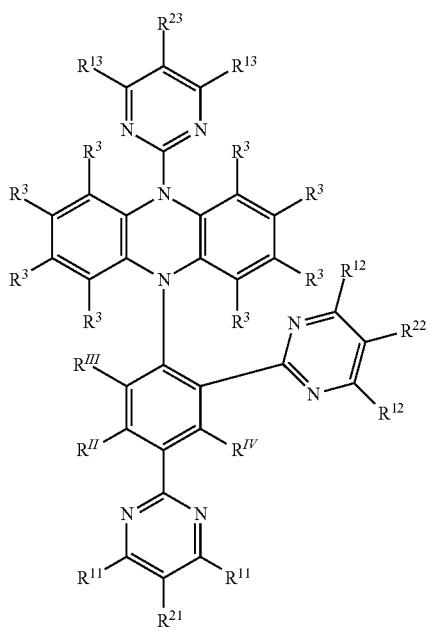

Formula XIc wherein the aforementioned definitions apply.

As used above and herein, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms.

Again, the terms "heteroaryl" and "heteroaromatic" may be understood in the broadest sense as any mono-, bi- or polycyclic hetero-aromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application the term aryl group or heteroaryl group comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the abovementioned groups.

As used throughout the present application the term cyclic group may be understood in the broadest sense as any mono-, bi- or polycyclic moieties.

As used above and herein, the term alkyl group may be understood in the broadest sense as any linear, branched, or cyclic alkyl substituent. In particular, the term alkyl comprises the substituents methyl (Me), ethyl (Et), n-propyl ($^n$Pr), i-propyl ($^i$Pr), cyclopropyl, n-butyl ($^n$Bu), i-butyl ($^i$Bu), s-butyl ($^s$Bu), t-butyl ($^t$Bu), cyclobutyl, 2-methylbutyl, n-pentyl, s-pentyl, t-pentyl, 2-pentyl, neo-pentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used above and herein, the term alkenyl comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used above and herein, the term alkynyl comprises linear, branched, and cyclic alkynyl substituents. The term alkynyl group exemplarily comprises ethynyl, propynyl, butynyl, pentynyl, hexynyl, heptynyl or octynyl.

As used above and herein, the term alkoxy comprises linear, branched, and cyclic alkoxy substituents. The term alkoxy group exemplarily comprises methoxy, ethoxy, n-propoxy, i-propoxy, n-butoxy, i-butoxy, s-butoxy, t-butoxy and 2-methylbutoxy.

As used above and herein, the term thioalkoxy comprises linear, branched, and cyclic thioalkoxy substituents, in which the O of the exemplarily alkoxy groups is replaced by S.

As used above and herein, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

The organic molecules according to the invention have an excited state lifetime of not more than 25 µs, of not more than 15 µs, in particular of not more than 10 µs, more preferably of not more than 8 µs or not more than 6 µs, even more preferably of not more than 4 µs in a film of mCBP (3,3-di(9H-carbazol-9-yl)biphenyl) with 10% by weight of organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (S1) and the first excited triplet state (T1), of less than 5000 cm$^{-1}$, preferably less than 3000 cm$^{-1}$, more preferably less than 1500 cm$^{-1}$, even more preferably less than 1000 cm$^{-1}$ or even less than 500 cm$^{-1}$.

In a further embodiment of the invention, the organic molecules according to the invention have an emission peak in the visible or nearest ultraviolet range, i.e. in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of mCBP (3,3-di(9H-carbazol-9-yl)biphenyl) with 10% by weight of organic molecule at room temperature.

In a further embodiment of the invention, the organic molecules according to the invention have an emission peak in the visible or nearest ultraviolet range, i.e. in the range of a wavelength of from 380 to 800 nm, with a full width at half maximum of less than 0.40 eV in a film of mCBP (3,3-di(9H-carbazol-9-yl)biphenyl) with 10% by weight of organic molecule at room temperature.

Orbital and excited state energies can be determined either by means of experimental methods or by calculations employing quantum-chemical methods, in particular density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is calculated as $E^{HOMO}+E^{gap}$, wherein $E^{gap}$ is determined as follows: For host compounds, the onset of the emission spectrum of a film with 10% by weight of host in mCBP (3,3-di(9H-carbazol-9-yl)biphenyl) is used as $E^{gap}$, unless stated otherwise. For emitter molecules, $E^{gap}$ is determined as the energy at which the excitation and emission spectra of a film with 10% by weight of emitter in mCBP cross.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of mCBP with 10% by weight of emitter. Both for host and emitter compounds, the energy of the first excited singlet state S1 is determined from the onset of the emission spectrum, if not otherwise stated measured in a film of mCBP with 10% by weight of host or emitter compound.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing the organic molecules (with an optional subsequent reaction) of the invention, wherein a palladium catalyzed cross-coupling reaction is used:

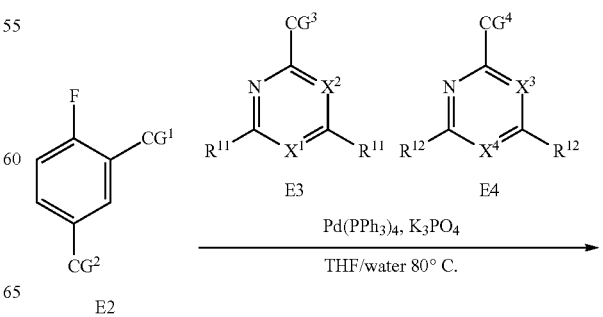

-continued

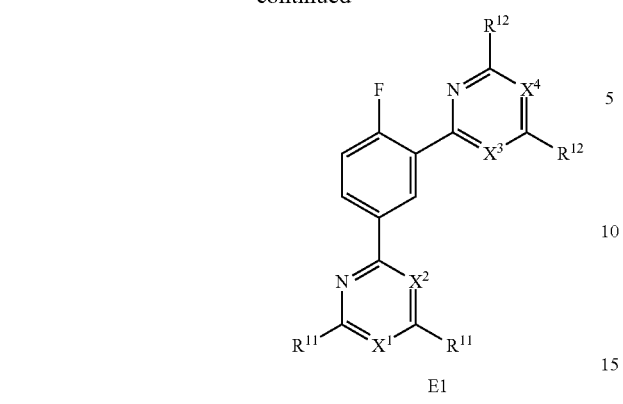

E1

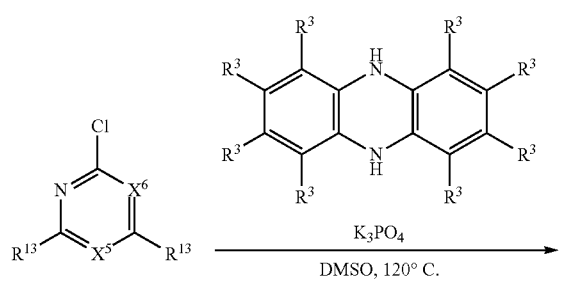

K₃PO₄
DMSO, 120° C.

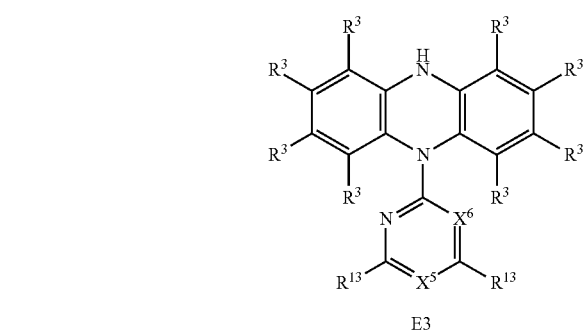

E3

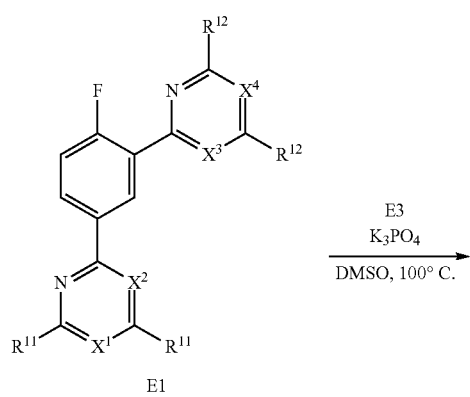

E1

E3
K₃PO₄
DMSO, 100° C.

-continued

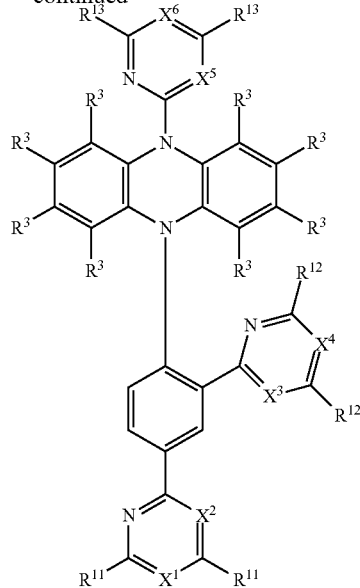

According to the invention, a 1-fluorobenzene, which is substituted with a coupling group $CG^1$ in 2-position and which is substituted with a coupling group $CG^2$ in 4-position, is used as a reactant, which is reacted with two heterocycles, one substituted with a coupling group $CG^3$ (reactant E3) and one with a coupling group $CG^4$ (reactant E4). The coupling groups $CG^1$ and $CG^4$ are chosen as a reaction pair to introduce the heterocycle of E4 at the position of $CG^1$. Accordingly, coupling groups $CG^2$ and $CG^3$ are chosen reaction pair for introducing the heterocycle of E3 at the position of $CG^2$. Preferably, a so-called Suzuki coupling reaction is used. Here, either $CG^1$ is chosen from Cl, Br or I, and $CG^4$ is a boronic acid group or a boronic acid ester group, in particular a boronic acid pinacol ester group, or $CG^1$ is a boronic acid group or a boronic acid ester group, in particular a boronic acid pinacol ester group, and $CG^4$ is chosen from Cl, Br or I. Analogously, either $CG^2$ is chosen from Cl, Br or I, and $CG^3$ is a boronic acid group or a boronic acid ester group, in particular a boronic acid pinacol ester group, or $CG^2$ is a boronic acid group or a boronic acid ester group, in particular a boronic acid pinacol ester group, and $CG^3$ is chosen from Cl, Br or I. The person skilled in the art is aware that in order to introduce different heterocycles via the coupling reactions of E3 with E2 and E4 with E2, either first E2 is reacted with E3 and the resulting intermediate is subsequently reacted with E4 to yield E1, or first E2 is reacted with E4 and the resulting intermediate is subsequently reacted with E3 to yield E1. In this constellation, either $CG^1$ and $CG^3$ are independently from each other a boronic acid group or a boronic acid ester group and $CG^2$ and $CG^4$ are independently from each other chosen from Cl, Br or I, or $CG^2$ and $CG^4$ are independently from each other a boronic acid group or a boronic acid ester group and $CG^1$ and $CG^3$ are independently from each other chosen from Cl, Br or I.

For the reaction of a nitrogen heterocycle in a nucleophilic aromatic substitution with an aryl halide, preferably an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, preferably an aryl bromide, an aryl iodide, aryl triflate or an aryl tosylate.

A further aspect of the invention relates to the use of an organic molecule according to the invention as a luminescent emitter or as an absorber, and/or as host material and/or as electron transport material, and/or as hole injection material, and/or as hole blocking material in an optoelectronic device.

The optoelectronic device may be understood in the broadest sense as any device based on organic materials that is suitable for emitting light in the visible or nearest ultra-violet (UV) range, i.e. in the range of a wavelength of from 380 to 800 nm. More preferably, optoelectronic device may be able to emit light in the visible range, i.e. of from 400 to 800 nm.

In the context of such use, the optoelectronic device is more particularly selected from the group consisting of:
  organic light-emitting diodes (OLEDs),
  light-emitting electrochemical cells,
  OLED sensors, especially in gas and vapour sensors not hermetically externally shielded,
  organic diodes,
  organic solar cells,
  organic transistors,
  organic field-effect transistors,
  organic lasers and
  down-conversion elements.

In a preferred embodiment in the context of such use, the optoelectronic device is a device selected from the group consisting of an organic light emitting diode (OLED), a light emitting electrochemical cell (LEC), and a light-emitting transistor.

In the case of the use, the fraction of the organic molecule according to the invention in the emission layer in an optoelectronic device, more particularly in OLEDs, is 1% to 99% by weight, more particularly 5% to 80% by weight. In an alternative embodiment, the proportion of the organic molecule in the emission layer is 100% by weight.

In one embodiment, the light-emitting layer of an organic light-emitting diode comprises the organic molecules according to the invention.

In the case of the use, the fraction of the organic molecule according to the invention in the emission layer in an optoelectronic device, more particularly in OLEDs, is 1% to 99% by weight, more particularly 5% to 80% by weight. In an alternative embodiment, the proportion of the organic molecule in the emission layer is 100% by weight.

In one embodiment, the light-emitting layer comprises not only the organic molecules according to the invention, but also a host material whose triplet (T1) and singlet (S1) energy levels are energetically higher than the triplet (T1) and singlet (S1) energy levels of the organic molecule.

A further aspect of the invention relates to a composition comprising or consisting of:
  (a) at least one organic molecule according to the invention, in particular in the form of an emitter and/or a host, and
  (b) one or more emitter and/or host materials, which differ from the organic molecule according to the invention and
  (c) optional one or more dyes and/or one or more solvents.

In a further embodiment of the invention, the composition has a photoluminescence quantum yield (PLQY) of more than 30%, preferably more than 40%, more preferably more than 60%, even more preferably more than 80% or even more than 90% at room temperature.

Compositions with at Least One Further Emitter

One embodiment of the invention relates to a composition comprising or consisting of:
  (i) 1-50% by weight, preferably 5-40% by weight, in particular 10-30% by weight, of the organic molecule according to the invention;
  (ii) 5-98% by weight, preferably 30-93.9% by weight, in particular 40-88% by weight, of one host compound H;
  (iii) 1-30% by weight, in particular 1-20% by weight, preferably 1-5% by weight, of at least one further emitter molecule F with a structure differing from the structure of the molecules according to the invention; and
  (iv) optionally 0-94% by weight, preferably 0.1-65% by weight, in particular 1-50% by weight, of at least one further host compound D with a structure differing from the structure of the molecules according to the invention; and
  (v) optionally 0-94% by weight, preferably 0-65% by weight, in particular 0-50% by weight, of a solvent.

The components or the compositions are chosen such that the sum of the weight of the components add up to 100%.

In a further embodiment of the invention, the composition has an emission peak in the visible or nearest ultraviolet range, i.e. in the range of a wavelength of from 380 to 800 nm.

In one embodiment of the invention, the at least one further emitter molecule F is a purely organic emitter.

In one embodiment of the invention, the at least one further emitter molecule F is a purely organic TADF emitter. Purely organic TADF emitters are known from the state of the art, e.g. Wong and Zysman-Colman ("Purely Organic Thermally Activated Delayed Fluorescence Materials for Organic Light-Emitting Diodes", Adv. Mater. 2017 Jun;29 (22)).

In one embodiment of the invention, the at least one further emitter molecule F is a fluorescence emitter, in particular a blue, a green, a yellow or a red fluorescence emitter.

In one embodiment of the invention, the at least one further emitter molecule F is a fluorescence emitter, in particular a red, a yellow or a green fluorescence emitter.

In a further embodiment of the invention, the composition, containing the at least one further emitter molecule F shows an emission peak in the visible or nearest ultraviolet range, i.e. in the range of a wavelength of from 380 nm to 800 nm, with a full width at half maximum of less than 0.30 eV, in particular less than 0.25 eV, preferably less than 0.22 eV, more preferably less than 0.19 eV or even less than 0.17 eV at room temperature, with a lower limit of 0.05 eV.

Composition Wherein the at Least One Further Emitter Molecule F is a Green Fluorescence Emitter In a further embodiment of the invention, the at least one further emitter molecule F is a fluorescence emitter, in particular a green fluorescence emitter.

In one embodiment, the at least one further emitter molecule F is a fluorescence emitter selected from the following group:
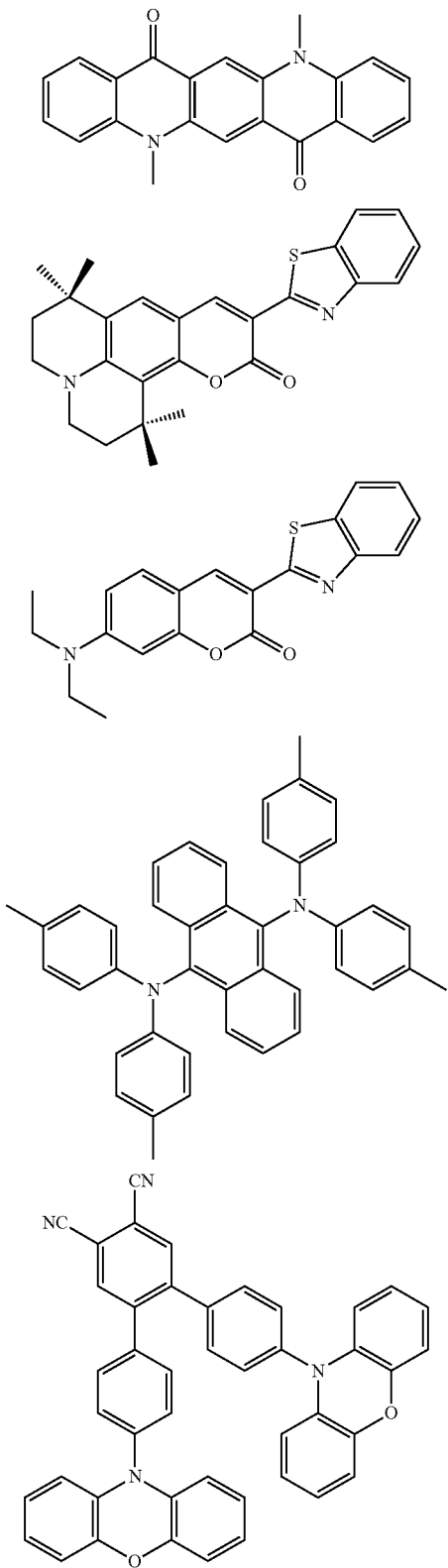
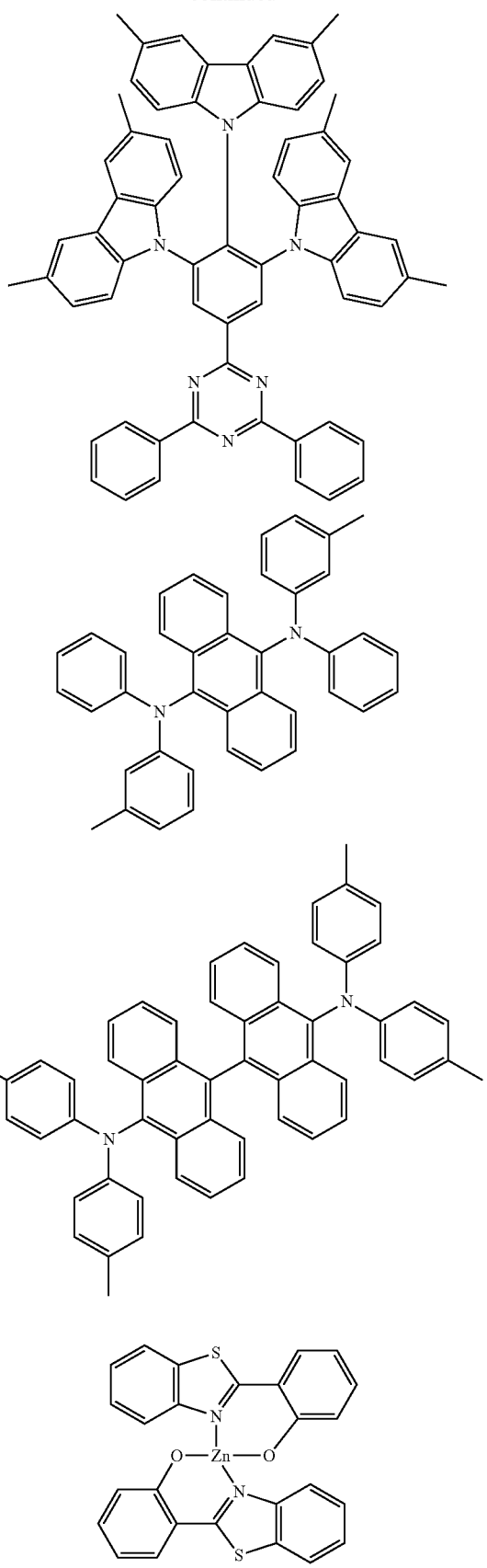

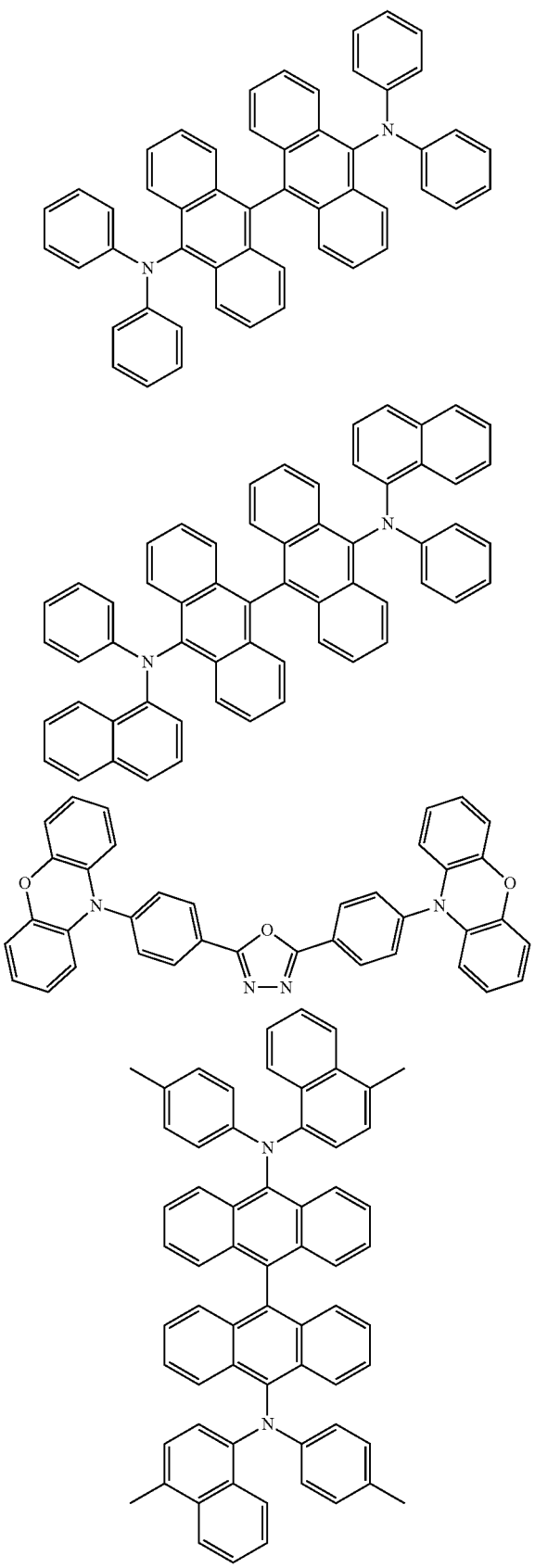
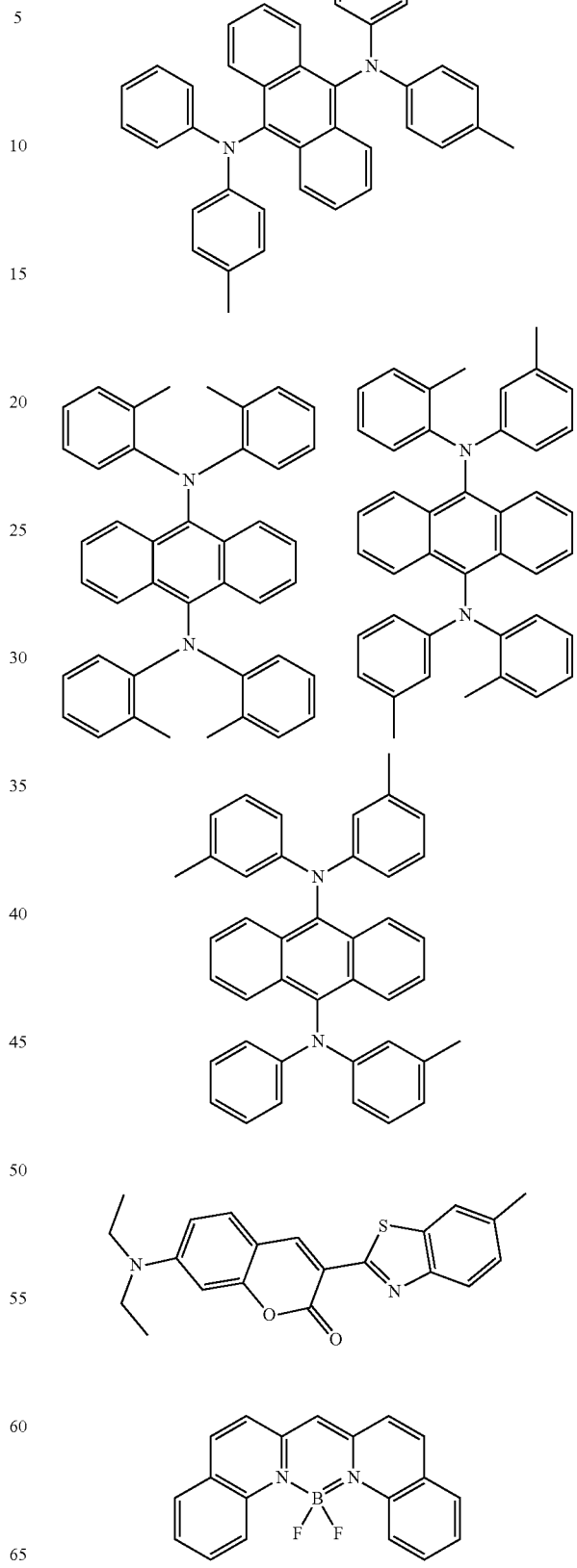

37
-continued
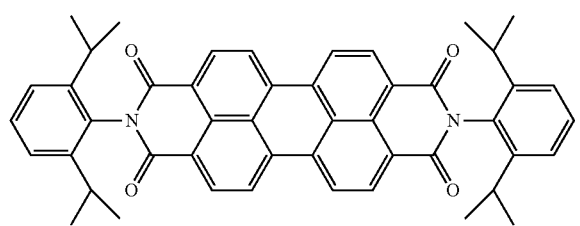
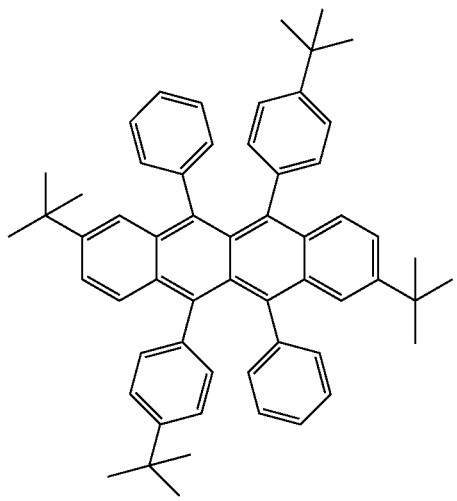
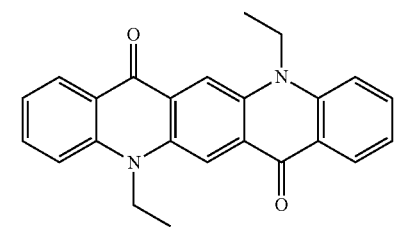
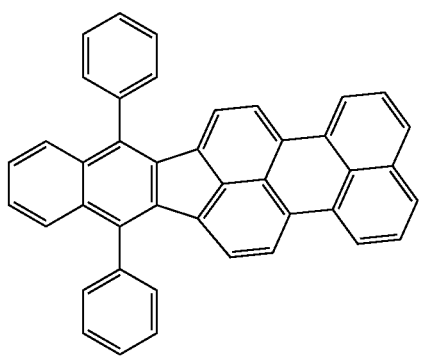
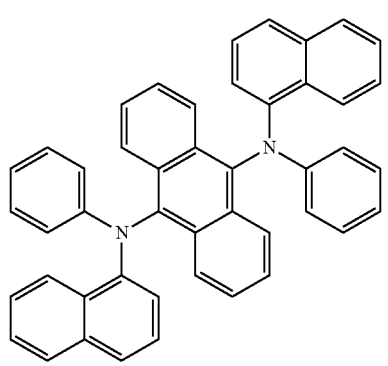
38
-continued
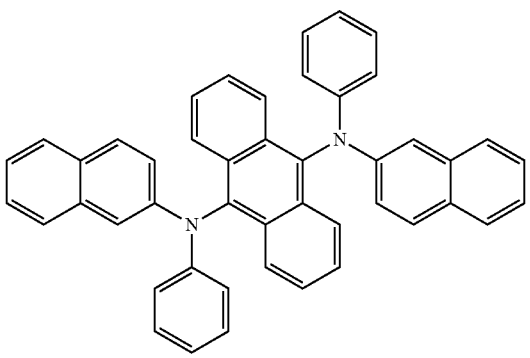
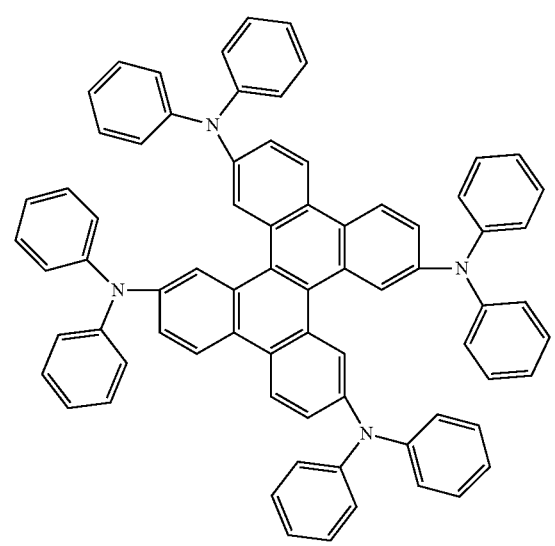
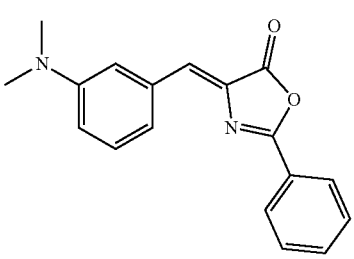
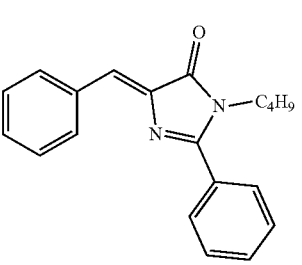

-continued

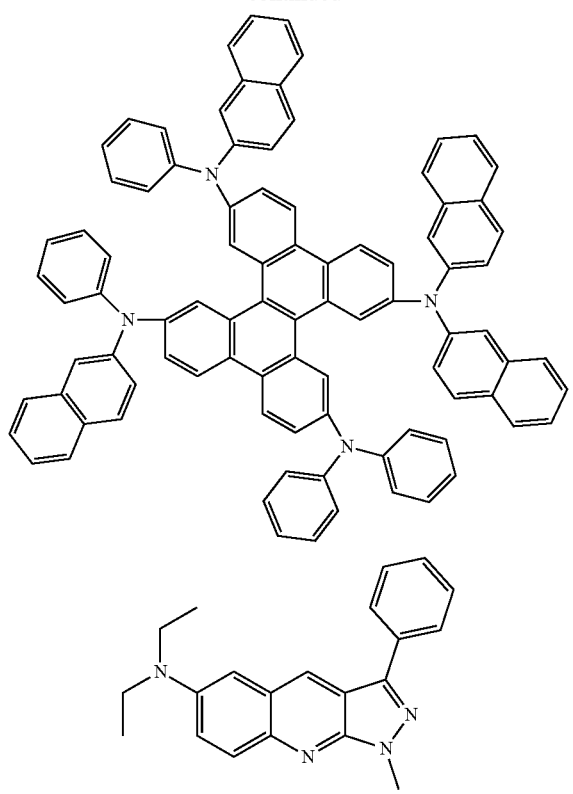

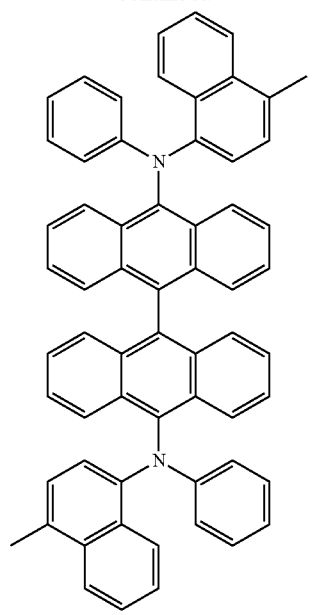

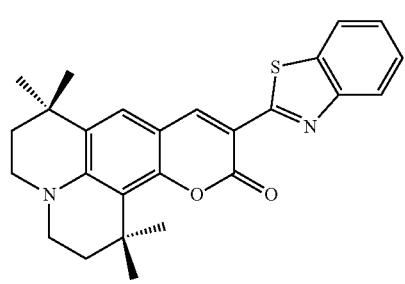

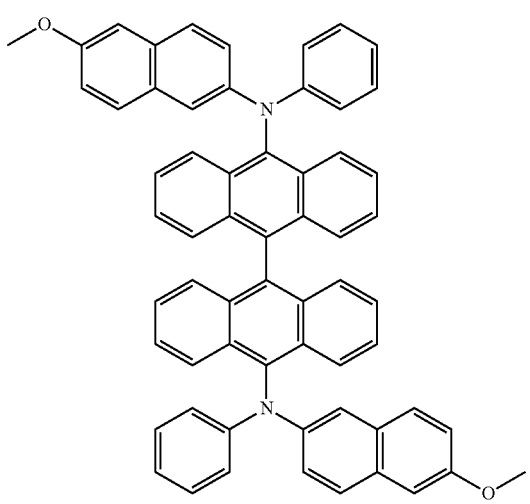

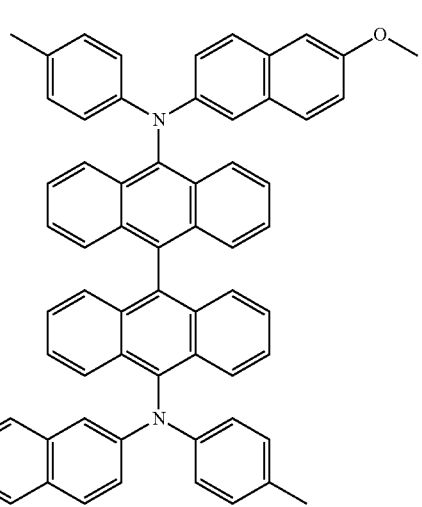

In a further embodiment of the invention, the composition has an emission peak in the visible or nearest ultraviolet range, i.e. in the range of a wavelength of from 380 to 800 nm, in particular between 485 nm and 590 nm, preferably between 505 nm and 565 nm, even more preferably between 515 nm and 545 nm.

Composition Wherein the at Least One Further Emitter Molecule F is a Red Fluorescence Emitter In a further embodiment of the invention, the at least one further emitter molecule F is a fluorescence emitter, in particular a red fluorescence emitter.

In one embodiment, the at least one further emitter molecule F is a fluorescence emitter selected from the following group:
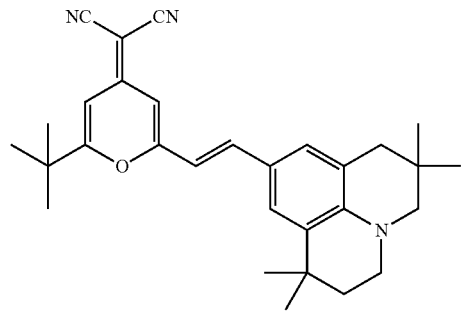
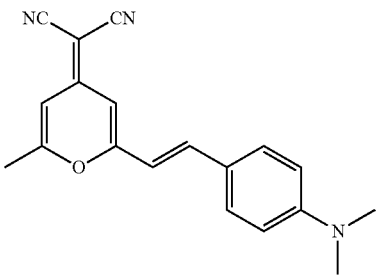
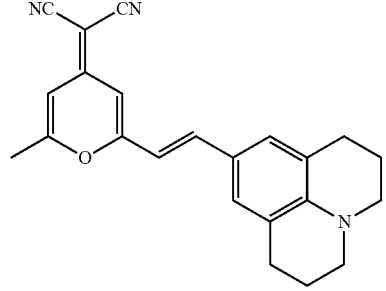
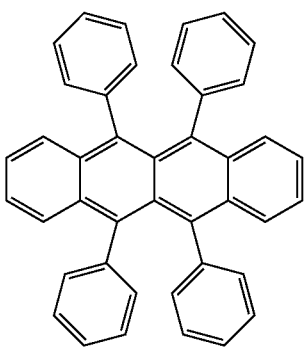
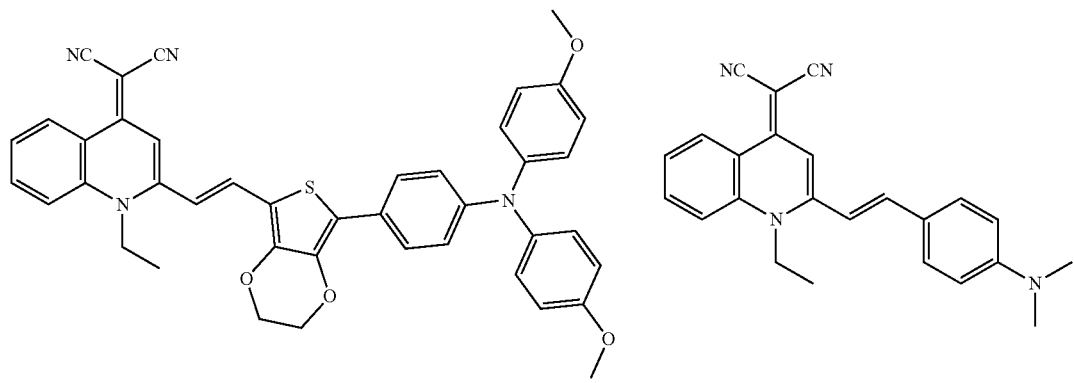
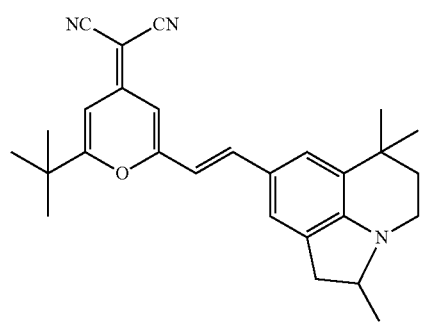
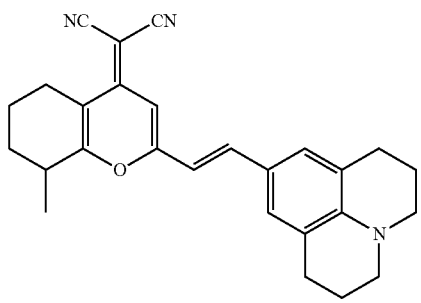

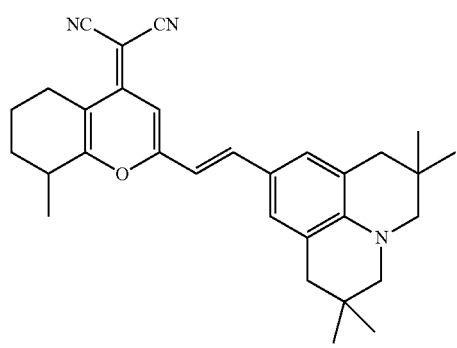
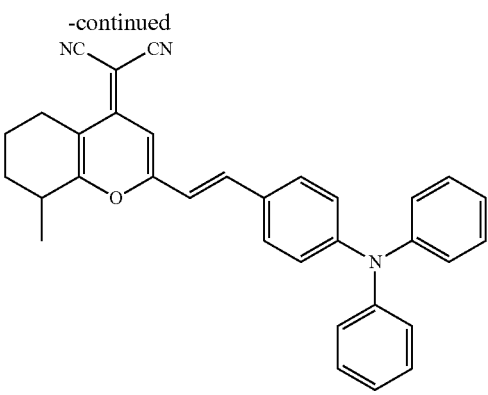
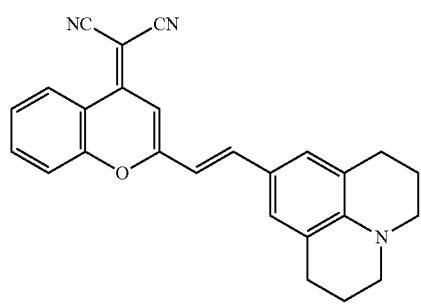
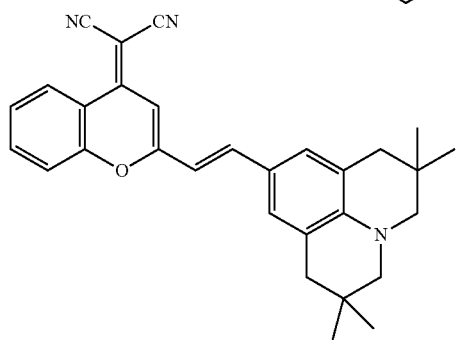
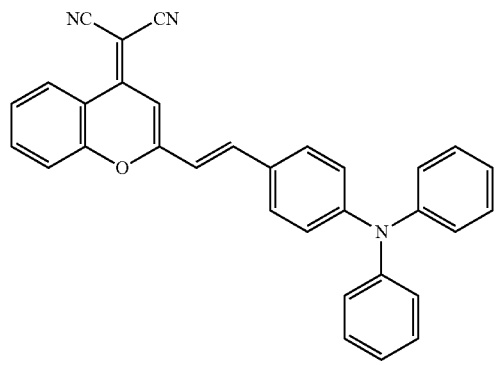
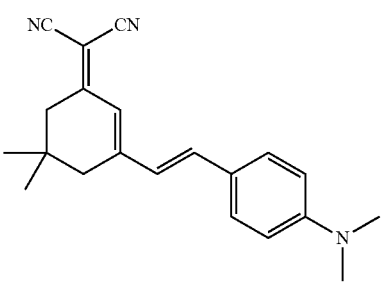
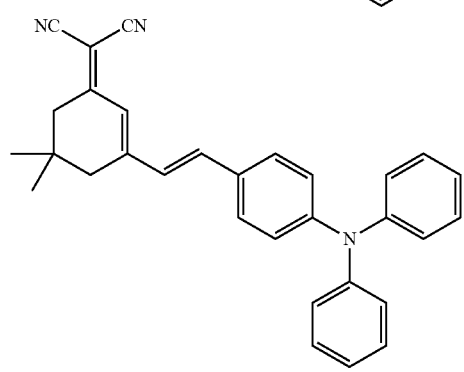
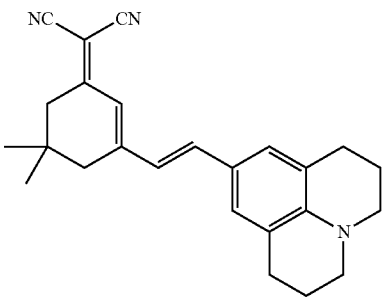
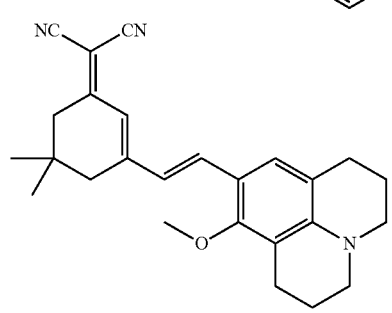
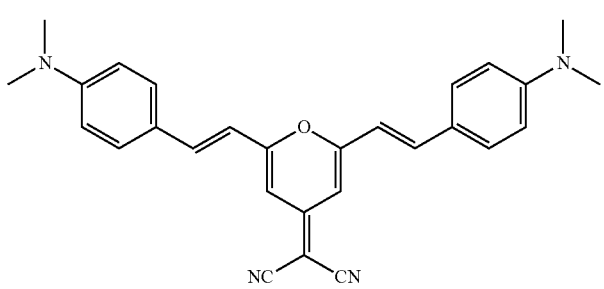

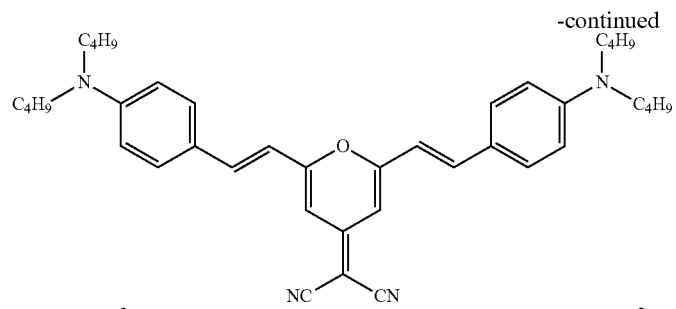
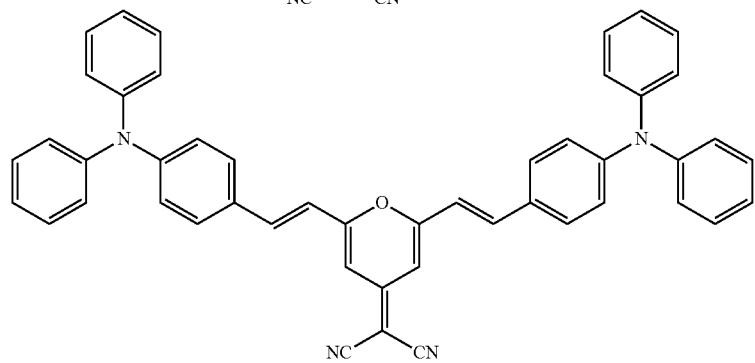
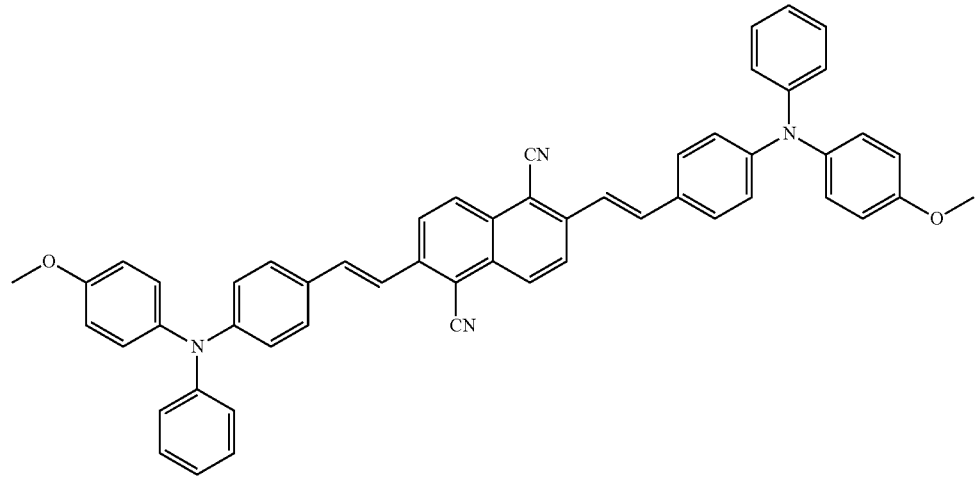
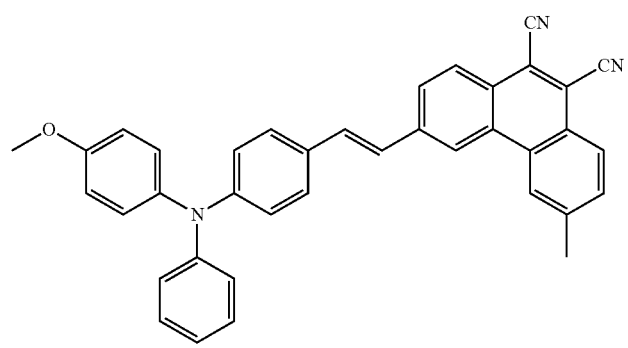

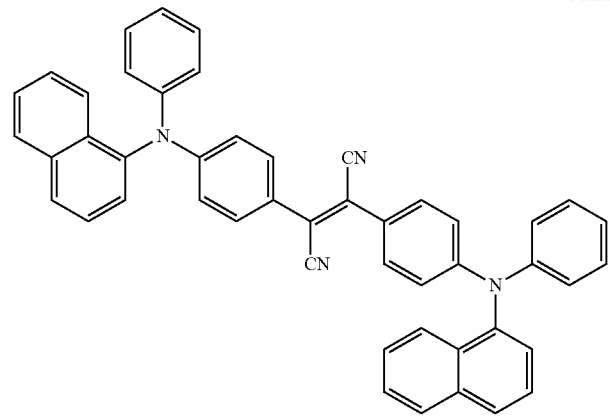
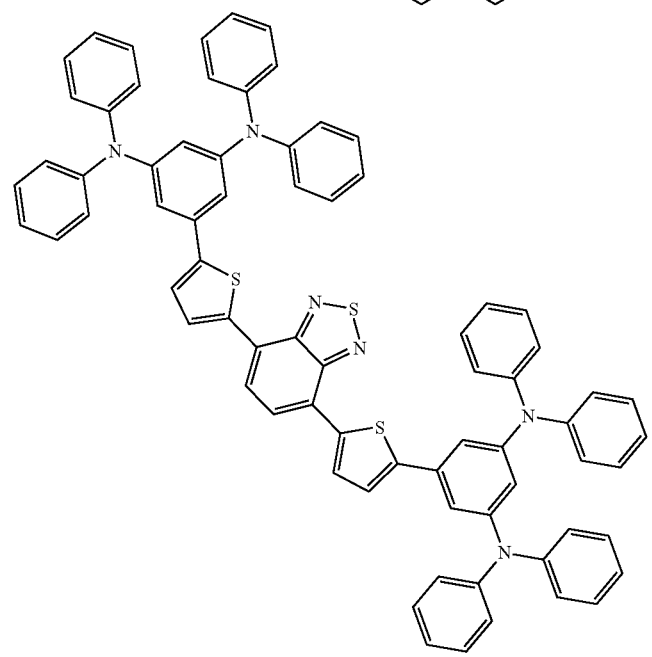
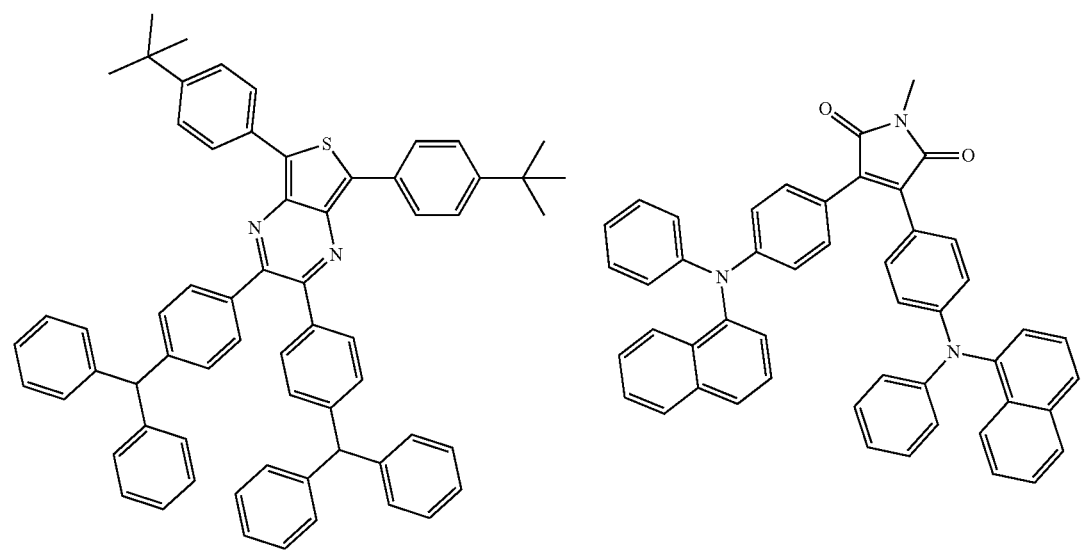

-continued
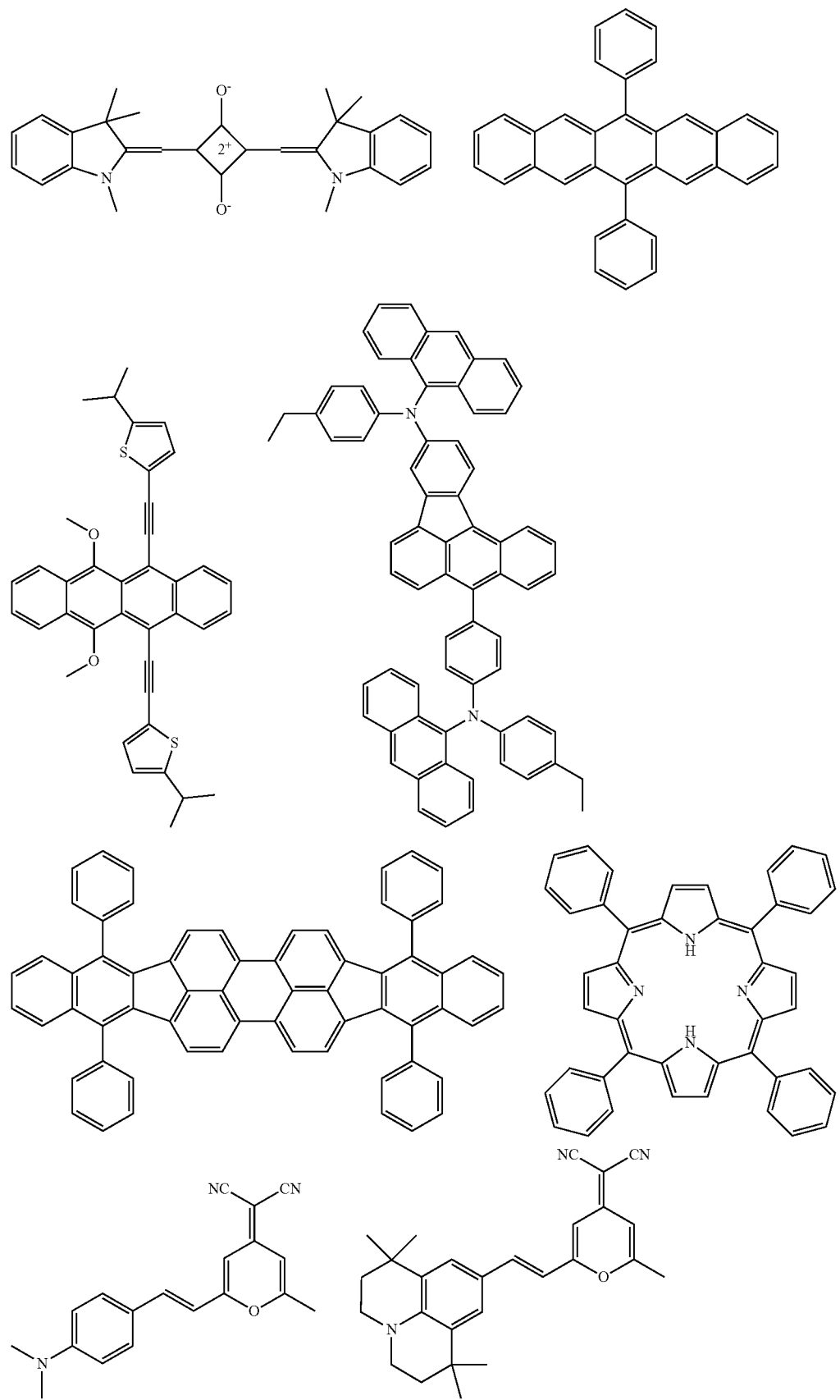

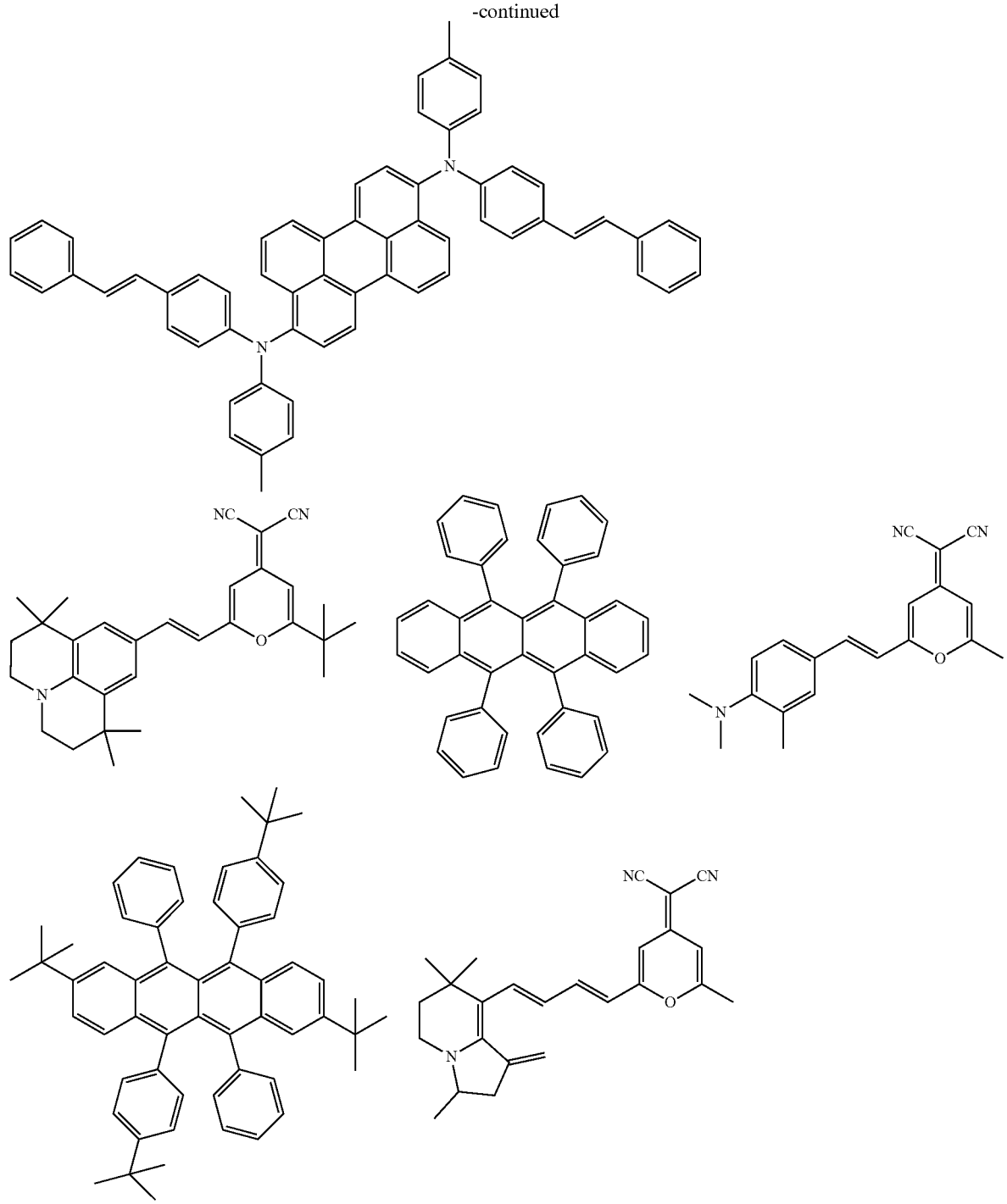

In a further embodiment of the invention, the composition has an emission peak in the visible or nearest ultraviolet range, i.e. in the range of a wavelength of from 380 nm to 800 nm, in particular between 590 nm and 690 nm, preferably between 610 nm and 665 nm, even more preferably between 620 nm and 640 nm.

Light-Emitting Layer EML

In one embodiment, the light-emitting layer EML of an organic light-emitting diode of the invention comprises (or essentially consists of) a composition comprising or consisting of:

(i) 1-50% by weight, preferably 5-40% by weight, in particular 10-30% by weight, of one or more organic molecules according to the invention;
(ii) 5-99% by weight, preferably 30-94.9% by weight, in particular 40-89% by weight, of at least one host compound H; and
(iii) optionally 0-94% by weight, preferably 0.1-65% by weight, in particular 1-50% by weight, of at least one further host compound D with a structure differing from the structure of the molecules according to the invention; and (iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules of the invention, in particular transferred from the first excited triplet state T1(H) of the host compound H to the first excited triplet state T1(E) of the one or more organic molecules according to the invention and/or from the first excited singlet state S1(H) of the host compound H to the first excited singlet state S1(E) of the one or more organic molecules according to the invention.

In one embodiment, the host compound H has a highest occupied molecular orbital HOMO(H) having an energy $E^{HOMO}(H)$ in the range of from −5 eV to −6.5 eV and one organic molecule according to the invention E has a highest occupied molecular orbital HOMO(E) having an energy $E^{HOMO}(E)$, wherein $E^{HOMO}(H) > E^{HOMO}(E)$.

In a further embodiment, the host compound H has a lowest unoccupied molecular orbital LUMO(H) having an energy $E^{LUMO}(H)$ and the one organic molecule according to the invention E has a lowest unoccupied molecular orbital LUMO(E) having an energy $E^{LUMO}(E)$, wherein $E^{LUMO}(H) > E^{LUMO}(E)$.

Light-Emitting Layer EML Comprising at Least One Further Host Compound D

In a further embodiment, the light-emitting layer EML of an organic light-emitting diode of the invention comprises (or essentially consists of) a composition comprising or consisting of:
(i) 1-50% by weight, preferably 5-40% by weight, in particular 10-30% by weight, of one organic molecule according to the invention;
(ii) 5-99% by weight, preferably 30-94.9% by weight, in particular 40-89% by weight, of one host compound H; and
(iii) 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

In one embodiment of the organic light-emitting diode of the invention, the host compound H has a highest occupied molecular orbital HOMO(H) having an energy $E^{HOMO}(H)$ in the range of from −5 eV to −6.5 eV and the at least one further host compound D has a highest occupied molecular orbital HOMO(D) having an energy $E^{HOMO}(D)$, wherein $E^{HOMO}(H) > E^{HOMO}(D)$. The relation $E^{HOMO}(H) > E^{HOMO}(D)$ favors an efficient hole transport.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H) > E^{LUMO}(D)$. The relation $E^{LUMO}(H) > E^{LUMO}(D)$ favors an efficient electron transport.

In one embodiment of the organic light-emitting diode of the invention, the host compound H has a highest occupied molecular orbital HOMO(H) having an energy $E^{HOMO}(H)$ and a lowest unoccupied molecular orbital LUMO(H) having an energy $E^{LUMO}(H)$, and the at least one further host compound D has a highest occupied molecular orbital HOMO(D) having an energy $E^{HOMO}(D)$ and a lowest unoccupied molecular orbital LUMO(D) having an energy $E^{LUMO}(D)$, the organic molecule E of the invention has a highest occupied molecular orbital HOMO(E) having an energy $E^{HOMO}(E)$ and a lowest unoccupied molecular orbital LUMO(E) having an energy $E^{LUMO}(E)$, wherein
$E^{HOMO}(H) > E^{HOMO}(D)$ and the difference between the energy level of the highest occupied molecular orbital HOMO(E) of organic molecule according to the invention ($E^{HOMO}(E)$) and the energy level of the highest occupied molecular orbital HOMO(H) of the host compound H ($E^{HOMO}(H)$) is between 0.5 eV and 0.5 eV, more preferably between −0.3 eV and 0.3 eV, even more preferably between −0.2 eV and 0.2 eV or even between −0.1 eV and 0.1 eV; and $E^{LUMO}(H) > E^{LUMO}(D)$ and the difference between the energy level of the lowest unoccupied molecular orbital LUMO(E) of organic molecule according to the invention ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

Light-Emitting Layer EML Comprising at Least One Further Emitter Molecule F

In a further embodiment, the light-emitting layer EML comprises (or (essentially) consists of) a composition comprising or consisting of:
(i) 1-50% by weight, preferably 5-40% by weight, in particular 10-30% by weight, of one organic molecule according to the invention;
(ii) 5-98% by weight, preferably 30-93.9% by weight, in particular 40-88% by weight, of one host compound H;
(iii) 1-30% by weight, in particular 1-20% by weight, preferably 1-5% by weight, of at least one further emitter molecule F with a structure differing from the structure of the molecules according to the invention; and
(iv) optionally 0-94% by weight, preferably 0.1-65% by weight, in particular 1-50% by weight, of at least one further host compound D with a structure differing from the structure of the molecules according to the invention; and
(v) optionally 0-94% by weight, preferably 0-65% by weight, in particular 0-50% by weight, of a solvent.

In a further embodiment, the light-emitting layer EML comprises (or (essentially) consists of) a composition as described in Compositions with at least one further emitter, with the at least one further emitter molecule F as defined in Composition wherein the at least one further emitter molecule F is a green fluorescence emitter.

In a further embodiment, the light-emitting layer EML comprises (or (essentially) consists of) a composition as described in Compositions with at least one further emitter, with the at least one further emitter molecule F as defined in Composition wherein the at least one further emitter molecule F is a red fluorescence emitter.

In one embodiment of the light-emitting layer EML comprising at least one further emitter molecule F, energy can be transferred from the one or more organic molecules of the invention E to the at least one further emitter molecule F, in particular transferred from the first excited singlet state S1(E) of one or more organic molecules of the invention E to the first excited singlet state S1(F) of the at least one further emitter molecule F.

In one embodiment, the first excited singlet state S1(H) of one host compound H of the light-emitting layer is higher in energy than the first excited singlet state S1(E) of the one or more organic molecules of the invention E: S1(H)>S1(E), and the first excited singlet state S1(H) of one host compound H is higher in energy than the first excited singlet state S1(F) of the at least one emitter molecule F: S1(H)>S1(F).

In one embodiment, the first excited triplet state T1(H) of one host compound H is higher in energy than the first excited triplet state T1 (E) of the one or more organic molecules of the invention E: T1(H)>T1(E), and the first excited triplet state T1(H) of one host compound H is higher in energy than the first excited triplet state T1(F) of the at least one emitter molecule F: T1(H)>T1(F).

In one embodiment, the first excited singlet state S1(E) of the one or more organic molecules of the invention E is higher in energy than the first excited singlet state S1(F) of the at least one emitter molecule F: S1(E)>S1(F).

In one embodiment, the first excited triplet state T1(E) of the one or more organic molecules E of the invention is higher in energy than the first excited singlet state T1(F) of the at least one emitter molecule F: T1(E)>T1(F).

In one embodiment, the first excited triplet state T1(E) of the one or more organic molecules of the invention E is higher in energy than the first excited singlet state T1(F) of the at least one emitter molecule F: T1(E)>T1(F), wherein the absolute value of the energy difference between T1(E) and T1(F) is larger than 0.3 eV, preferably larger than 0.4 eV, or even larger than 0.5 eV.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and the one organic molecule according to the invention E has a highest occupied molecular orbital HOMO(E) having an energy $E^{HOMO}(E)$ and a lowest unoccupied molecular orbital LUMO(E) having an energy $E^{LUMO}(E)$, the at least one further emitter molecule F has a highest occupied molecular orbital HOMO(F) having an energy $E^{HOMO}(F)$ and a lowest unoccupied molecular orbital LUMO(E) having an energy $E^{LUMO}(F)$, wherein $E^{HOMO}(H)>E^{HOMO}(E)$ and the difference between the energy level of the highest occupied molecular orbital HOMO(F) of the at least one further emitter molecule ($E^{HOMO}(F)$) and the energy level of the highest occupied molecular orbital HOMO(H) of the host compound H ($E^{HOMO}(H)$) is between 0.5 eV and 0.5 eV, more preferably between −0.3 eV and 0.3 eV, even more preferably between −0.2 eV and 0.2 eV or even between −0.1 eV and 0.1 eV; and $E^{LUMO}(H)>E^{LUMO}(E)$ and the difference between the energy level of the lowest unoccupied molecular orbital LUMO(F) of the at least one further emitter molecule ($E^{LUMO}(F)$) and the lowest unoccupied molecular orbital LUMO(E) of the one organic molecule according to the invention ($E^{LUMO}(E)$) is between −0.5 eV and 0.5 eV, more preferably between −0.3 eV and 0.3 eV, even more preferably between −0.2 eV and 0.2 eV or even between −0.1 eV and 0.1 eV.

Optoelectronic Devices

In a further aspect, the invention relates to an optoelectronic device comprising an organic molecule or a composition as described herein, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the optoelectronic device is a device selected from the group consisting of an organic light emitting diode (OLED), a light emitting electrochemical cell (LEC), and a light-emitting transistor.

In one embodiment of the optoelectronic device of the invention, the organic molecule according to the invention is used as emission material in a light-emitting layer EML.

In one embodiment of the optoelectronic device of the invention, the light-emitting layer EML consists of the composition according to the invention described herein.

When the optoelectronic device is an OLED, it may, for example, exhibit the following layer structure:
1. substrate
2. anode layer A
3. hole injection layer, HIL
4. hole transport layer, HTL
5. electron blocking layer, EBL
6. emitting layer, EML
7. hole blocking layer, HBL
8. electron transport layer, ETL
9. electron injection layer, EIL
10. cathode layer, wherein the OLED comprises each layer only optionally, different layers may be merged and the OLED may comprise more than one layer of each layer type defined above.

Furthermore, the optoelectronic device may optionally comprise one or more protective layers protecting the device from damaging exposure to harmful species in the environment including, exemplarily moisture, vapor and/or gases.

In one embodiment of the invention, the optoelectronic device is an OLED, which exhibits the following inverted layer structure:
1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A wherein the OLED with an inverted layer structure comprises each layer only optionally, different layers may be merged and the OLED may comprise more than one layer of each layer types defined above.

In one embodiment of the invention, the optoelectronic device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the anode layer.

In one embodiment of the invention, the optoelectronic device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The anode layer A is mostly composed of materials allowing to obtain an (essentially) transparent film. As at least one of both electrodes should be (essentially) transparent in order to allow light emission from the OLED, either the anode layer A or the cathode layer C is transparent. Preferably, the anode layer A comprises a large content or even consists of transparent conductive oxides (TCOs). Such anode layer A may exemplarily comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

Preferably, the anode layer A (essentially) consists of indium tin oxide (ITO) (e.g., (InO3)0.9(SnO2)0.1). The roughness of the anode layer A caused by the transparent conductive oxides (TCOs) may be compensated by using a hole injection layer (HIL). Further, the HIL may facilitate the injection of quasi charge carriers (i.e. holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may exemplarily comprise PEDOT:PSS (poly-3,4-ethylendioxy thiophene: polystyrene sulfonate), PEDOT (poly-3,4-ethylendioxy thiophene), mMTDATA (4,4',4''-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB(N,N'-nis-(1-naphthalenyl)-N,N'-bis-phenyl-(1,1'-biphenyl)-4,4'-diamine), NPNPB(N,N'-diphenyl-N,N'-di-[4-(N,N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL) typically a hole transport layer (HTL) is located. Herein, any hole transport compound may be used. Exemplarily, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. Exemplarily the hole transport layer (HTL) may comprise a star-shaped heterocycle such as tris(4-carbazoyl-9-ylphenyl)amine (TCTA), poly-TPD (poly(4-butylphenyl-diphenylamine)), [alpha]-NPD (poly(4-butylphenyl-diphenyl-amine)), TAPC (4,4'-cyclohexyliden-bis[N,N-bis(4-methylphenyl)benze-namine]), 2-TNATA (4,4',4''-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane (F4-TCNQ), copper-pentafluorobenzoate (Cu(I)pFBz) or transition metal complexes may exemplarily be used as organic dopant.

The EBL may exemplarily comprise mCP (1,3-bis(carbazol-9-yl)benzene), TCTA, 2-TNATA, mCBP (3,3-di(9H-carbazol-9-yl)biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), typically, the light-emitting layer EML is located. The light-emitting layer EML comprises at least one light emitting molecule. Particular, the EML comprises at least one light emitting molecule according to the invention. Typically, the EML additionally comprises one or more host material. Exemplarily, the host material is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino)phenyl]ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting molecule species according to the invention and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)

phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML an electron transport layer (ETL) may be located. Herein, any electron transporter may be used. Exemplarily, compounds poor of electrons such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a holeblocking layer (HBL) is introduced.

The HBL may, for example, comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris(carbazol)-9-yl)benzene).

A cathode layer C may be located adjacent to the electron transport layer (ETL). For example, the cathode layer C may comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of (essentially) non-transparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), $Li_2O$, $BaF_2$, MgO and/or NaF.

Optionally, also the electron transport layer (ETL) and/or a hole blocking layer (HBL) may comprise one or more host compounds.

In order to modify the emission spectrum and/or the absorption spectrum of the light-emitting layer EML further, the light-emitting layer EML may further comprise one or more further emitter molecule F. Such an emitter molecule F may be any emitter molecule known in the art. Preferably such an emitter molecule F is a molecule with a structure differing from the structure of the molecules according to the invention. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. For example, the triplet and/or singlet excitons may be transferred from the emitter molecule according to the invention to the emitter molecule F before relaxing to the ground state S0 by emitting light typically red-shifted in comparison to the light emitted by emitter molecule E. Optionally, the emitter molecule F may also provoke two-photon effects (i.e. the absorption of two photons of half the energy of the absorption maximum).

Optionally, an optoelectronic device (e.g., an OLED) may, for example, be an essentially white optoelectronic device. Exemplarily such white optoelectronic device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:
  violet: wavelength range of >380-420 nm;
  deep blue: wavelength range of >420-480 nm;
  sky blue: wavelength range of >480-500 nm;
  green: wavelength range of >500-560 nm;
  yellow: wavelength range of >560-580 nm;
  orange: wavelength range of >580-620 nm;
  red: wavelength range of >620-800 nm.

With respect to emitter molecules, such colors refer to the emission maximum. Therefore, exemplarily, a deep blue emitter has an emission maximum in the range of from >420 to 480 nm, a sky-blue emitter has an emission maximum in the range of from >480 to 500 nm, a green emitter has an emission maximum in a range of from >500 to 560 nm, a red emitter has an emission maximum in a range of from >620 to 800 nm.

A further embodiment of the present invention relates to an OLED, which emits light with CIEx and CIEy color coordinates close to the CIEx (=0.170) and CIEy (=0.797) color coordinates of the primary color green (CIEx=0.170 and CIEy=0.797) as defined by ITU-R Recommendation BT.2020 (Rec. 2020) and thus is suited for the use in Ultra High Definition (UHD) displays, e.g. UHD-TVs. In this context, the term "close to" refers to the ranges of CIEx and CIEy coordinates provided at the end of this paragraph. In commercial applications, typically top-emitting (top-electrode is transparent) devices are used, whereas test devices as used throughout the present application represent bottom-emitting devices (bottom-electrode and substrate are transparent). Accordingly, a further aspect of the present invention relates to an OLED, whose emission exhibits a CIEx color coordinate of between
  0.06 and 0.34, preferably between 0.07 and 0.29, more preferably between 0.09 and 0.24 or even more preferably between 0.12 and 0.22 or even between 0.14 and 0.19 and/or a CIEy color coordinate of between 0.75 and 1.20, preferably between 0.76 and 1.05, more preferably between 0.77 and 0.95 or even more preferably between 0.78 and 0.90 or even between 0.79 and 0.85.

A further embodiment of the present invention relates to an OLED, which emits light with CIEx and CIEy color coordinates close to the CIEx (=0.708) and CIEy (=0.292) color coordinates of the primary color red (CIEx=0.708 and CIEy=0.292) as defined by ITU-R Recommendation BT.2020 (Rec. 2020) and thus is suited for the use in Ultra High Definition (UHD) displays, e.g. UHD-TVs. In this context, the term "close to" refers to the ranges of CIEx and CIEy coordinates provided at the end of this paragraph. In commercial applications, typically top-emitting (top-electrode is transparent) devices are used, whereas test devices as used throughout the present application represent bottom-emitting devices (bottom-electrode and substrate are transparent). Accordingly, a further aspect of the present invention relates to an OLED, whose emission exhibits a CIEx color coordinate of between 0.60 and 0.88, preferably between 0.61 and 0.83, more preferably between 0.63 and 0.78 or even more preferably between 0.66 and 0.76 or even between 0.68 and 0.73 and/or a CIEy color coordinate of between 0.25 and 0.70, preferably between 0.26 and 0.55, more preferably between 0.27 and 0.45 or even more preferably between 0.28 and 0.40 or even between 0.29 and 0.35.

Accordingly, a further aspect of the present invention relates to an OLED, which exhibits an external quantum efficiency at 1000 cd/m$^2$ of more than 10%, more preferably of more than 13%, more preferably of more than 15%, even more preferably of more than 17% or even more than 20% and/or exhibits an emission maximum between 495 nm and 580 nm, preferably between 500 nm and 560 nm, more preferably between 510 nm and 540 nm, even more preferably between 515 nm and 535 nm and/or exhibits a LT80 value at 500 cd/m$^2$ of more than 1000 h, preferably more than 2500 h, more preferably more than 5000 h, even more preferably more than 7500 h or even more than 10000 h.

The optoelectronic device, in particular the OLED according to the present invention can be manufactured by any means of vapor deposition and/or liquid processing. Accordingly, at least one layer is
- prepared by means of a sublimation process,
- prepared by means of an organic vapor phase deposition process,
- prepared by means of a carrier gas sublimation process, solution processed or
- printed.

The methods used to manufacture the optoelectronic device, in particular the OLED according to the present invention are known in the art. The different layers are individually and successively deposited on a suitable substrate by means of subsequent deposition processes. The individual layers may be deposited using the same or differing deposition methods.

Vapor deposition processes exemplarily comprise thermal (co)evaporation, chemical vapor deposition and physical vapor deposition. For active matrix OLED display, an AMO-LED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

General Synthesis Scheme

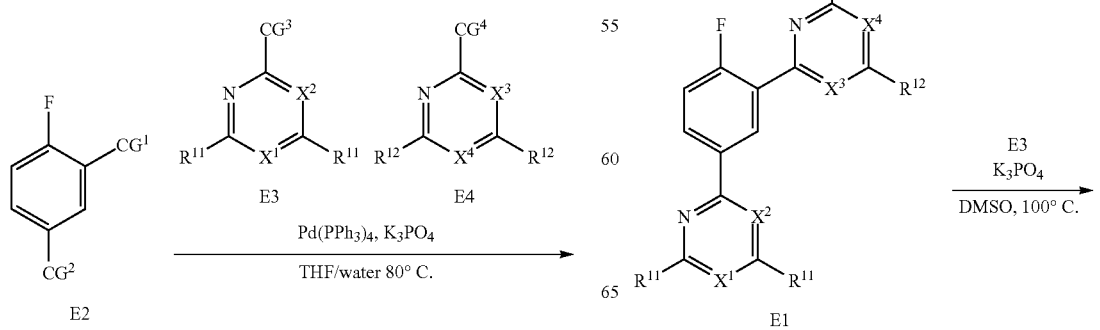

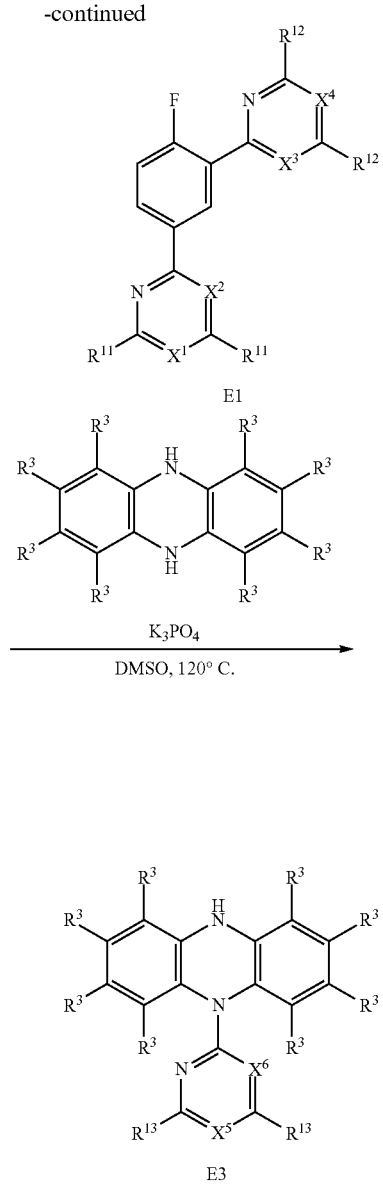

-continued

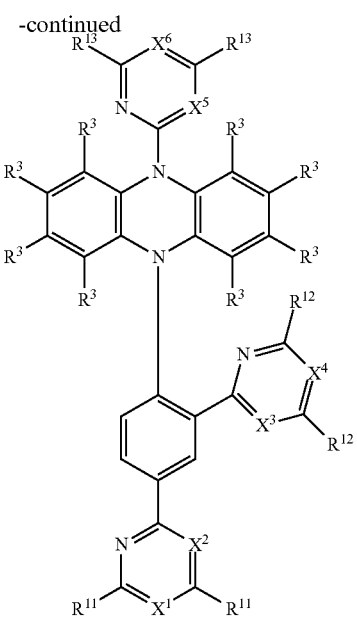

General Procedure for Synthesis AAV1:

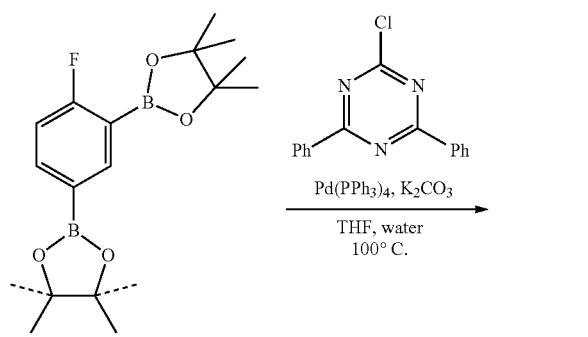

2-Fluorophenyl-1,4-diboronic acid pinacol ester (1.00 equivalents), 2-chloro-4,6-diphenyl-1,3,5-triazine (2.50 equivalents), tetrakis(triphenylphosphine)palladium(0) (0.12 equivalent), and tribasic potassium phosphate (6.00 equivalents) are stirred under nitrogen atmosphere in a tetrahydrofuran (THF)/water mixture (ratio of 3:1) at 100° C. for 16 hours. After cooling down to room temperature (rt), the reaction mixture is poured into water, the product is filtered and washed with ethanol (EtOH).

General Procedure for Synthesis AAV2:

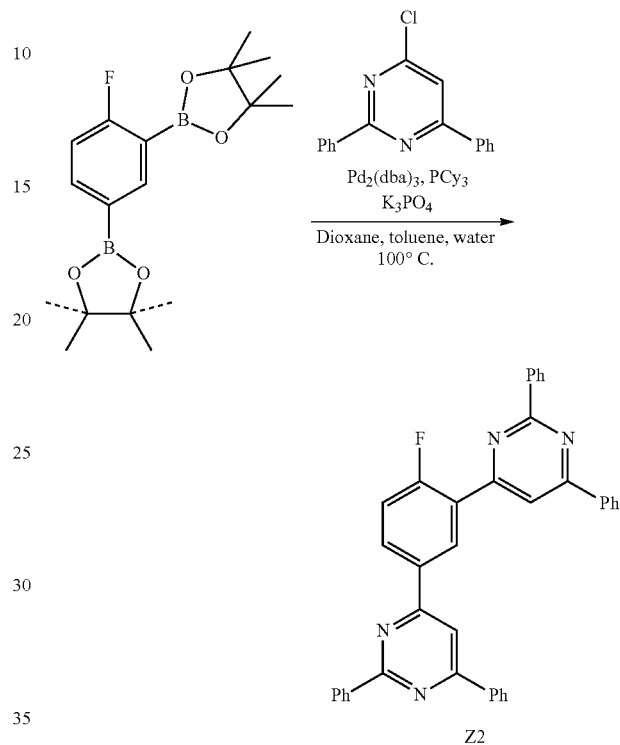

2-Fluorophenyl-1,4-diboronic acid pinacol ester (1.00 equivalent), 4-chloro-2,6-diphenyl-1,3-pyrimidine (2.25 equivalents), Pd$_2$(dba)$_3$ (0.06 equivalents), tricyclohexylphosphine (PCy$_3$, 0.14 equivalents), and tribasic potassium phosphate (6.00 equivalents) are stirred under nitrogen atmosphere in a dioxane/toluene/water mixture (ratio: 3:1:1) at 100° C. overnight. After cooling down to room temperature (rt), the reaction mixture is poured into water, the product is filtered and washed with EtOH.

General Procedure for Synthesis AAV3:

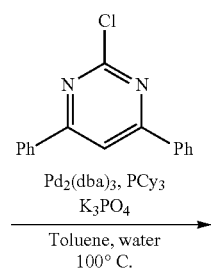

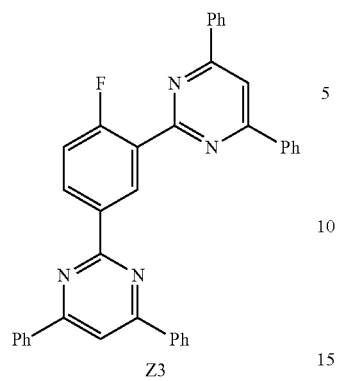

Z3

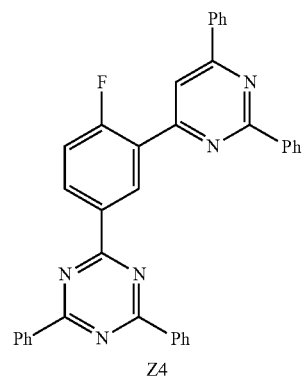

Z4

The synthesis of Z3 is carried out according to AAV2, wherein 2-fluorophenyl-1,4-diboronic acid pinacol ester reacts with 2-chloro-4,6-diphenyl-1,3-pyrimidine.

General Procedure for Synthesis AAV4:

3-Chloro-4-fluorophenyl-boronic acid pinacol ester (1.00 equivalent) is reacted with 2-chloro-4,6-diphenyl-1,3,5-triazine (1.25 equivalents) to yield intermediate I1 employing similar conditions as in AAV1. Subsequently, the intermediate I1 (1.00 equivalent) is reacted with 2,6-diphenyl-1,3-pyrimidine-4-boronic acid pinacol ester (1.10 equivalents) employing similar conditions as in AAV2 to yield Z4.

General Procedure for Synthesis AAV4-2:

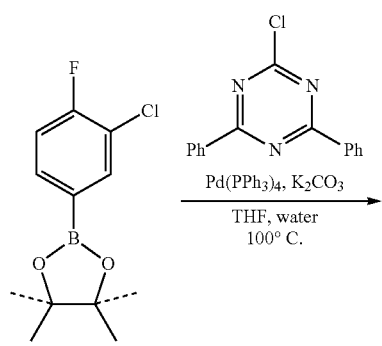

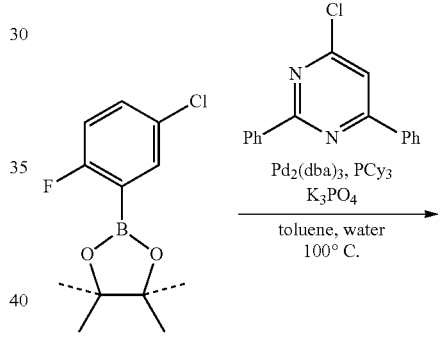

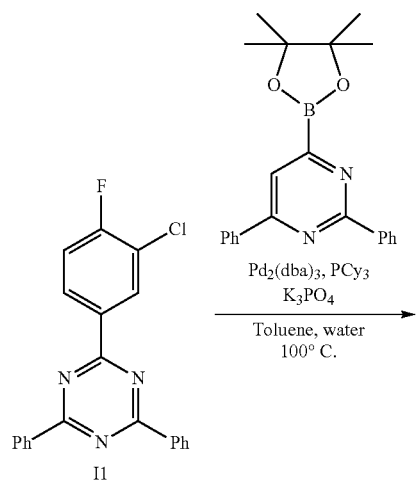

I1

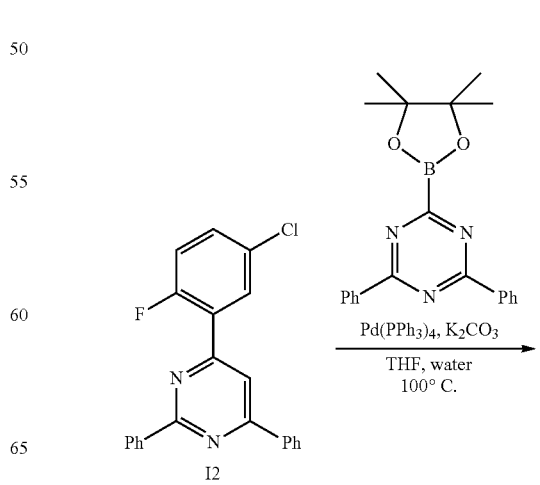

I2

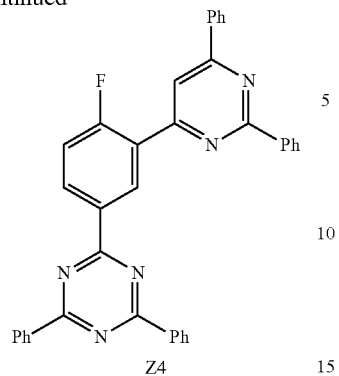

Z4

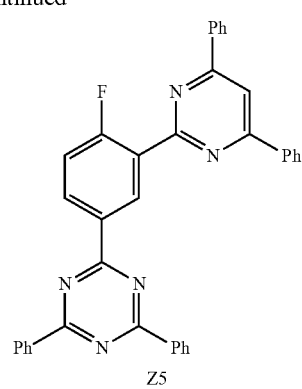

Z5

5-Chloro-2-fluorophenyl-boronic acid pinacol ester (1.00 equivalent) is reacted with 4-chloro-2,6-diphenyl-1,3-pyrimidine (1.10 equivalents) to yield intermediate I2 employing similar conditions as in AAV2. Subsequently the intermediate I2 (1.00 equivalent) is reacted with 4,6-diphenyl-1,3,5-triazine-2-boronic acid pinacol ester (1.25 equivalents) employing similar conditions as in AAV1 to yield Z4.

General Procedure for Synthesis AAV5:

3-Chloro-4-fluorophenyl-boronic acid pinacol ester (1.00 equivalent) is reacted with 2-chloro-4,6-diphenyl-1,3,5-triazine (1.25 equivalents) to yield intermediate I1 employing similar conditions as in AAV1. Subsequently, the intermediate I1 (1.00 equivalent) is reacted with 4,6-diphenyl-1,3-pyrimidine-2-boronic acid pinacol ester (1.10 equivalents) employing similar conditions as in AAV3 to yield Z5.

General Procedure for Synthesis AAV5-2:

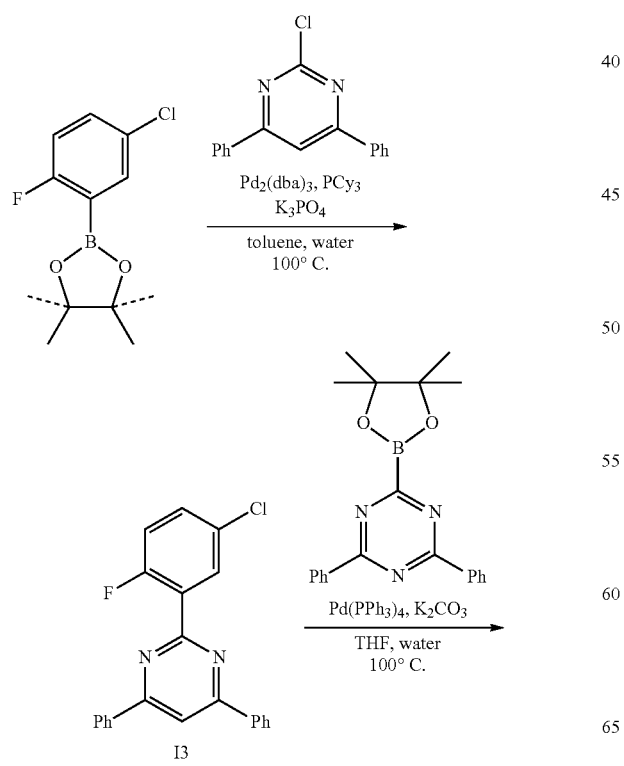

5-Chloro-2-fluorophenyl-boronic acid pinacol ester (1.00 equivalent) is reacted with 2-chloro-4,6-diphenyl-1,3-pyrimidine (1.10 equivalents) to yield intermediate I3 employing similar conditions as in AAV3. Subsequently, the intermediate I3 (1.00 equivalent) is reacted with 4,6-diphenyl-1,3,5-triazine-2-boronic acid pinacol ester (1.25 equivalents) employing similar conditions as in AAV1.

General Procedure for Synthesis AAV6:

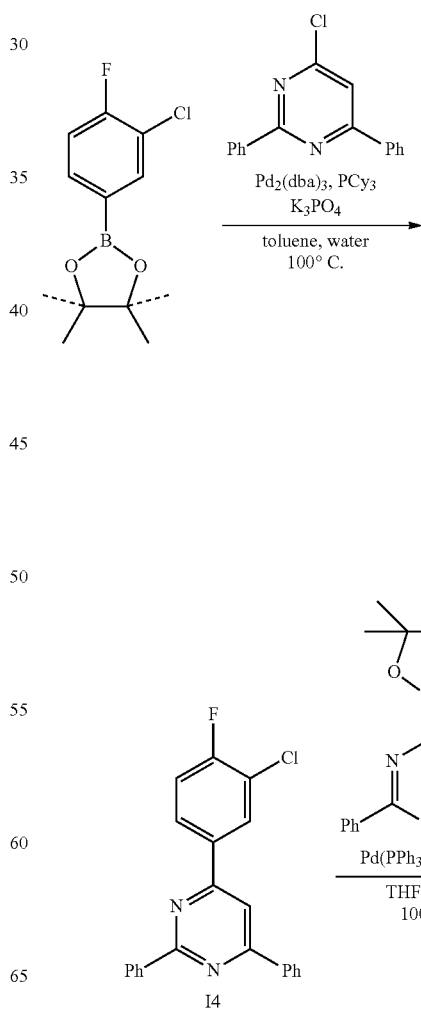

-continued

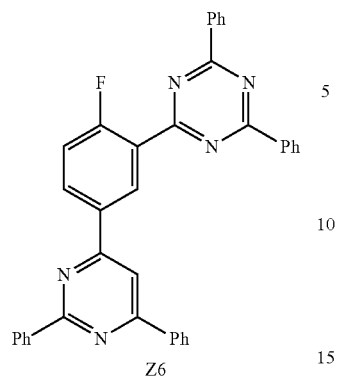

Z6

-continued

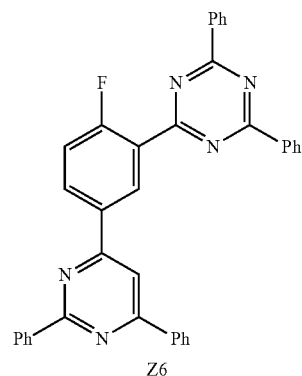

Z6

3-Chloro-4-fluorophenyl-boronic acid pinacol ester (1.00 equivalent) is reacted with 4-chloro-2,6-diphenyl-1,3-pyrimidine (1.10 equivalents) to yield intermediate I4 employing similar conditions as in AAV2. Subsequently the intermediate I4 (1.00 equivalent) is reacted with 4,6-diphenyl-1,3,5-triazine-2-boronic acid pinacol ester (1.25 equivalents) employing similar conditions as in AAV1 to yield Z6.

General Procedure for Synthesis AAV6-2:

5-Chloro-2-fluorophenyl-boronic acid pinacol ester (1.00 equivalent) is reacted with 2-chloro-4,6-diphenyl-1,3,5-triazine (1.25 equivalents) to yield intermediate I5 employing similar conditions as in AAV1. Subsequently the intermediate I5 (1.00 equivalent) is reacted with 2,6-diphenyl-1,3-pyrimidine-4-boronic acid pinacol ester (1.10 equivalents) employing similar conditions as in AAV2 to yield Z6.

General Procedure for Synthesis AAV7:

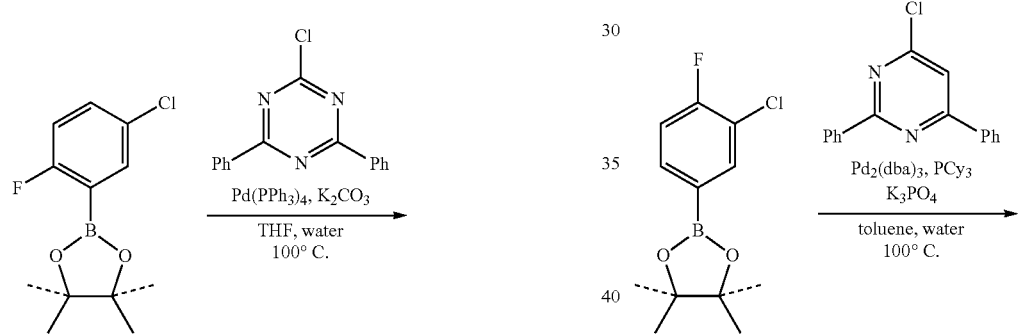

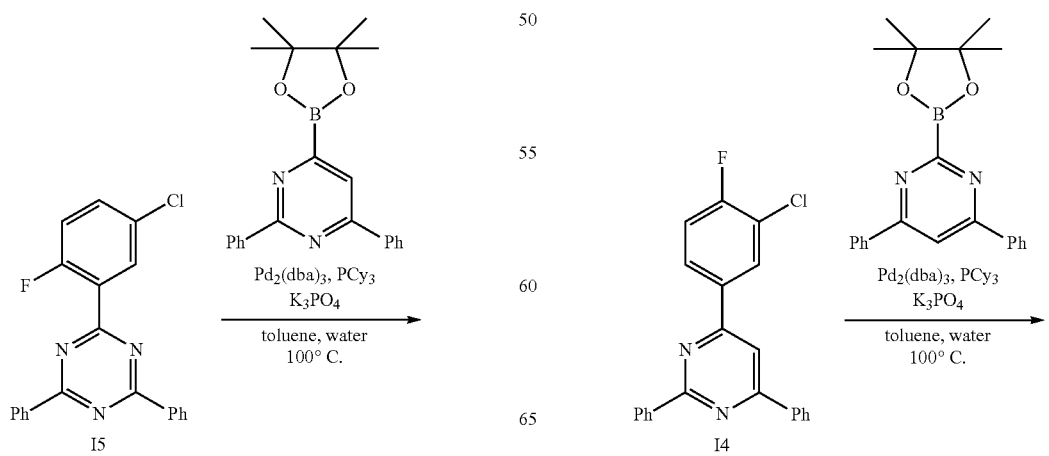

-continued

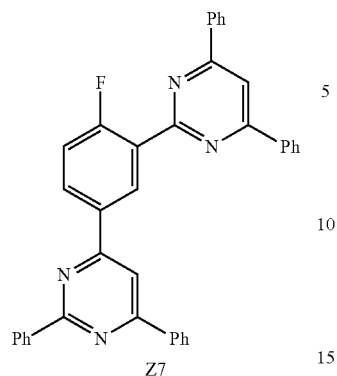

Z7

3-Chloro-4-fluorophenyl-boronic acid pinacol ester (1.00 equivalent) is reacted with 4-chloro-2,6-diphenyl-1,3-pyrimidine (1.10 equivalents) to yield intermediate I4 employing similar conditions as in AAV2. Subsequently the intermediate I4 (1.00 equivalent) is reacted with 4,6-diphenyl-1,3-pyrimidine-2-boronic acid pinacol ester (1.10 equivalents) employing similar conditions as in AAV3 to yield Z7.

General Procedure for Synthesis AAV7-2:

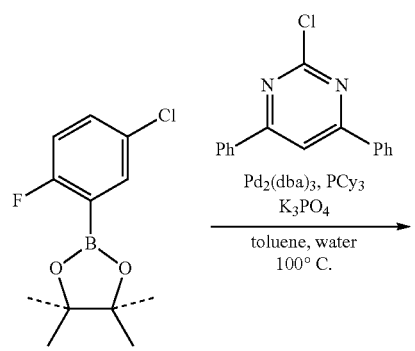

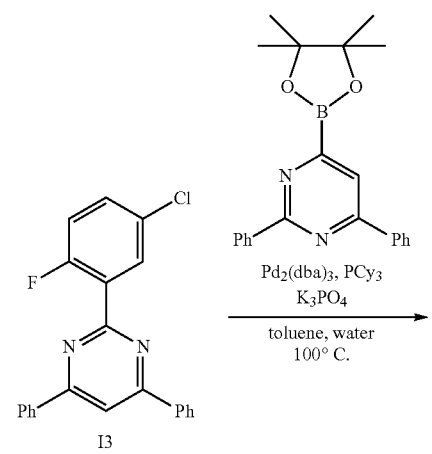

I3

-continued

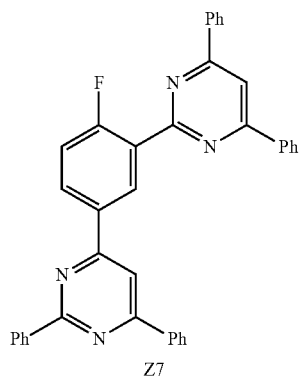

Z7

5-Chloro-2-fluorophenyl-boronic acid pinacol ester (1.00 equivalent) is reacted with 2-chloro-4,6-diphenyl-1,3-pyrimidine (1.10 equivalents) to yield intermediate I3 employing similar conditions as in AAV3. Subsequently, the intermediate I3 (1.00 equivalent) is reacted with 2,6-diphenyl-1,3,5-triazine-4-boronic acid pinacol ester (1.10 equivalents) employing similar conditions as in AAV2 to yield Z7.

General Procedure for Synthesis AAV8:

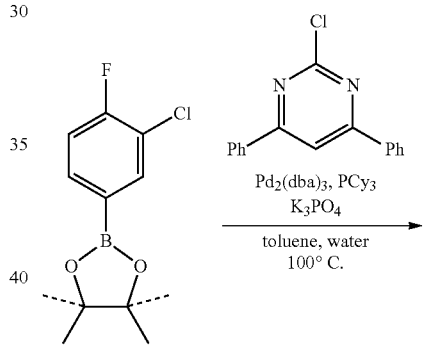

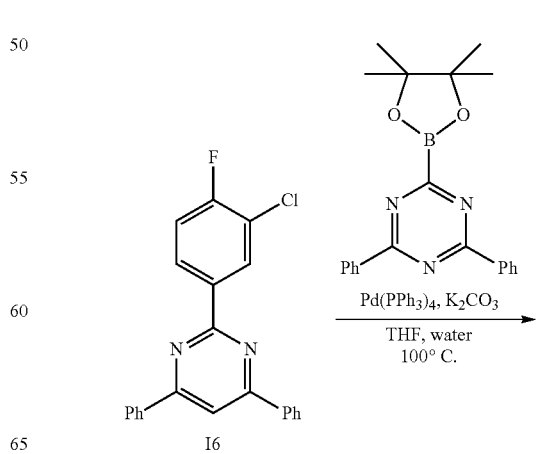

I6

-continued

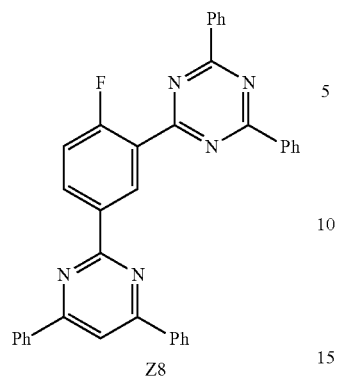

Z8

-continued

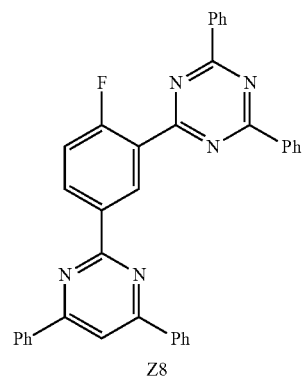

Z8

3-Chloro-4-fluorophenyl-boronic acid pinacol ester (1.00 equivalent) is reacted with 2-chloro-4,6-diphenyl-1,3-pyrimidine (1.10 equivalents) to yield intermediate I6 employing similar conditions as in AAV3. Subsequently, the intermediate I6 (1.00 equivalent) is reacted with 4,6-diphenyl-1,3,5-triazine-2-boronic acid pinacol ester (1.25 equivalents) employing similar conditions as in AAV1 to yield Z8.

General Procedure for Synthesis AAV8-2:

5-Chloro-2-fluorophenyl-boronic acid pinacol ester (1.00 equivalent) is reacted with 2-chloro-4,6-diphenyl-1,3,5-triazine (1.25 equivalents) to yield intermediate I5 employing similar conditions as in AAV1. Subsequently, the intermediate I5 (1.00 equivalent) is reacted with 4,6-diphenyl-1,3-pyrimidine-2-boronic acid pinacol ester (1.10 equivalents) employing similar conditions as in AAV3 to yield Z8.

General Procedure for Synthesis AAV9:

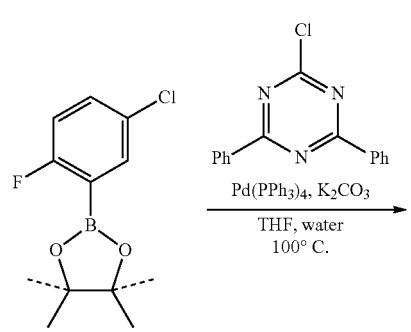

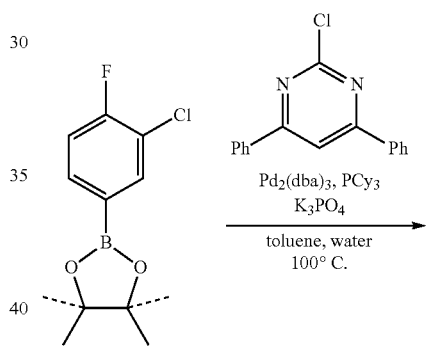

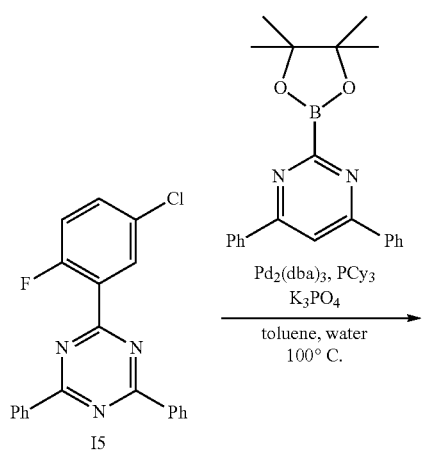

I5

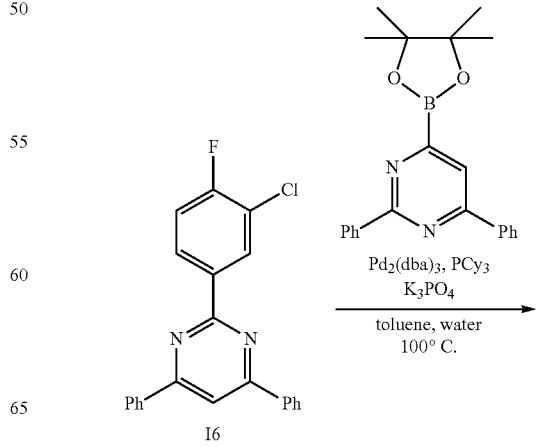

I6

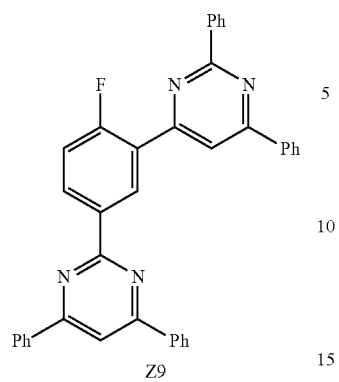

Z9

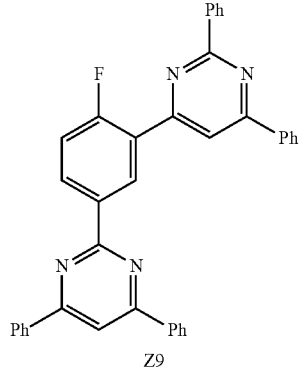

Z9

3-Chloro-4-fluorophenyl-boronic acid pinacol ester (1.00 equivalent) is reacted with 2-chloro-4,6-diphenyl-1,3-pyrimidine (1.10 equivalents) to yield intermediate I6 employing similar conditions as in AAV3. Subsequently, the intermediate I6 (1.00 equivalent) is reacted with 2,6-diphenyl-1,3-pyrimidine-4-boronic acid pinacol ester (1.10 equivalents) employing similar conditions as in AAV2 to yield Z9.

General Procedure for Synthesis AAV9-2:

5-Chloro-2-fluorophenyl-boronic acid pinacol ester (1.00 equivalent) is reacted with 4-chloro-2,6-diphenyl-1,3-pyrimidine (1.10 equivalents) to yield intermediate I2 employing similar conditions as in AAV2. Subsequently, the intermediate I2 (1.00 equivalent) is reacted with 4,6-diphenyl-1,3,5-triazine-2-boronic acid pinacol ester (1.10 equivalents) employing similar conditions as in AAV3 to yield Z9.

In a further alternative, the two respective reaction steps described in AAV4 to AAV9-2 can be performed in a one-pot reaction. In that case, the solvent mixture of either one of the two reaction steps is used for both reactions and the reactant, the base and the catalyst of the second reaction step are added after the first reaction is completed.

General Procedure for Synthesis AAV10:

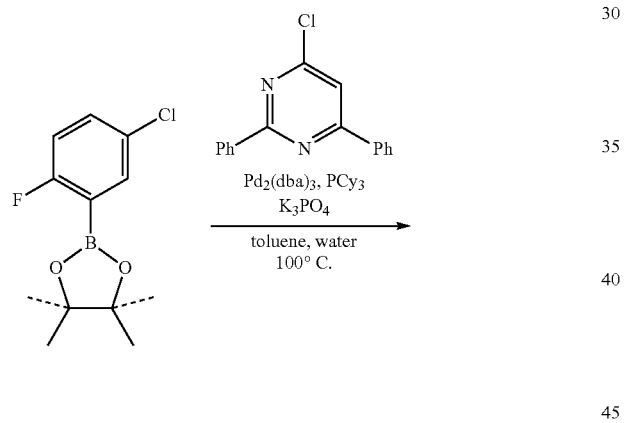

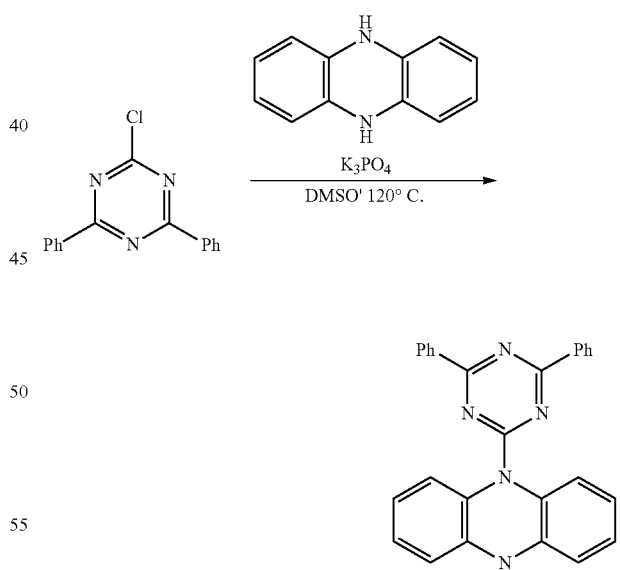

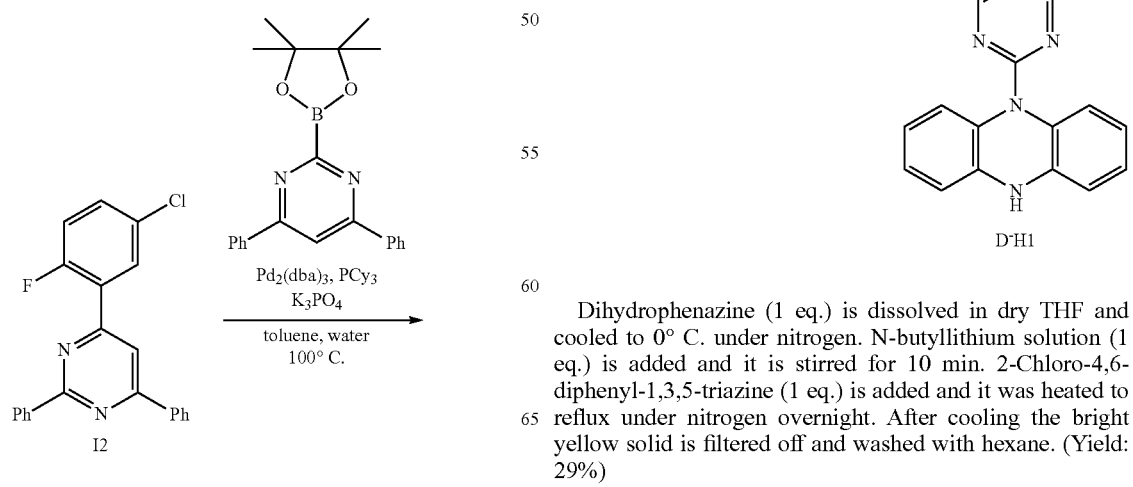

I2

D-H1

Dihydrophenazine (1 eq.) is dissolved in dry THF and cooled to 0° C. under nitrogen. N-butyllithium solution (1 eq.) is added and it is stirred for 10 min. 2-Chloro-4,6-diphenyl-1,3,5-triazine (1 eq.) is added and it was heated to reflux under nitrogen overnight. After cooling the bright yellow solid is filtered off and washed with hexane. (Yield: 29%)

General Procedure for Synthesis AAV10-2:

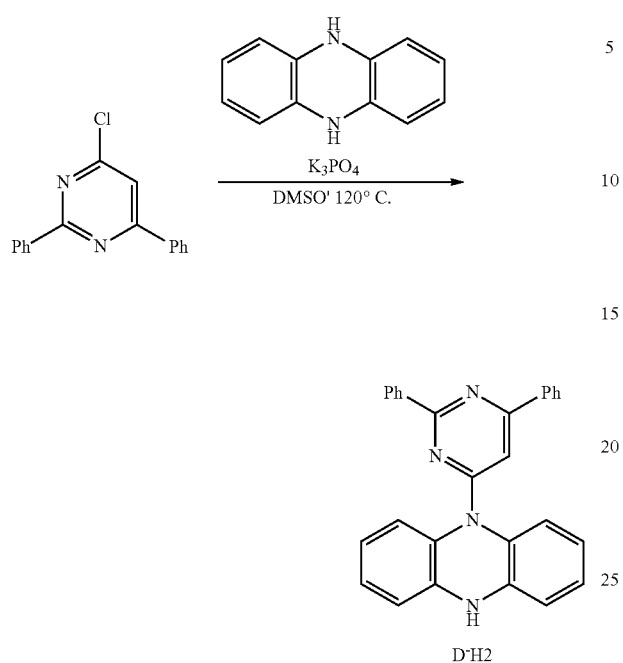

Dihydrophenazine (1 eq.) is dissolved in dry THF and cooled to 0° C. under nitrogen. N-butyllithium solution (1 eq.) is added and it is stirred for 10 min. 4-Chloro-2,6-diphenylpyrimidine (1 eq.) is added and it is heated to reflux under nitrogen overnight. After cooling, the solid is filtered off and washed with hexane to obtain the pure product.

General Procedure for Synthesis AAV10-3:

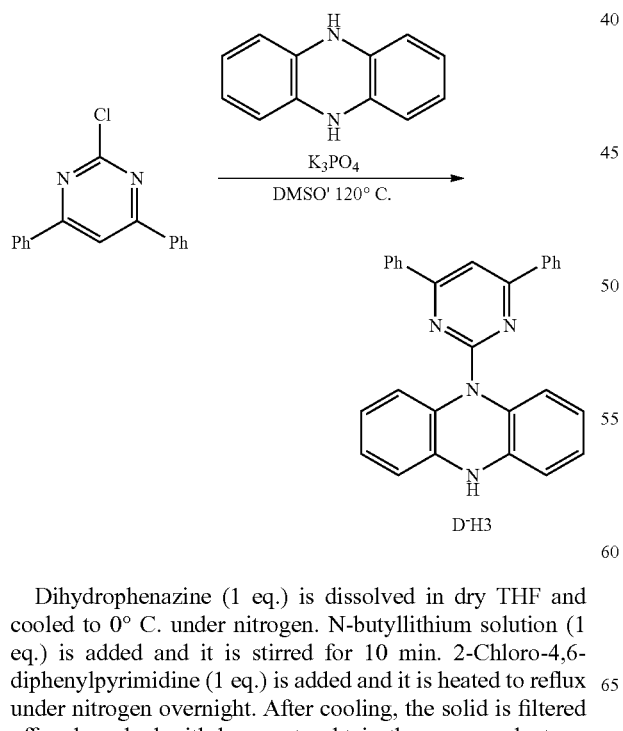

Dihydrophenazine (1 eq.) is dissolved in dry THF and cooled to 0° C. under nitrogen. N-butyllithium solution (1 eq.) is added and it is stirred for 10 min. 2-Chloro-4,6-diphenylpyrimidine (1 eq.) is added and it is heated to reflux under nitrogen overnight. After cooling, the solid is filtered off and washed with hexane to obtain the pure product.

General Procedure for Synthesis AAV11:

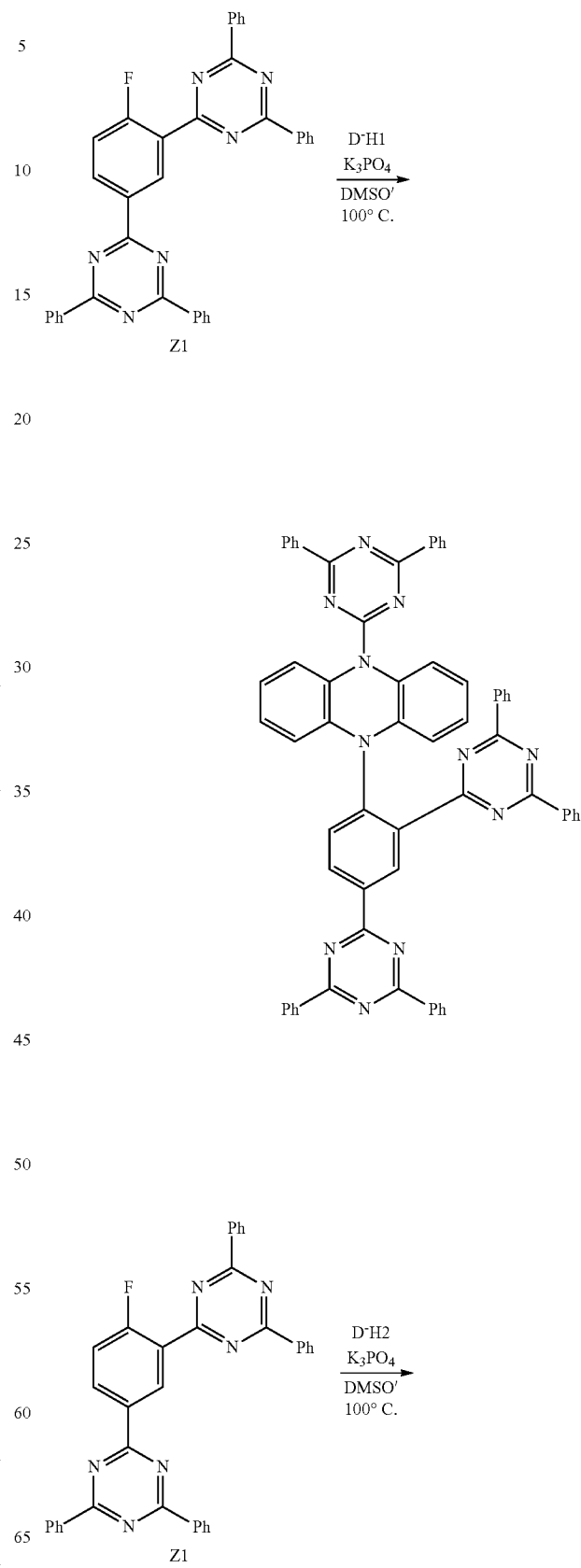

-continued
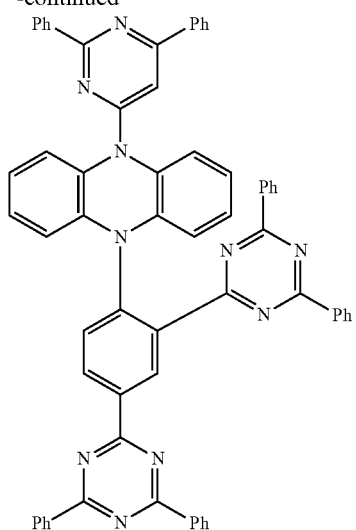
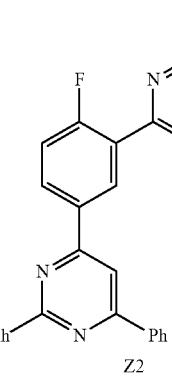
Z1
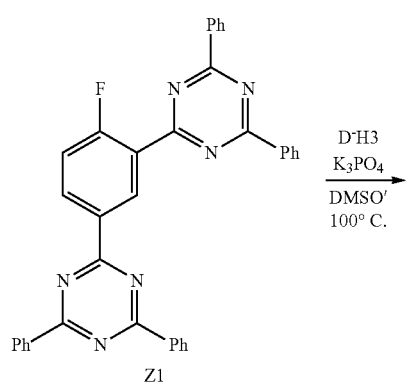
-continued
 D-H1
K₃PO₄
DMSO'
100° C.
Z2
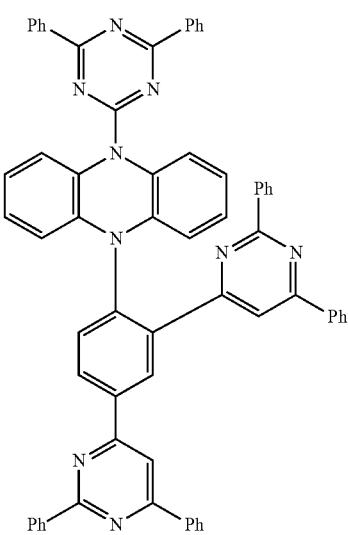
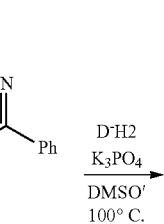 D-H2
K₃PO₄
DMSO'
100° C.
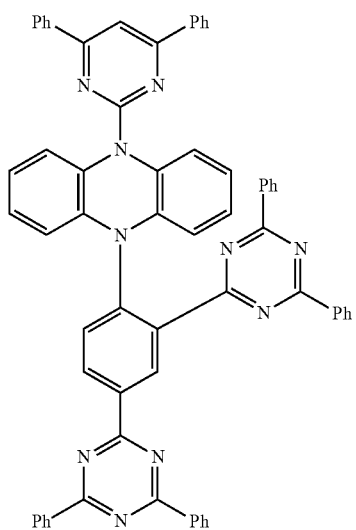
Z2

-continued
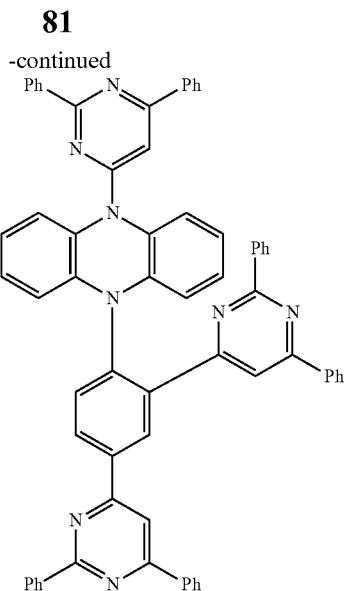
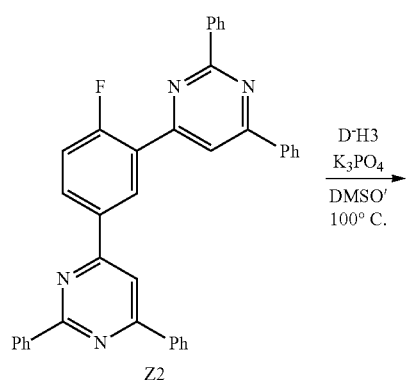
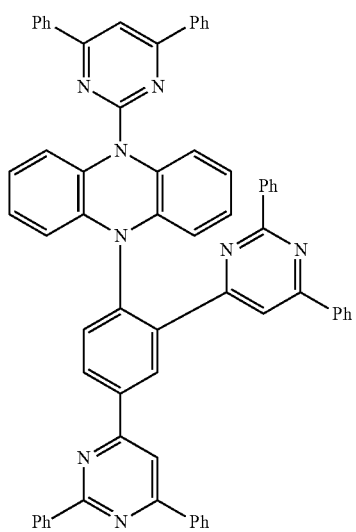
-continued
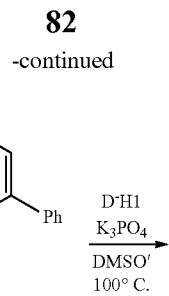
D-H1
K₃PO₄
DMSO'
100° C.
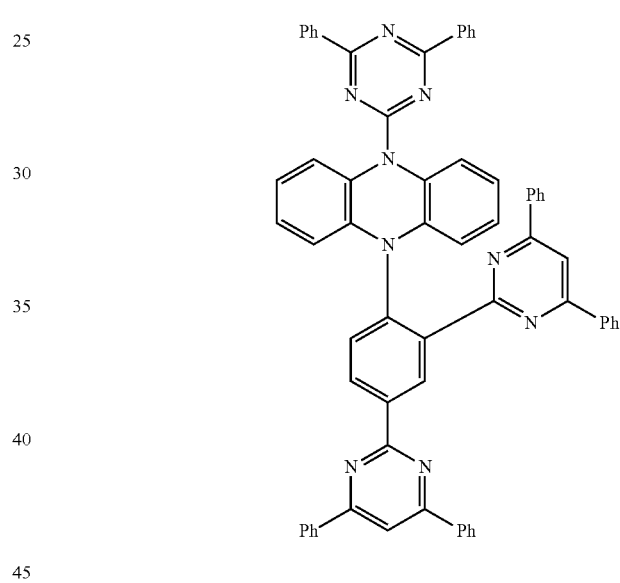
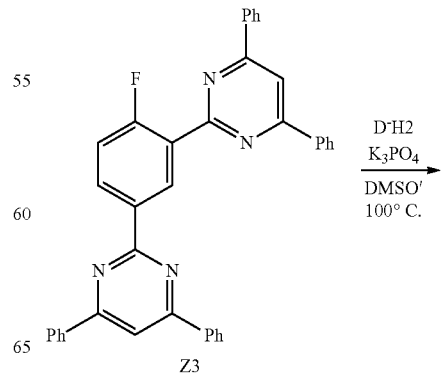
D-H2
K₃PO₄
DMSO'
100° C.

-continued
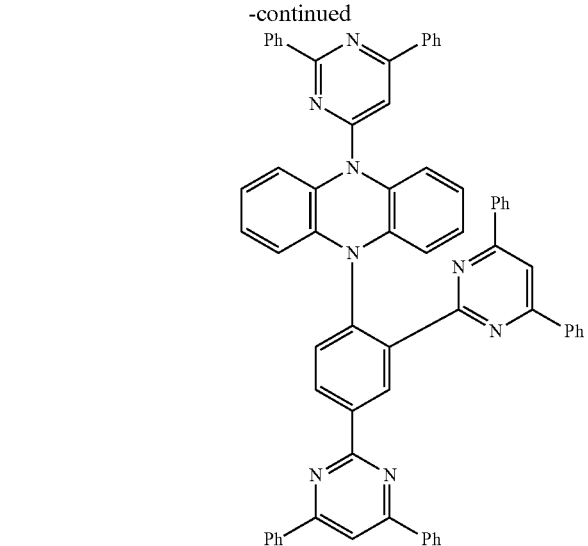
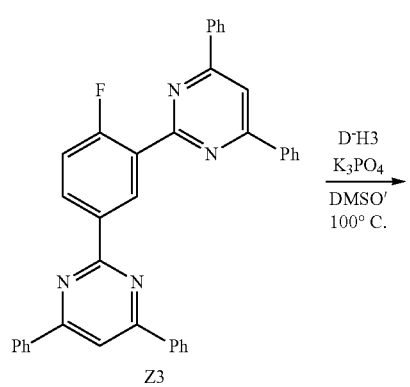
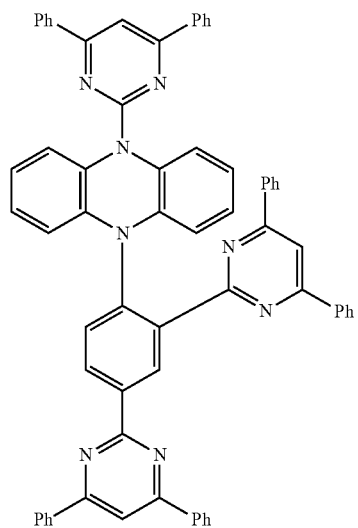
-continued
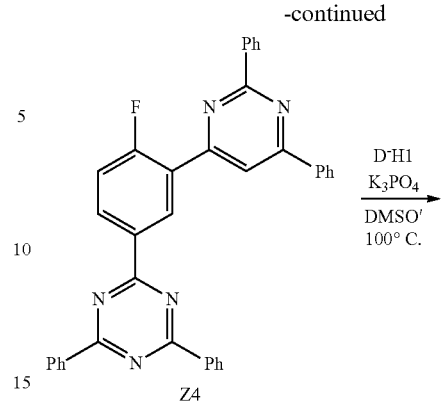
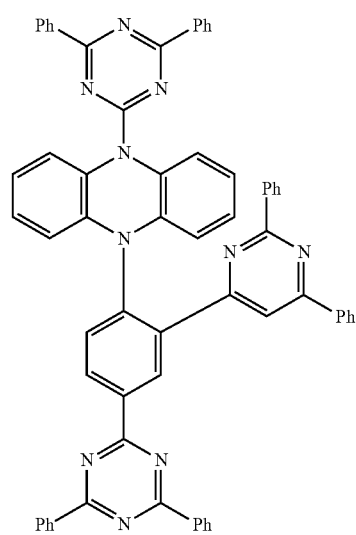
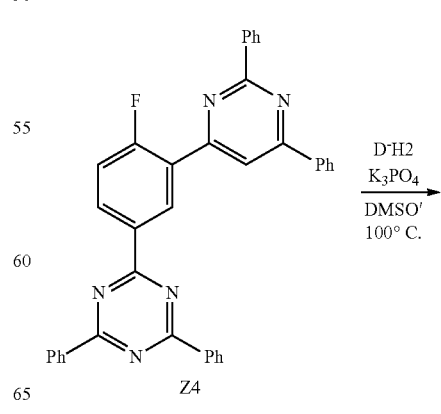

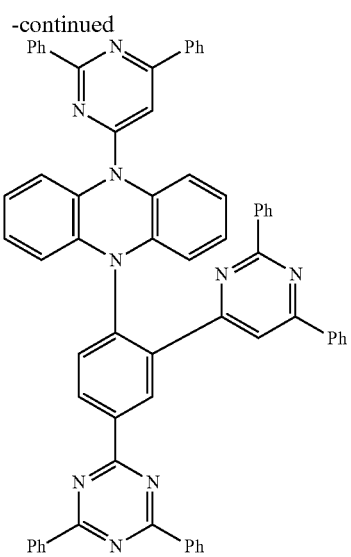
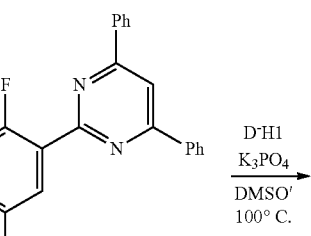
Z5
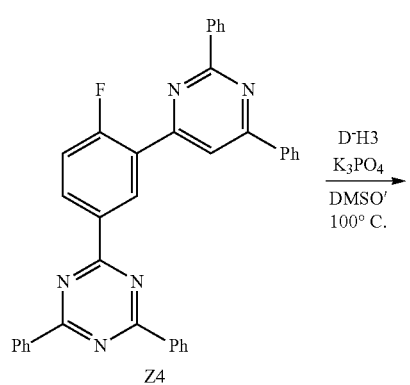
Z4
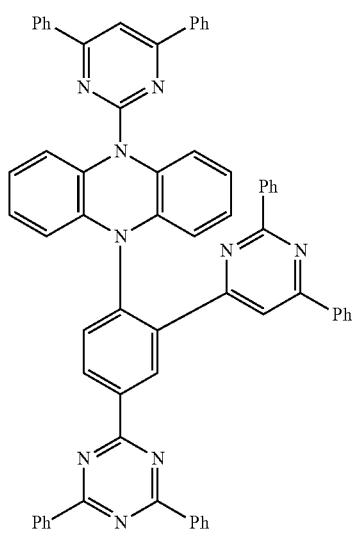
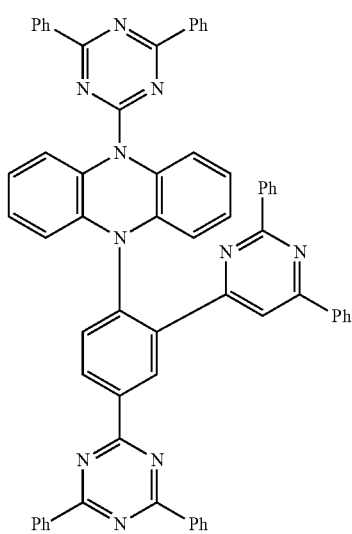
Z5

87
-continued
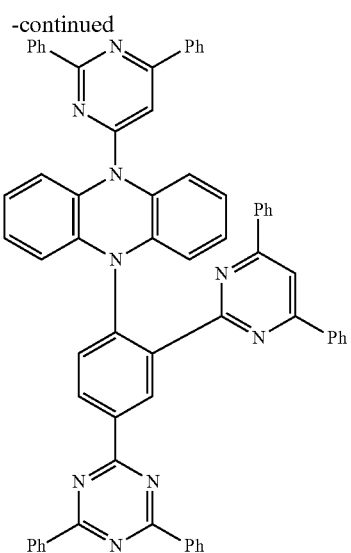
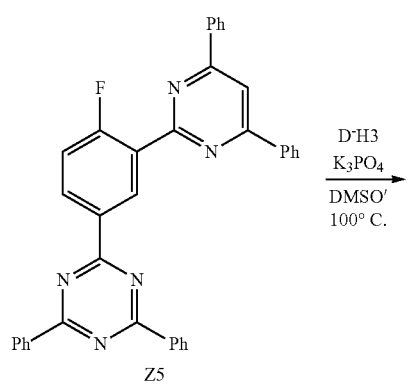
Z5
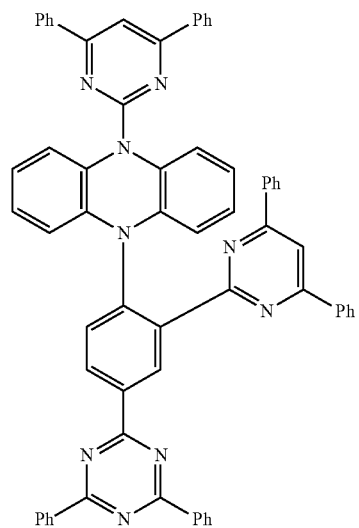
88
-continued
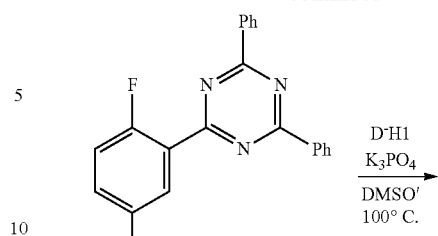
Z6
$\xrightarrow{\text{D-H1} \atop \text{K}_3\text{PO}_4 \atop \text{DMSO'} \atop 100° \text{C.}}$
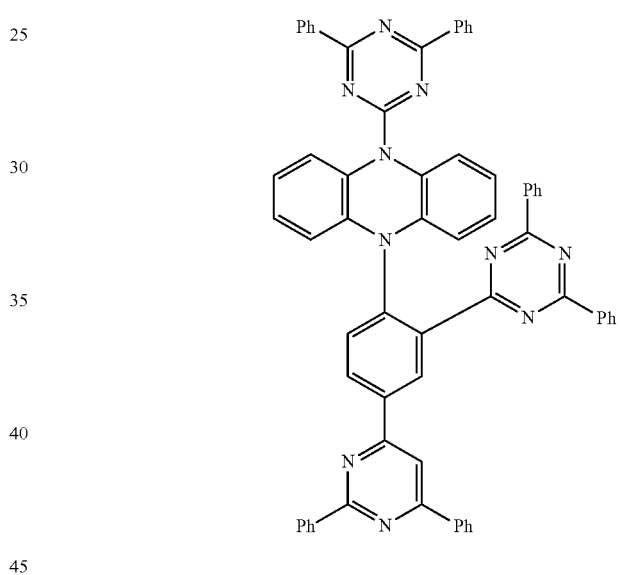
$\xrightarrow{\text{D-H2} \atop \text{K}_3\text{PO}_4 \atop \text{DMSO'} \atop 100° \text{C.}}$
Z6

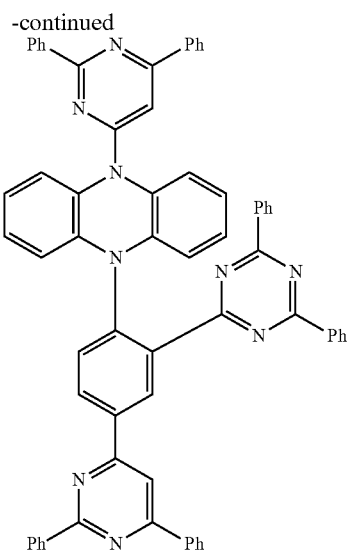
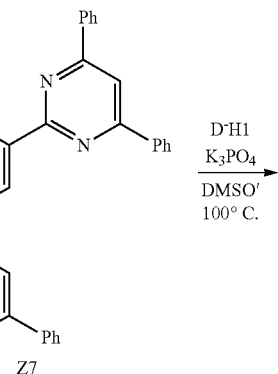
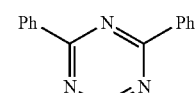
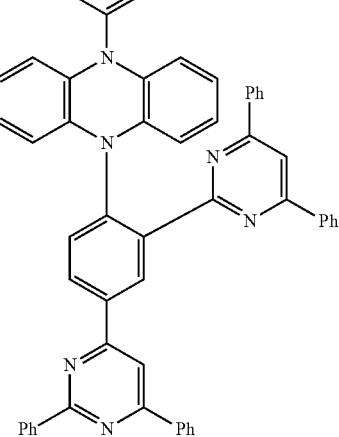
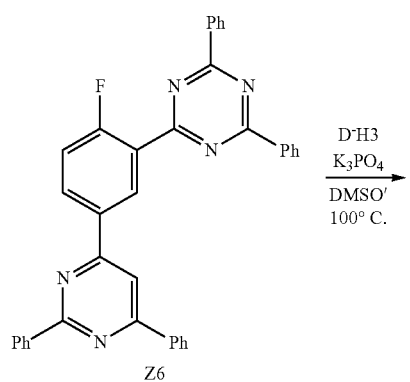
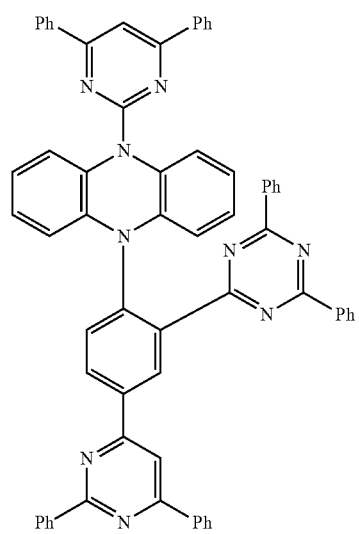
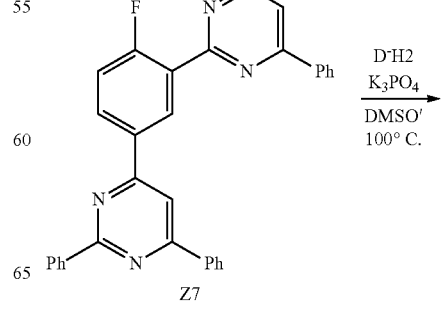

-continued
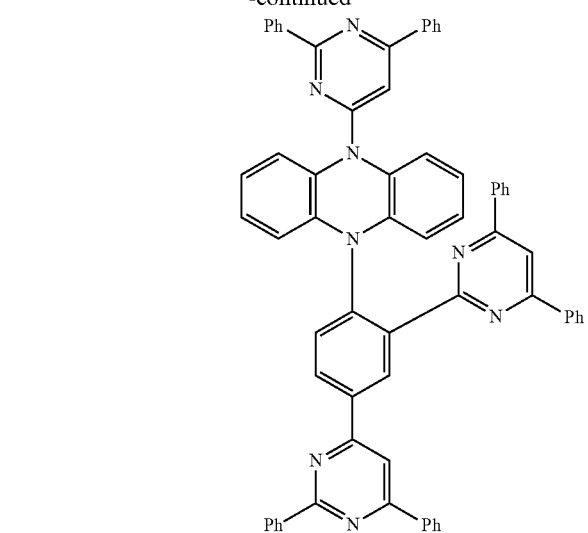
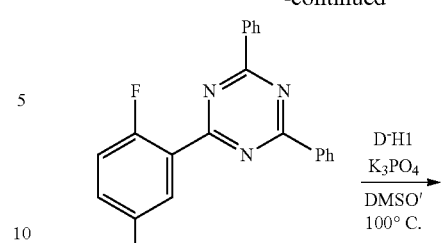
Z8
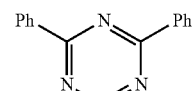
Z7
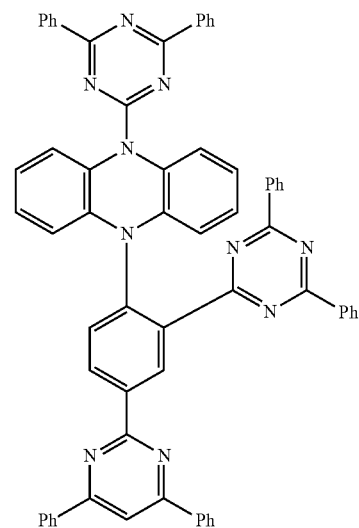
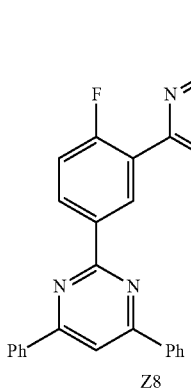
Z8

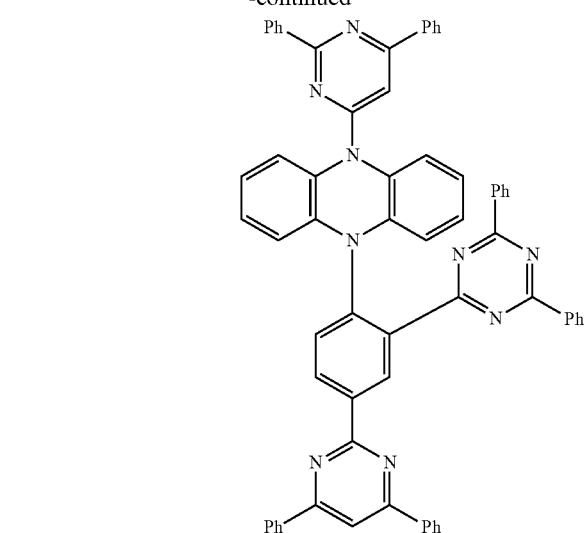
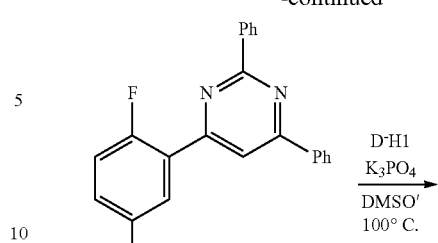
Z9
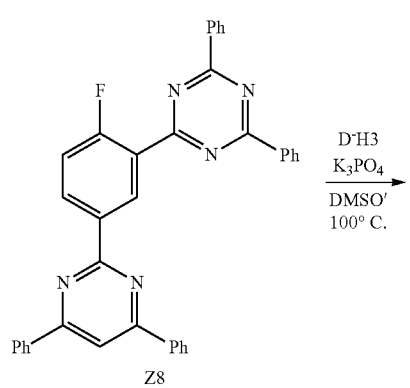
Z8
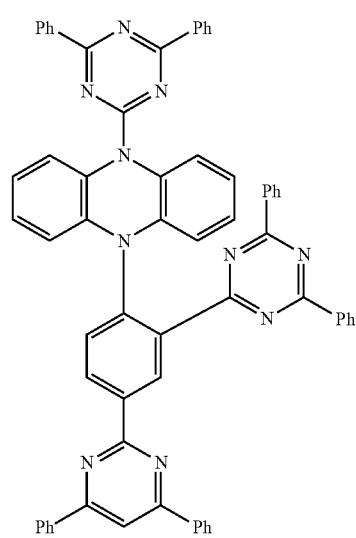
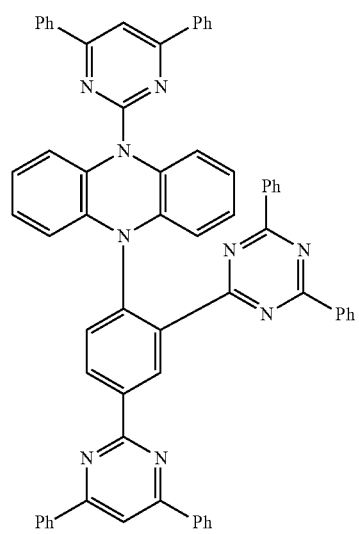
Z9

-continued
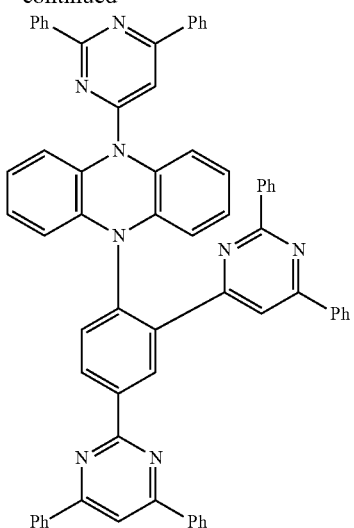
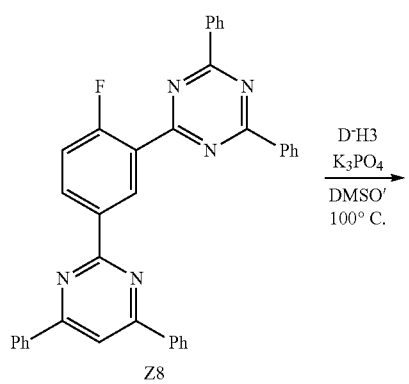
-continued
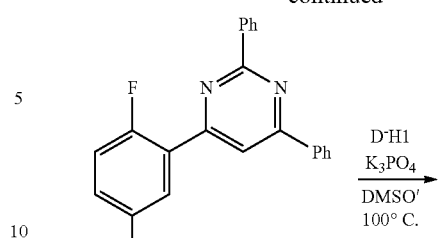
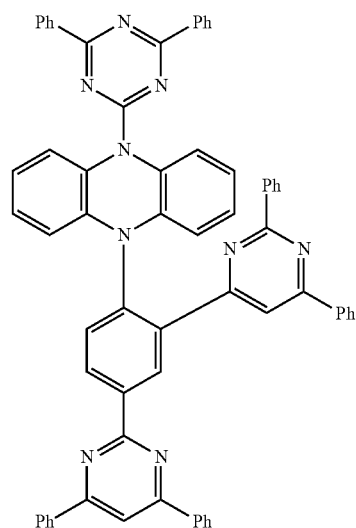
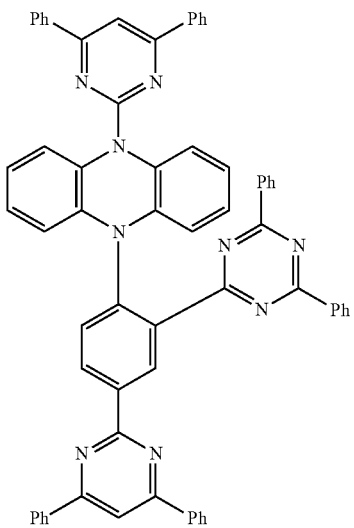
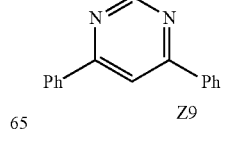

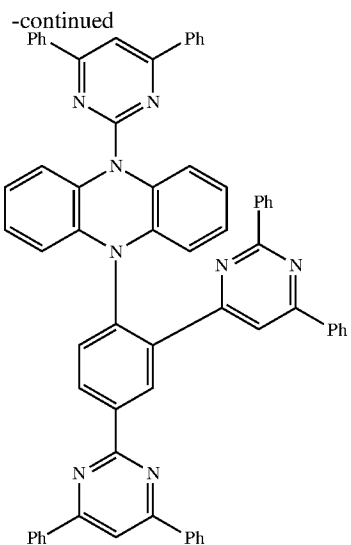

Z1, Z2, Z3, Z4, Z5, Z6, Z7, Z8 or Z9 (1 equivalent each), the corresponding donor molecule D-H (D-H1, D-H2, or D-H3; 1.00 equivalents) and tribasic potassium phosphate (2.00 equivalents) are suspended under nitrogen atmosphere in DMSO and stirred at 100° C. (16 h). After chilling to room temperature, the reaction mixture is poured into water in order to precipitate the organics. The precipitate is filtered off (fiber glass filter) and subsequently dissolved in dichloromethane. The resulting solution is added to brine and the phases were separated. After drying over $MgSO_4$, the crude product is purified by recrystallization or by flash chromatography. The product is obtained as a solid.

Cyclic Voltammetry

Cyclic voltammograms are measured from solutions having concentration of $10^{-3}$ mol/L of the organic molecules in dichloromethane or a suitable solvent and a suitable supporting electrolyte (e.g. 0.1 mol/L of tetrabutylammonium hexafluorophosphate). The measurements are conducted at room temperature under nitrogen atmosphere with a three-electrode assembly (Working and counter electrodes: Pt wire, reference electrode: Pt wire) and calibrated using $FeCp_2/FeCp^+$ as internal standard. The HOMO data was corrected using ferrocene as internal standard against a saturated calomel electrode (SCE).

Density Functional Theory Calculation

Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating Apparatus: Spin150, SPS euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are dried at 70° C. for 1 min.

Photoluminescence spectroscopy and TCSPC (Time-correlated single-photon counting) Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation sources:

NanoLED 370 (wavelength: 371 nm, puls duration: 1.1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement $C_{9920}$-03G system (Hamamatsu Photonics) is used. Quantum yields and CIE coordinates are determined using the software U6039-05 version 3.6.0.

Emission maxima are given in nm, quantum yields ct in % and CIE coordinates as x,y values.

PLQY is determined using the following protocol:
1) Quality assurance: Anthracene in ethanol (known concentration) is used as reference
2) Excitation wavelength: the absorption maximum of the organic molecule is determined and the molecule is excited using this wavelength
3) Measurement Quantum yields are measured for sample of solutions or films under nitrogen atmosphere. The yield is calculated using the equation:

$$\Phi_{PL} = \frac{n_{photon,emited}}{n_{photon,absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

wherein $n_{photon}$ denotes the photon count and Int. the intensity.

Production and Characterization of Organic Electroluminescence Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc. Accelerated lifetime measurements are performed (e.g. applying increased current densities). Exemplarily LT80 values at 500 cd/m² are determined using the following equation:

$$LT80\left(500\frac{cd^2}{m^2}\right) = LT80(L_0)\left(\frac{L_0}{500\frac{cd^2}{m^2}}\right)^{1.6}$$

wherein $L_0$ denotes the initial luminance at the applied current density. The values correspond to the average of several pixels (typically two to eight), the standard deviation between these pixels is given.

HPLC-MS

HPLC-MS analysis is performed on an HPLC by Agilent (1100 series) with MS-detector (Thermo LTQ XL).

Exemplary a typical HPLC method is as follows: a reverse phase column 4.6 mm×150 mm, particle size 3.5 μm from Agilent (ZORBAX Eclipse Plus 95 Å C18, 4.6×150 mm, 3.5 μm HPLC column) is used in the HPLC. The HPLC-MS measurements are performed at room temperature (rt) following gradients

| Flow rate [ml/min] | time [min] | A[%] | B[%] | C[%] |
|---|---|---|---|---|
| 2.5 | 0 | 40 | 50 | 10 |
| 2.5 | 5 | 40 | 50 | 10 |
| 2.5 | 25 | 10 | 20 | 70 |
| 2.5 | 35 | 10 | 20 | 70 |
| 2.5 | 35.01 | 40 | 50 | 10 |
| 2.5 | 40.01 | 40 | 50 | 10 |
| 2.5 | 41.01 | 40 | 50 | 10 | using the following solvent mixtures:

| Solvent A: | H2O (90%) | MeCN (10%) |
|---|---|---|
| Solvent B: | H2O (10%) | MeCN (90%) |
| Solvent C: | THF (50%) | MeCN (50%) |

An injection volume of 5 μL from a solution with a concentration of 0.5 mg/mL of the analyte is taken for the measurements.

Ionization of the probe is performed using an atmospheric pressure chemical ionization (APCI) source either in positive (APCI+) or negative (APCI−) ionization mode.

Example 1

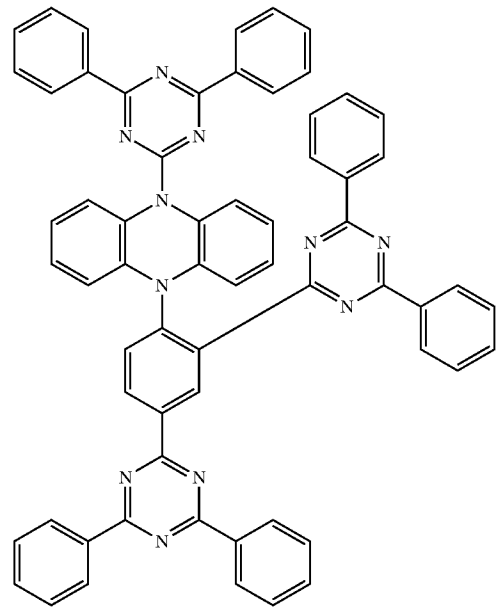 [SMILES: c1ccc(-c2nc(CCc3cc(-c4nc(-c5ccccc5)nc(-c5ccccc5)n4)ccc3N3c4ccccc4N(c4nc(-c5ccccc5)nc(-c5ccccc5)n4)c4ccccc43)nc(-c3ccccc3)n2)cc1]

Example 1 was synthesized according to AAV1 (73% yield), AAV10(29% yield) and AAV11 (91% yield).

¹H NMR (500 MHz, chloroform-d) o 10.06 (d, 1H), 9.19 (dd, 1H), 8.93-8.85 (m, 4H), 8.54-8.48 (m, 4H), 8.30-8.23 (m, 4H), 7.93 (dd, 2H), 7.87 (d, 1H), 7.72-7.60 (m, 6H), 7.59-7.53 (m, 2H), 7.49 (dd, 4H), 7.45-7.39 (m, 2H), 7.39-7.32 (m, 4H), 7.12 (ddd, 2H), 7.02 (ddd, 2H), 6.61 (dd, 2H).

FIG. 1 depicts the emission spectrum of example 1 (10% by weight in mCBP). The emission maximum is at 563 nm, the full width at half maximum is 0.44 eV. The $CIE_x$ value is 0.45 and $CIE_y$ value is 0.53.

Additional Examples of Organic Molecules of the Invention

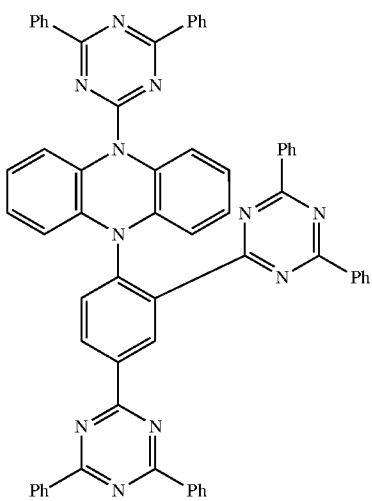

101
-continued
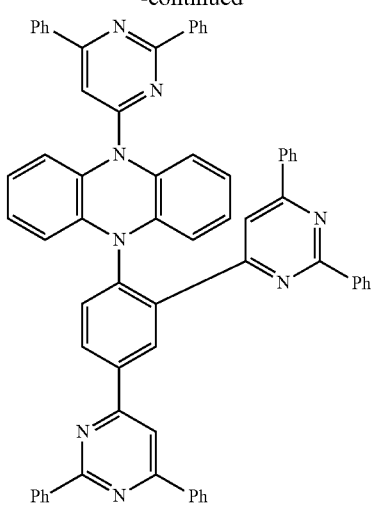
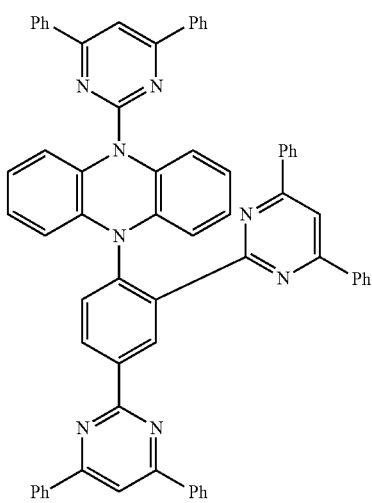
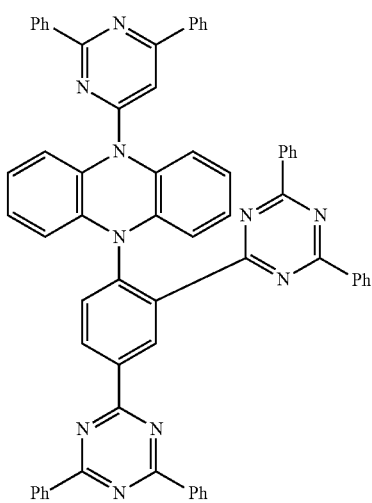
102
-continued
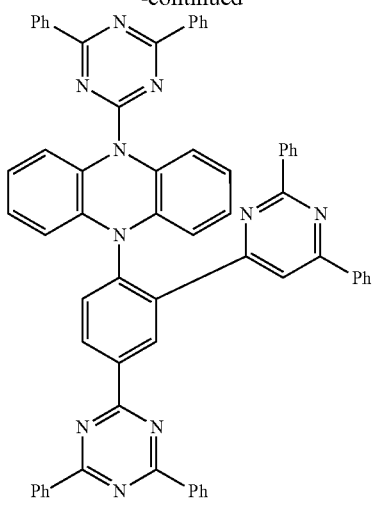
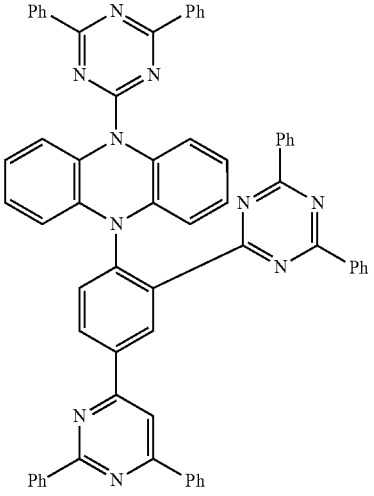
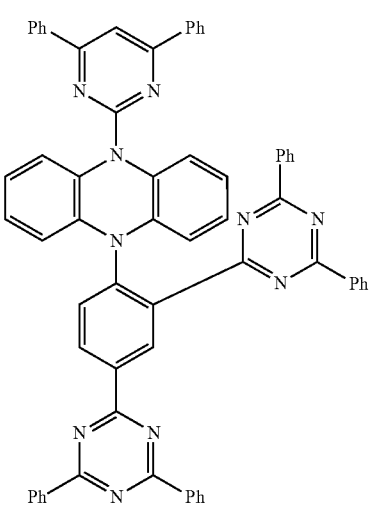

-continued
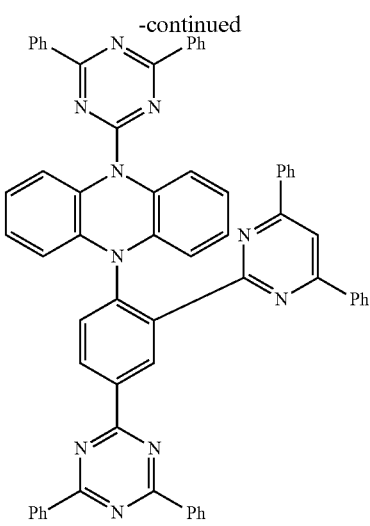
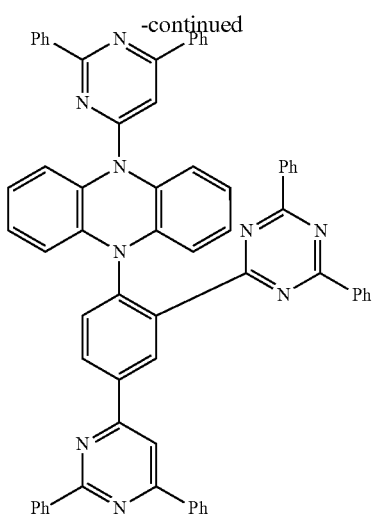
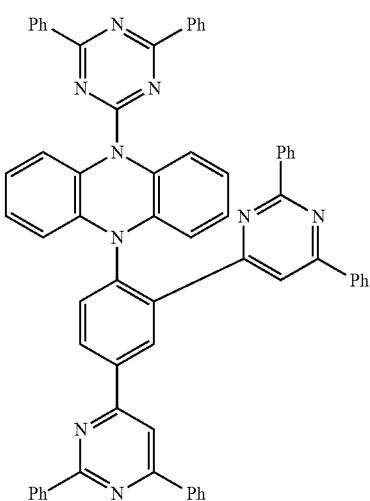

105
-continued
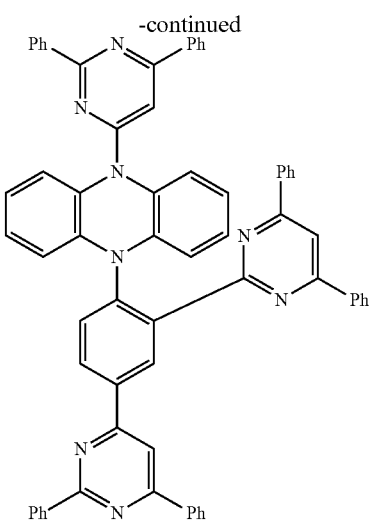
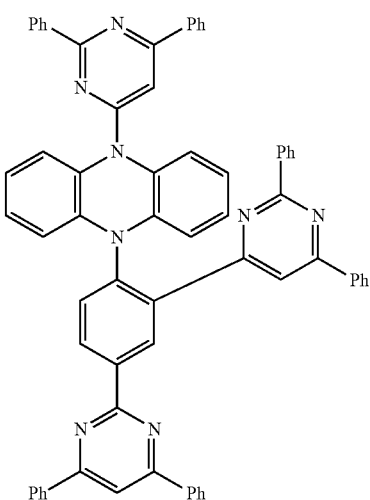
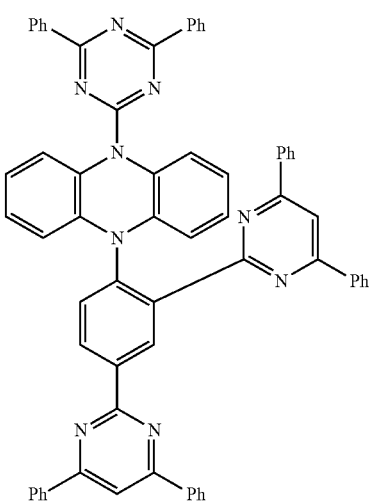
106
-continued
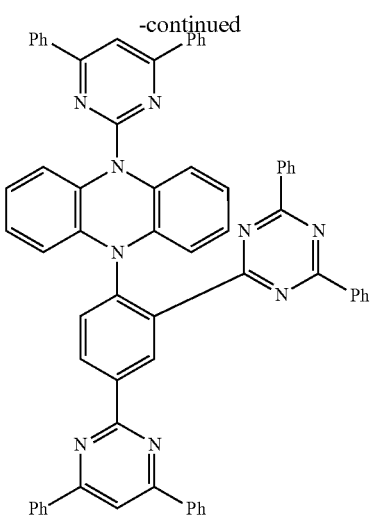
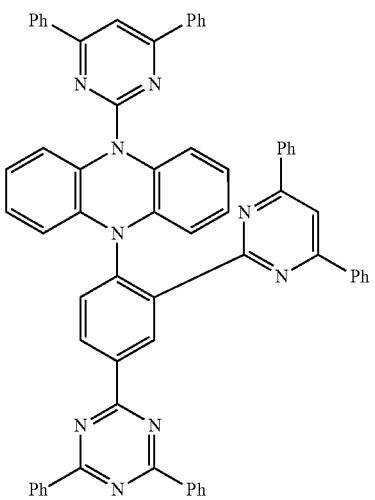
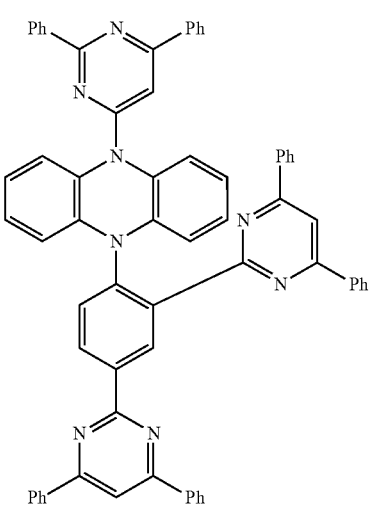

-continued
107
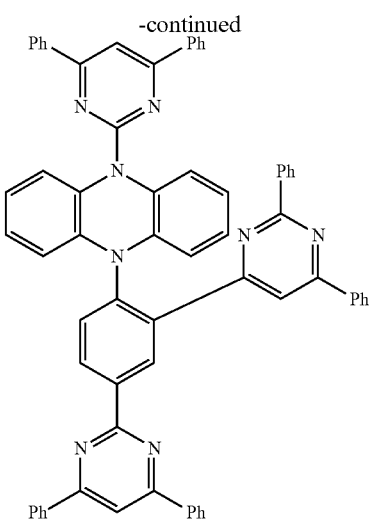
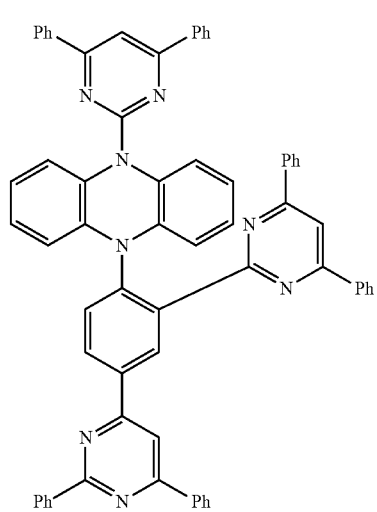
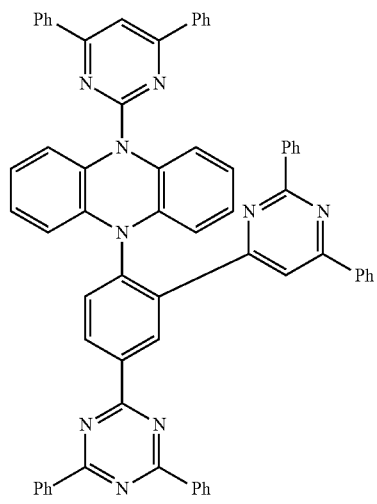
108
-continued
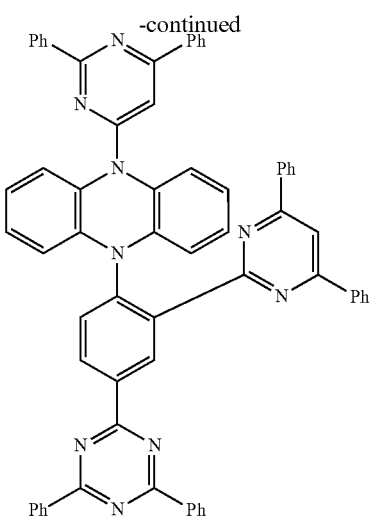
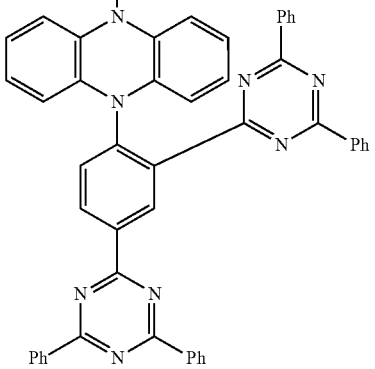
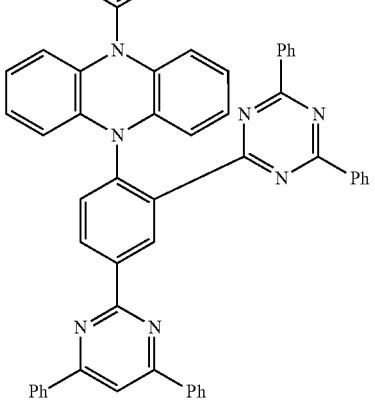

109
-continued
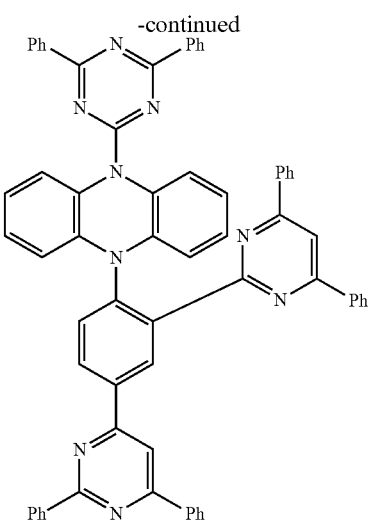
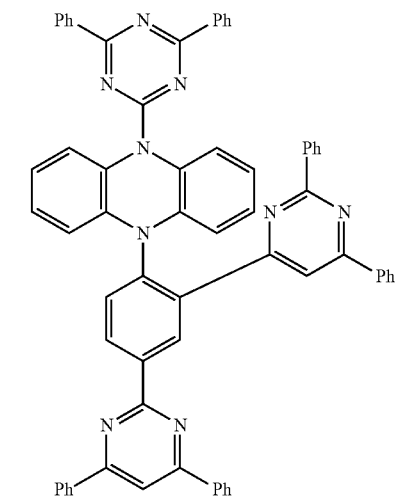
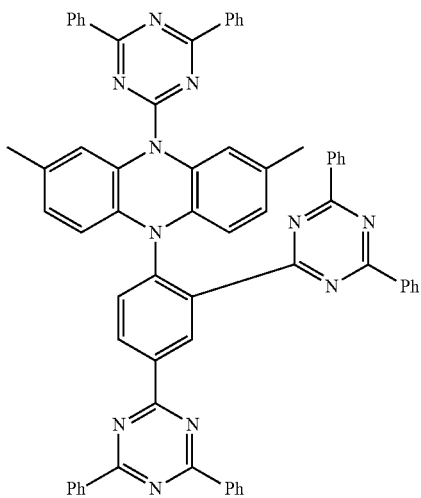
110
-continued
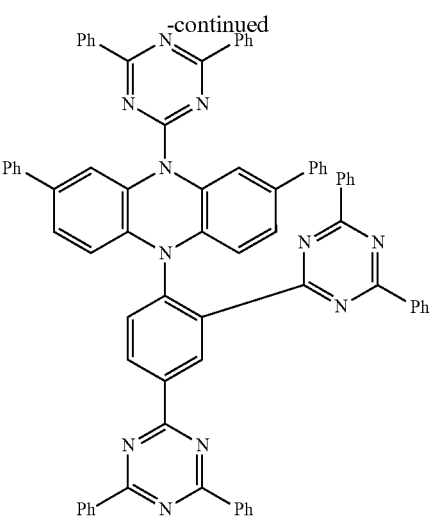
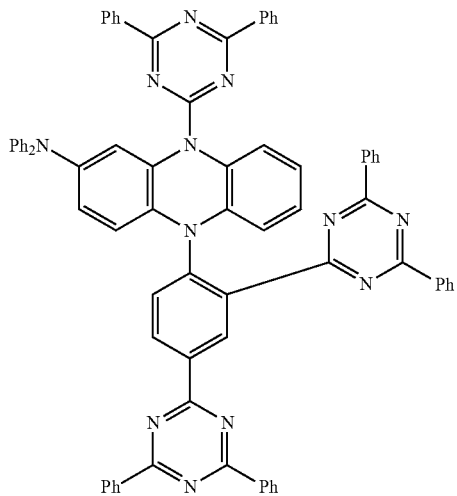
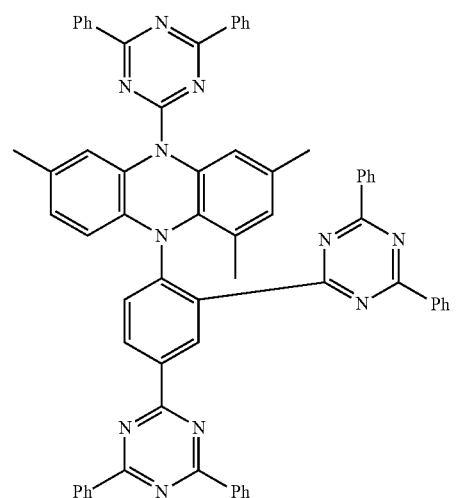

111
-continued
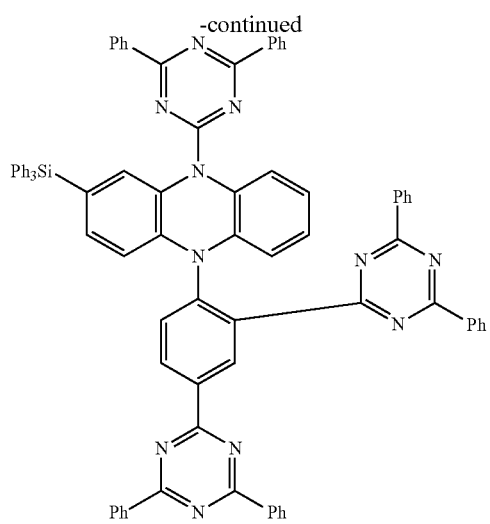
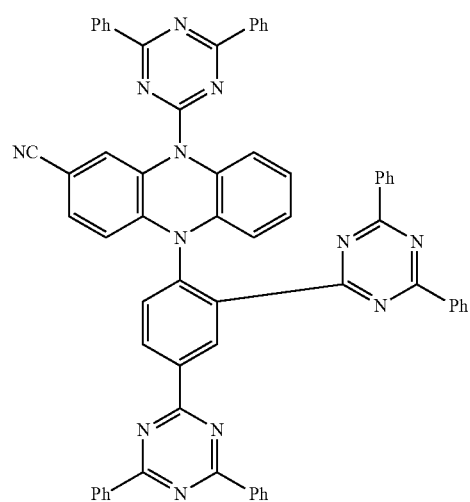
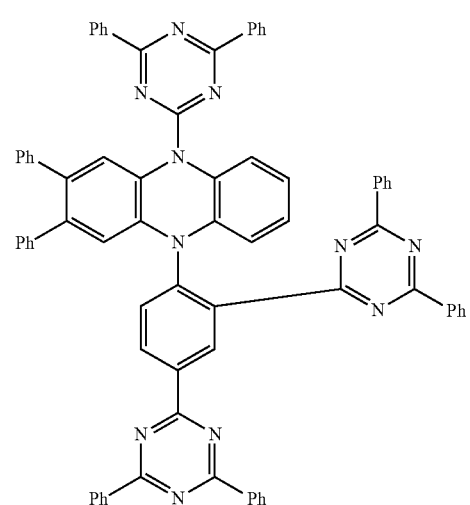
112
-continued
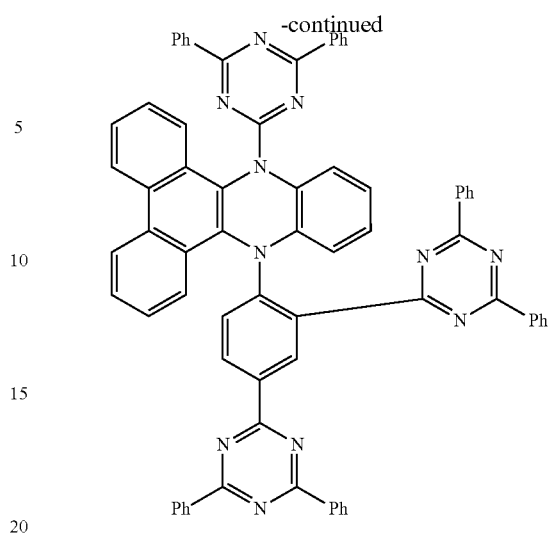
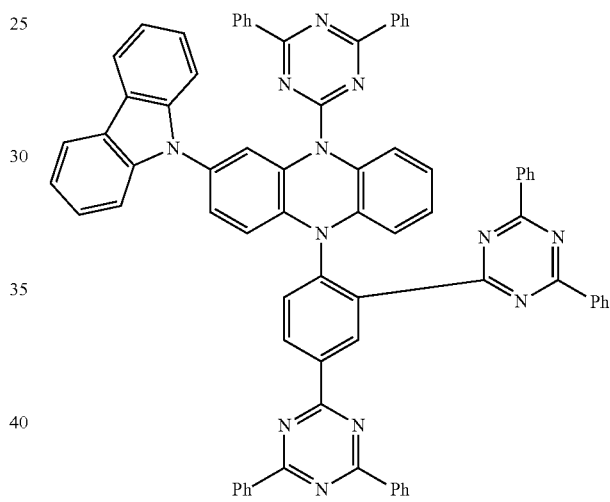
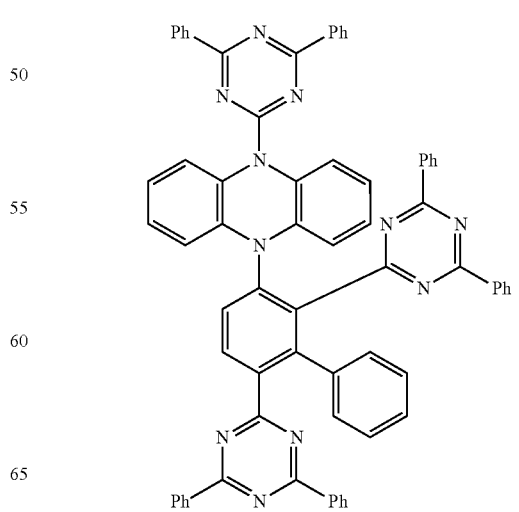

113
-continued
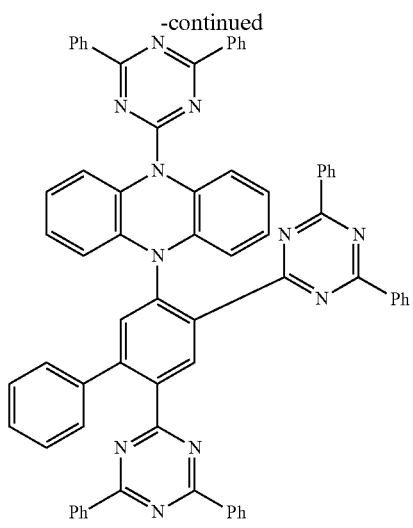
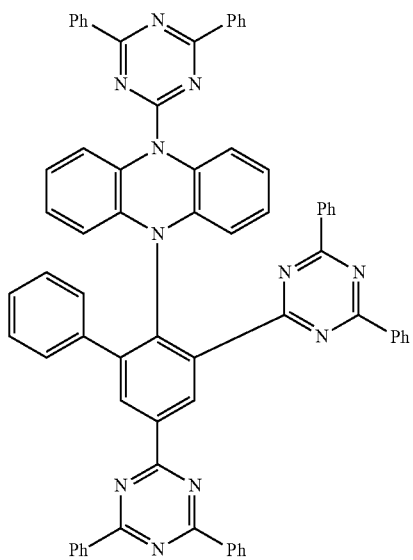
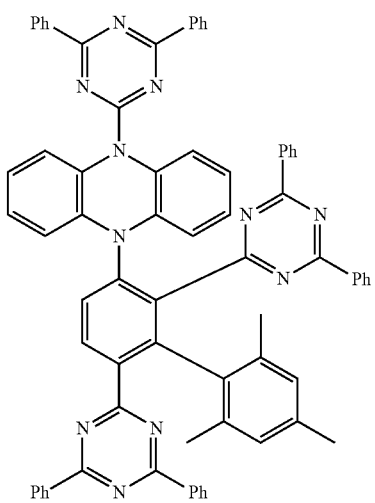
114
-continued
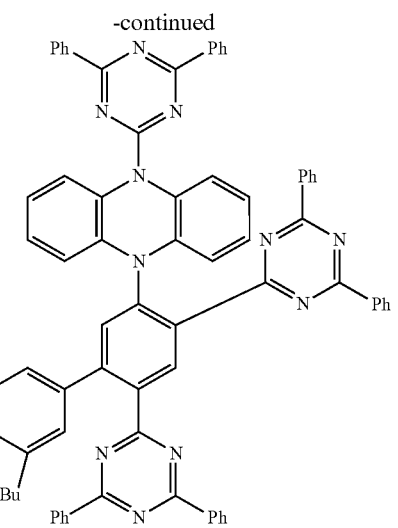
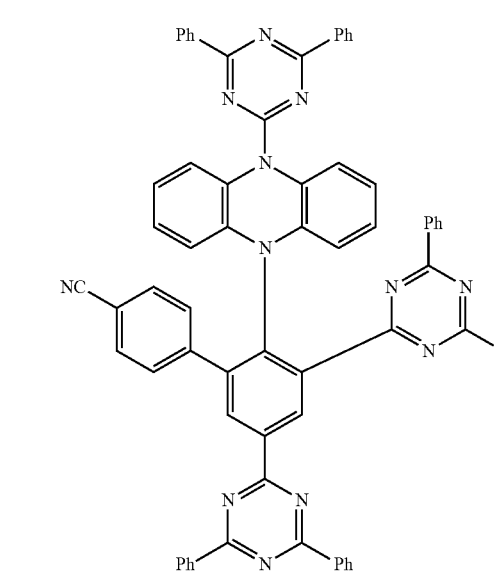
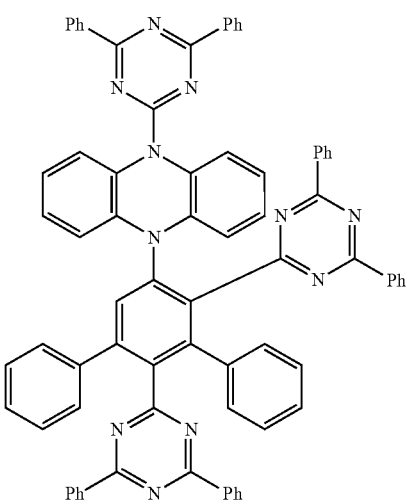 [SMILES: c1ccc(-c2nc(-c3ccccc3)nc(-c3c(-c4ccccc4)cc(N4c5ccccc5N(c5nc(-c6ccccc6)nc(-c6ccccc6)n5)c5ccccc54)c(-c4nc(-c5ccccc5)nc(-c5ccccc5)n4)c3-c3ccccc3)n2)cc1]

115
-continued
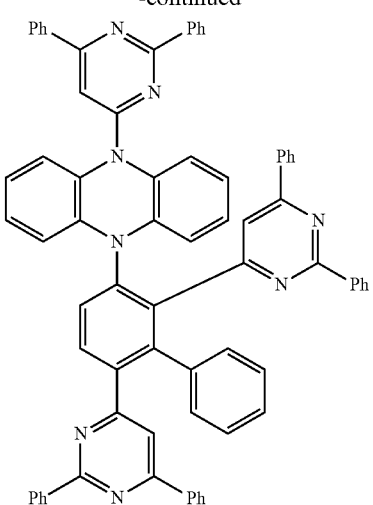
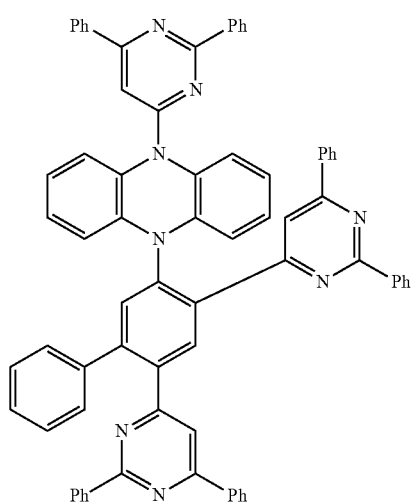
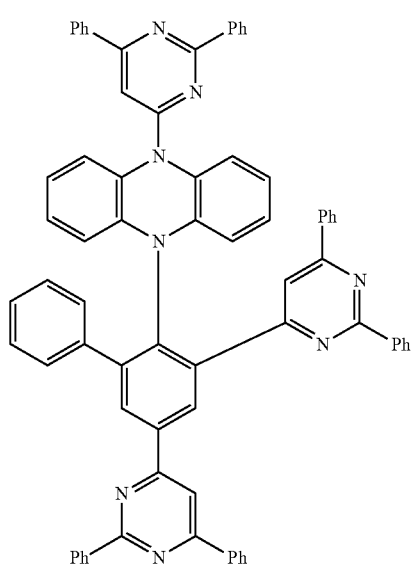
116
-continued
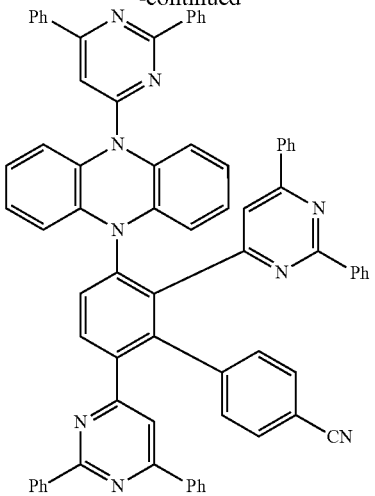
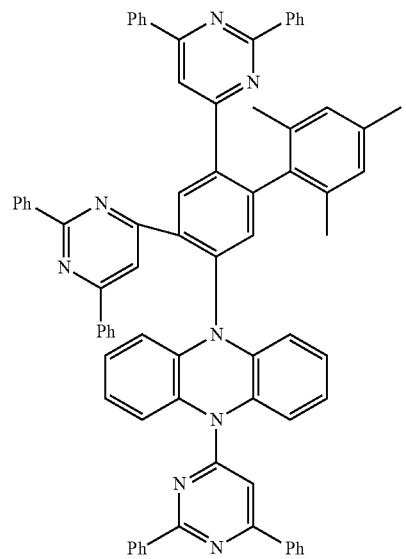
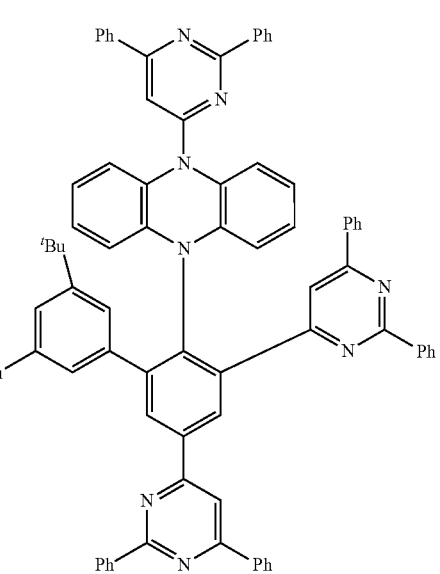

117
-continued
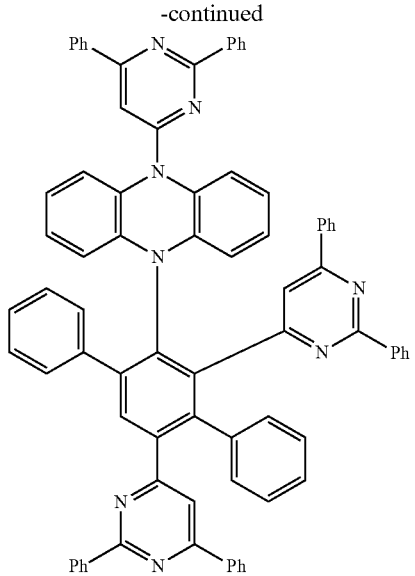
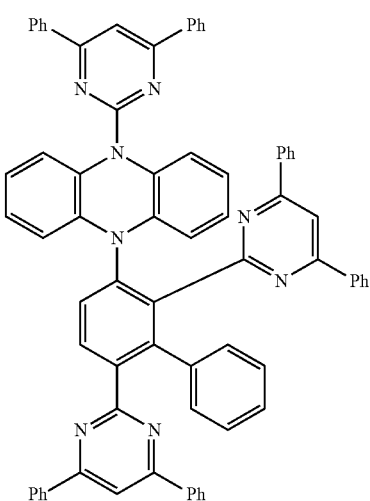
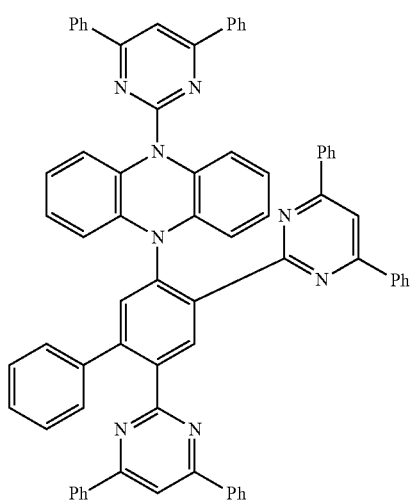
118
-continued
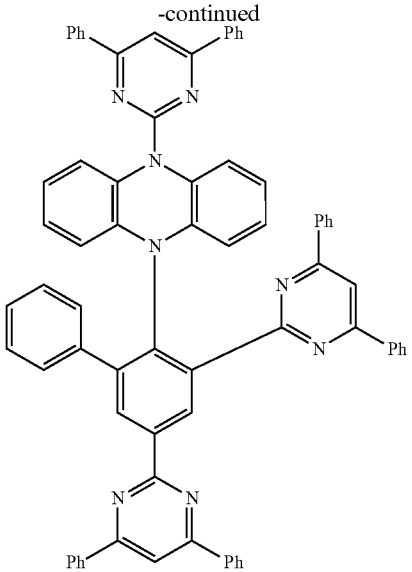
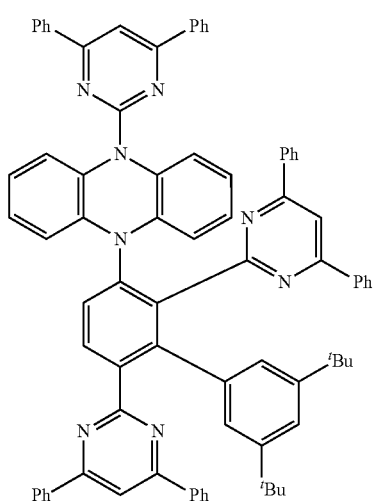
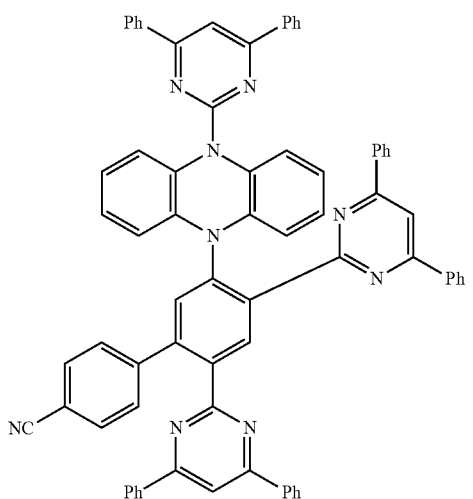

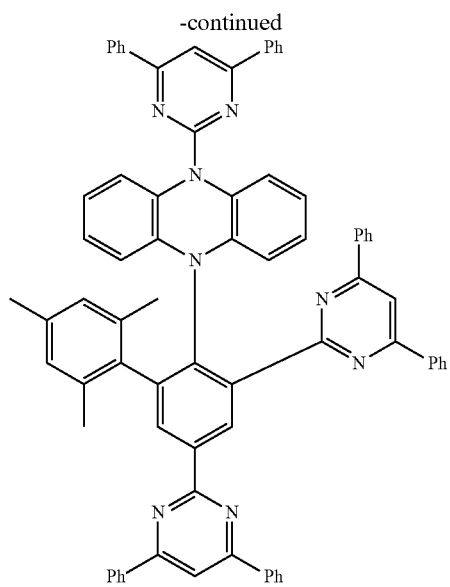
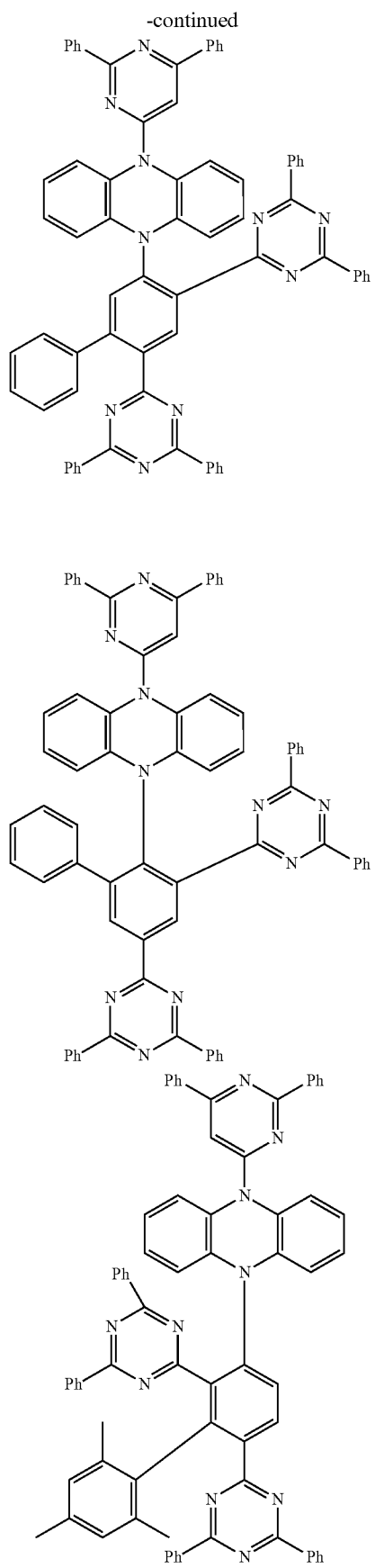

-continued
121
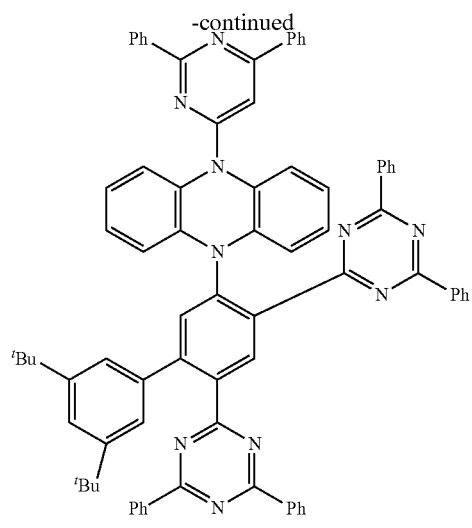
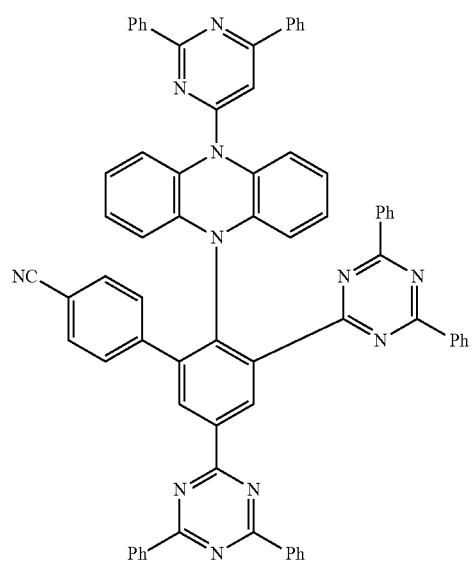
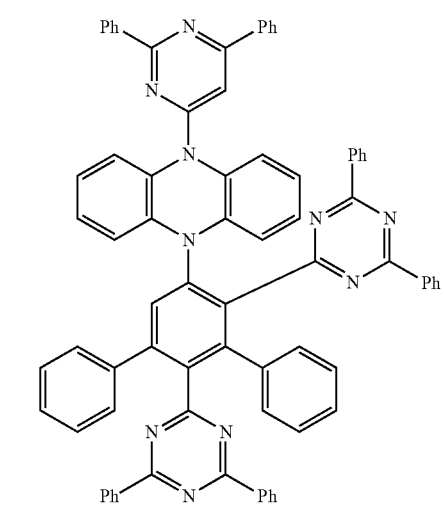 [SMILES: c1ccc(-c2cc(N3c4ccccc4N(c4cc(-c5ccccc5)c(-c5nc(-c6ccccc6)nc(-c6ccccc6)n5)c(-c5ccccc5)c4-c4nc(-c5ccccc5)nc(-c5ccccc5)n4)c4ccccc43)nc(-c3ccccc3)n2)cc1]
122
-continued
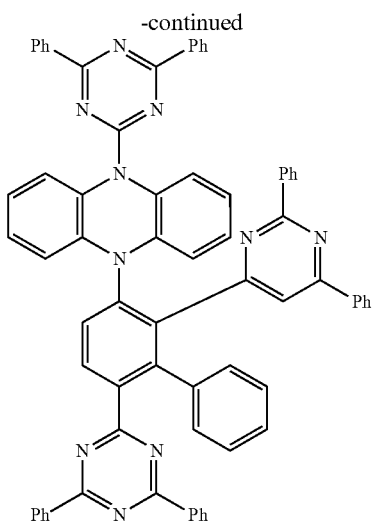
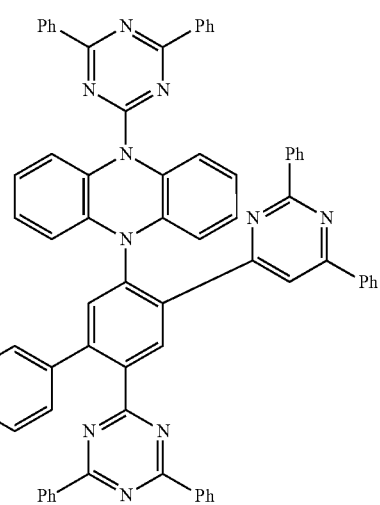
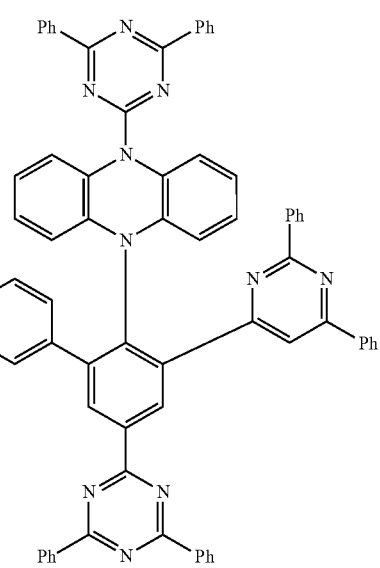

123
-continued
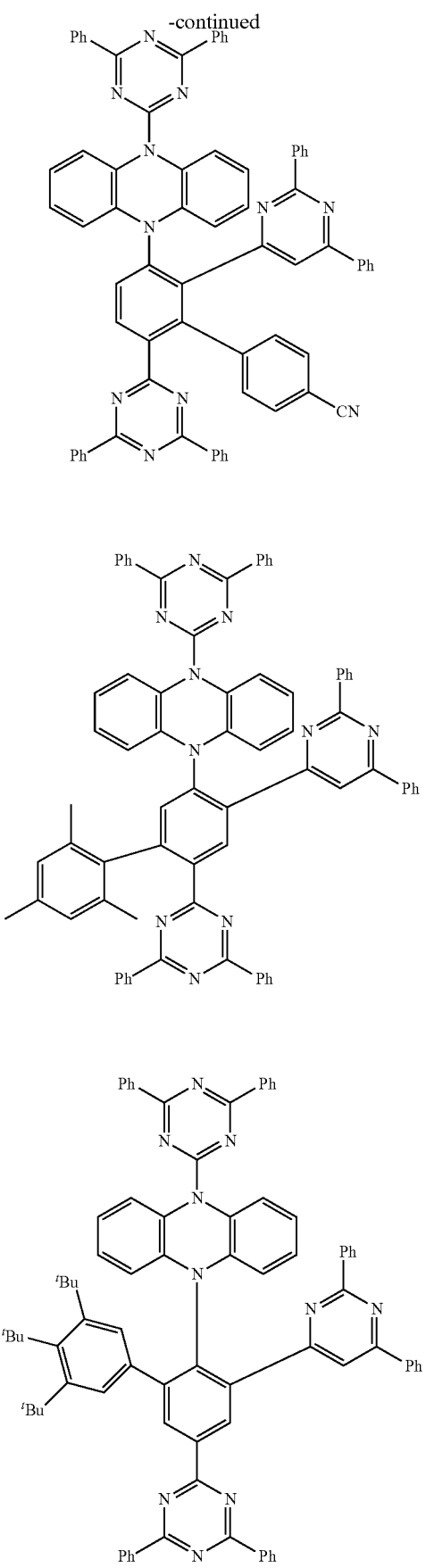
124
-continued
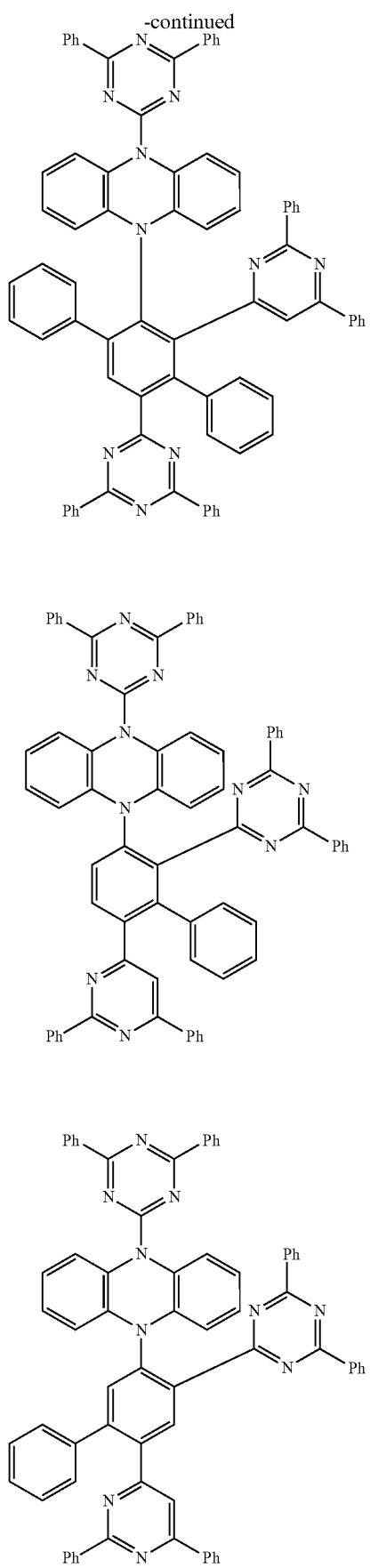

-continued
125
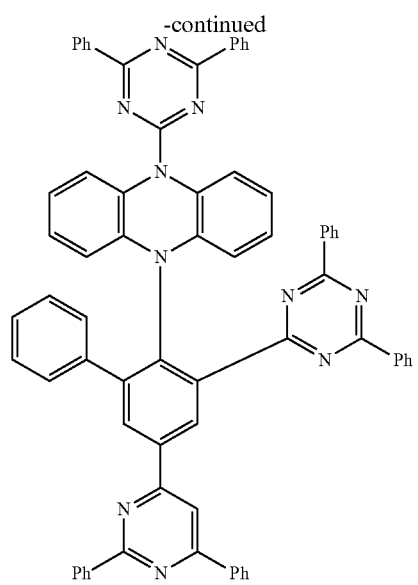
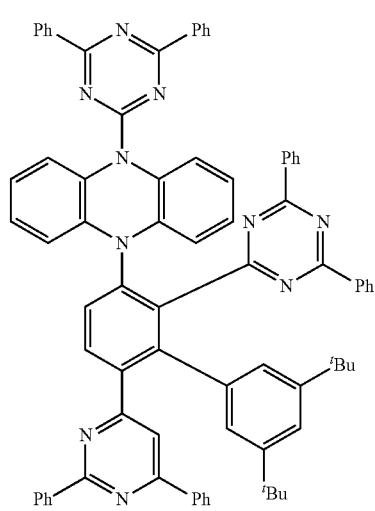
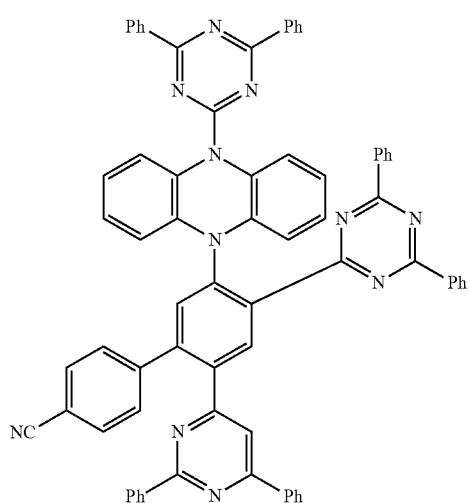
126
-continued
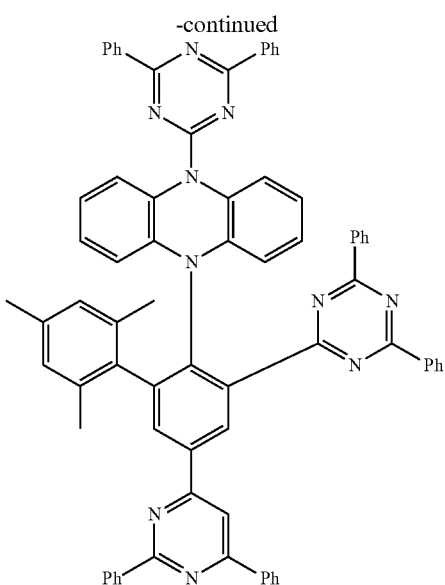
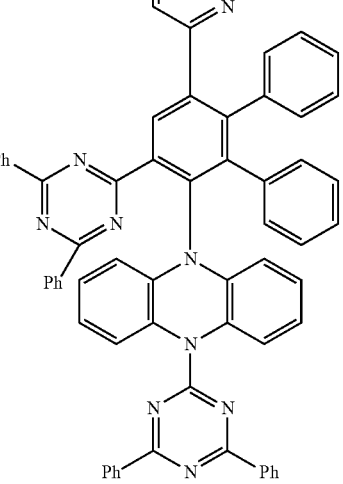

127
-continued
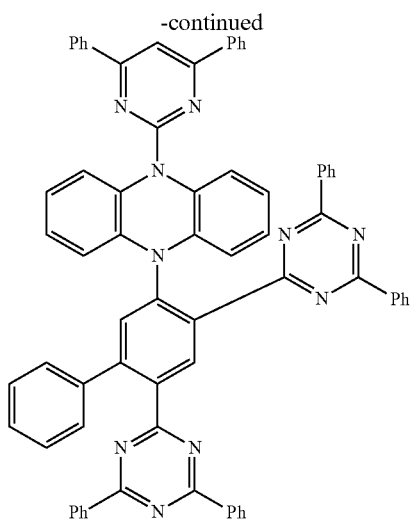
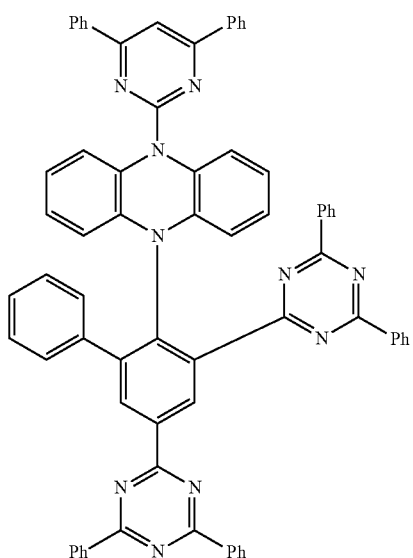
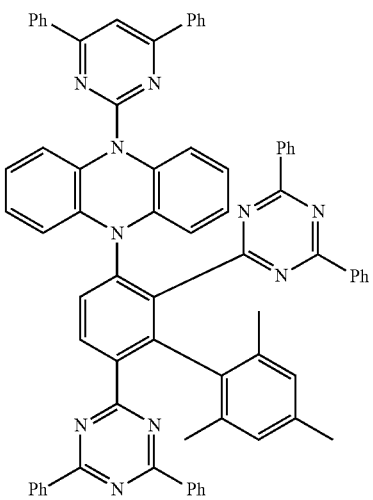
128
-continued
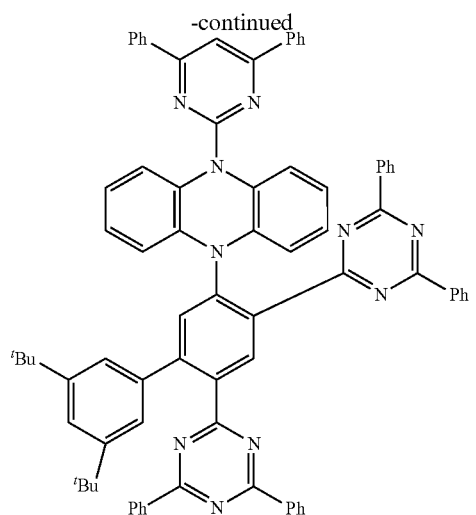
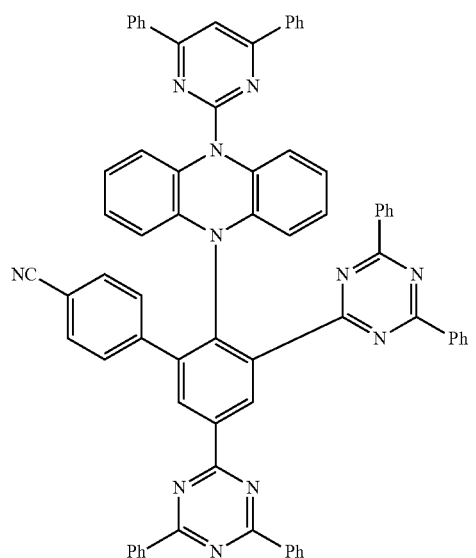
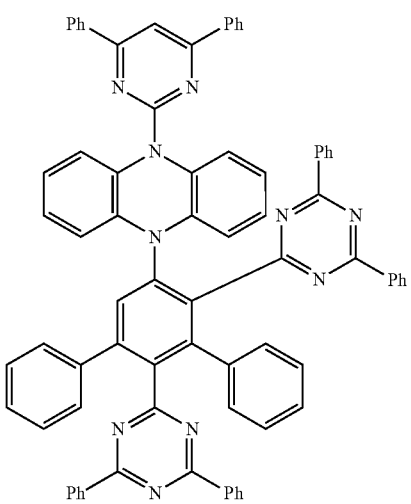 [SMILES: c1ccc(-c2cc(-c3ccccc3)nc(N3c4ccccc4N(c4cc(-c5ccccc5)c(-c5nc(-c6ccccc6)nc(-c6ccccc6)n5)c(-c5ccccc5)c4-c4nc(-c5ccccc5)nc(-c5ccccc5)n4)c4ccccc43)n2)cc1]

129
-continued
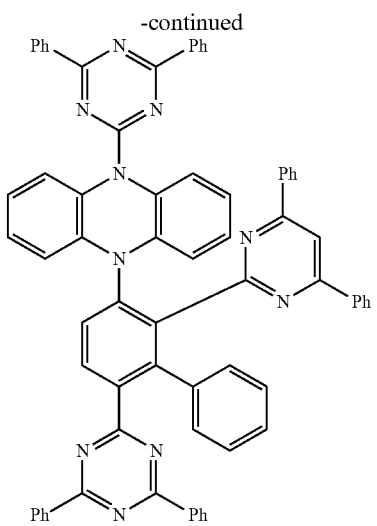
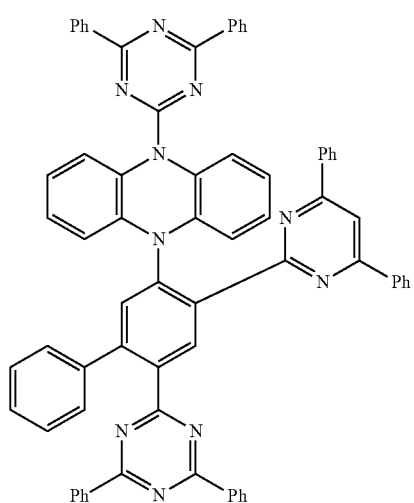
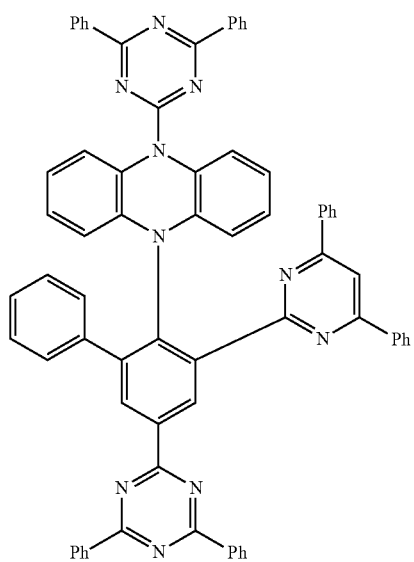 [SMILES: c1ccc(-c2cc(-c3ccccc3)nc(-c3c(-c4ccccc4)c(-c4nc(-c5ccccc5)nc(-c5ccccc5)n4)cc(-c4ccccc4)c3N3c4ccccc4N(c4nc(-c5ccccc5)nc(-c5ccccc5)n4)c4ccccc43)n2)cc1]
130
-continued
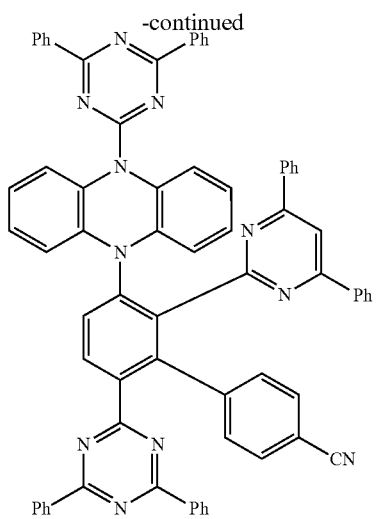
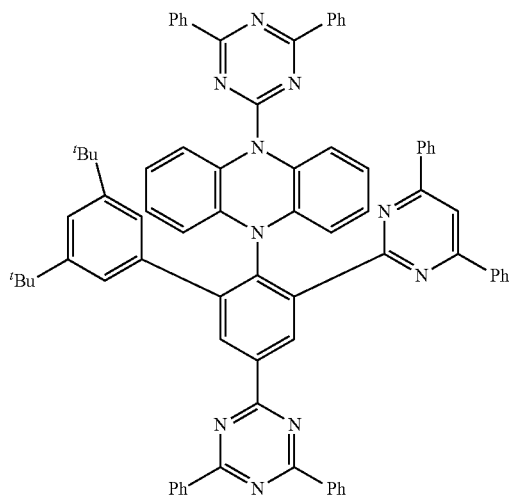
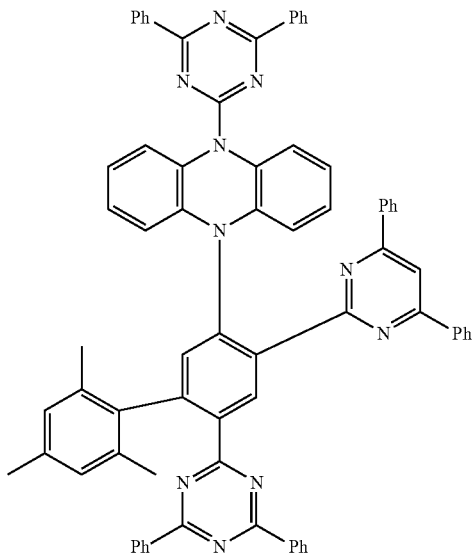

131
-continued
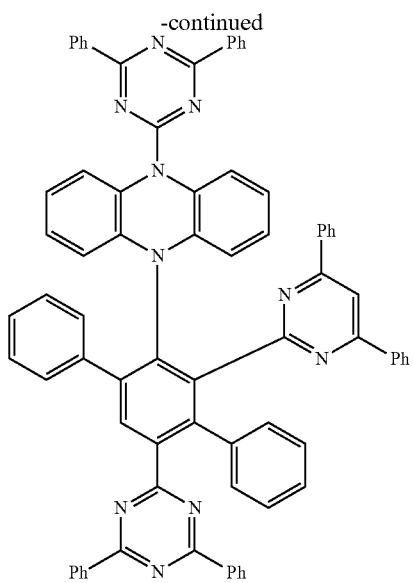
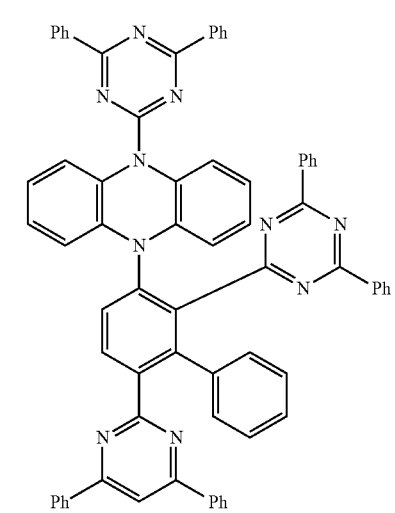
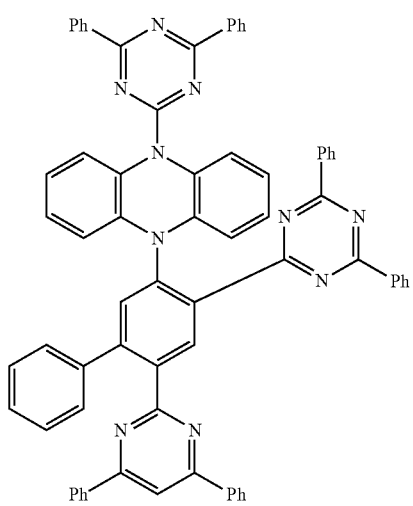
132
-continued
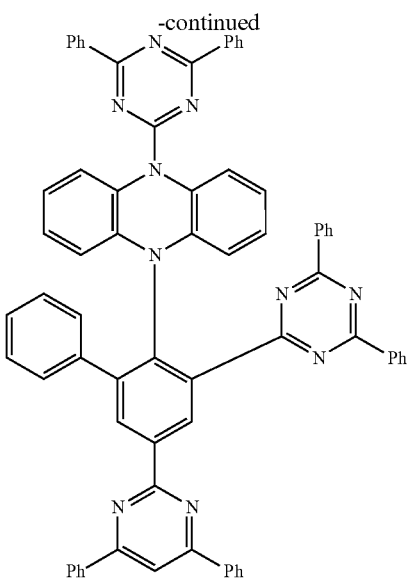
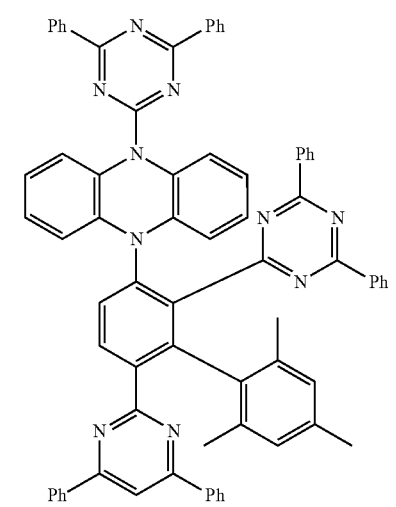
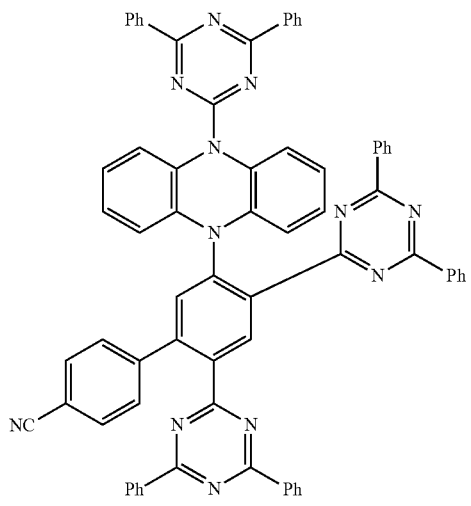

-continued
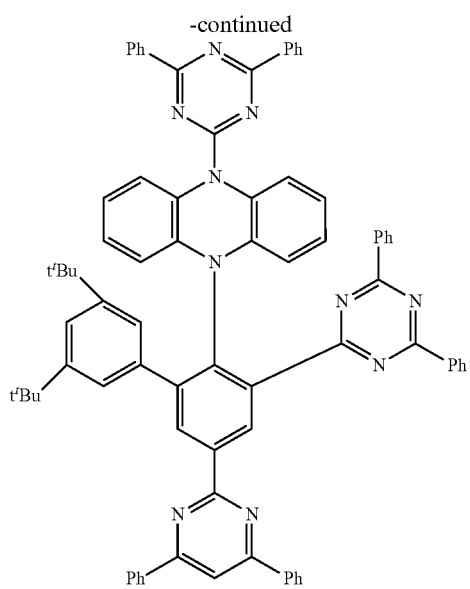
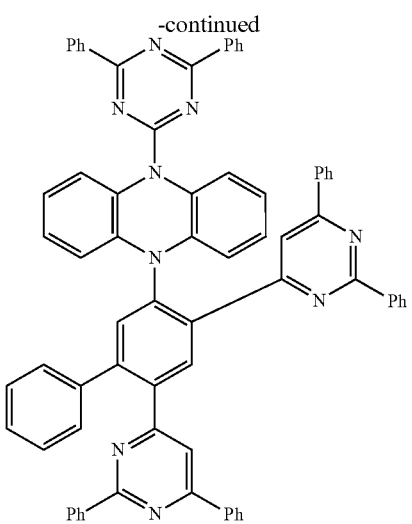
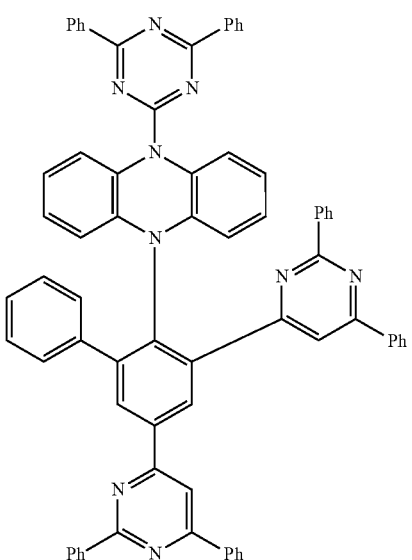
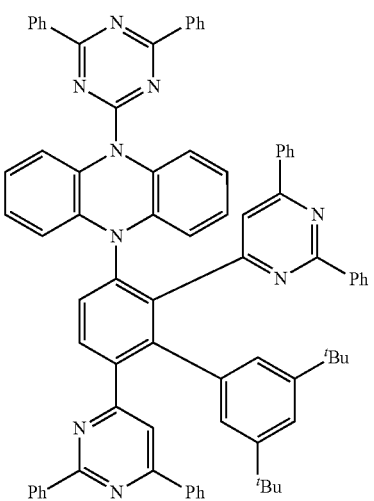

135
-continued
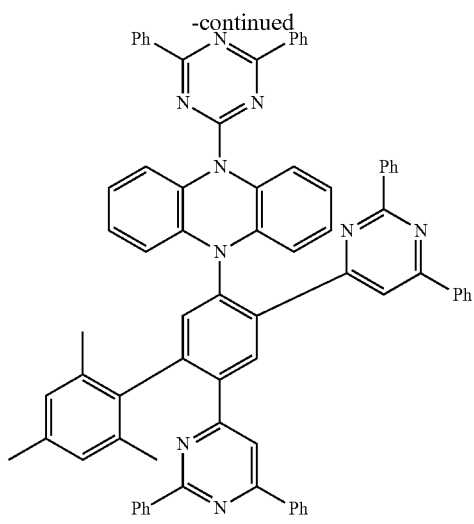
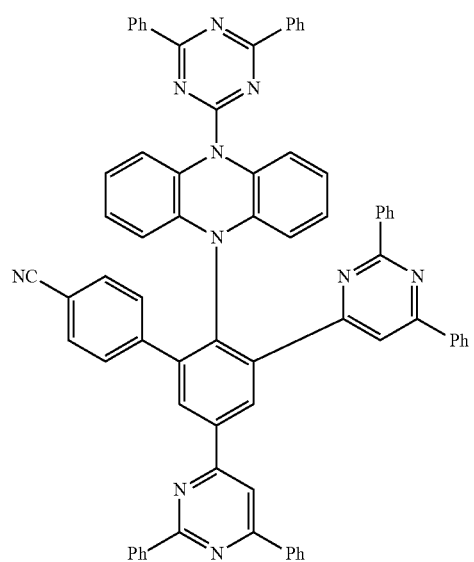
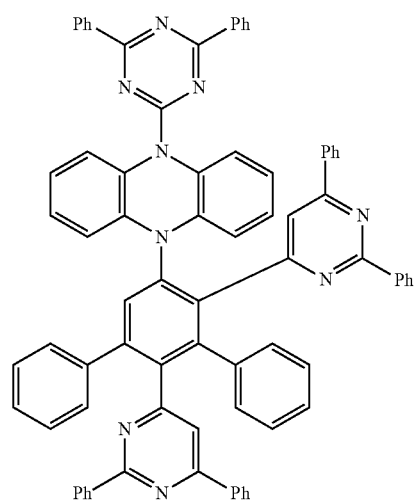 [SMILES: c1ccc(-c2cc(-c3c(-c4ccccc4)cc(N4c5ccccc5N(c5nc(-c6ccccc6)nc(-c6ccccc6)n5)c5ccccc54)c(-c4cc(-c5ccccc5)nc(-c5ccccc5)n4)c3-c3ccccc3)nc(-c3ccccc3)n2)cc1]
136
-continued
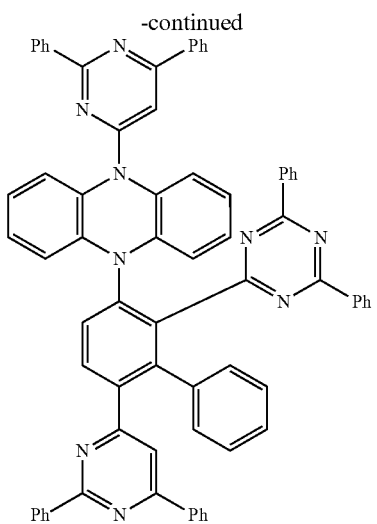
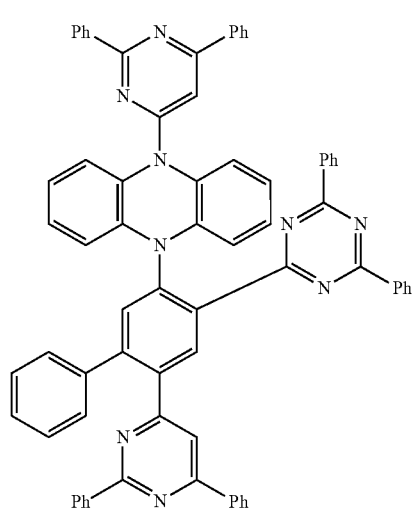
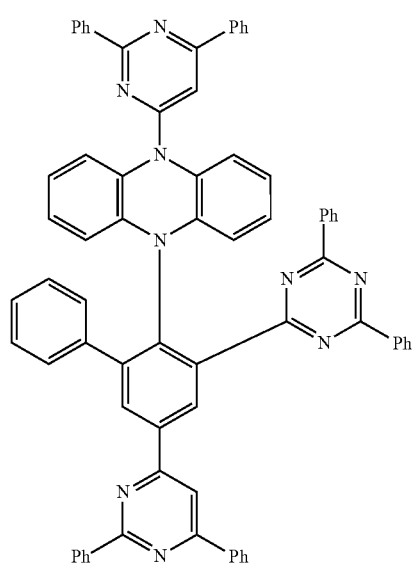 [SMILES: c1ccc(-c2cc(-c3cc(-c4ccccc4)c(N4c5ccccc5N(c5cc(-c6ccccc6)nc(-c6ccccc6)n5)c5ccccc54)c(-c4nc(-c5ccccc5)nc(-c5ccccc5)n4)c3-c3ccccc3)nc(-c3ccccc3)n2)cc1]

137
-continued
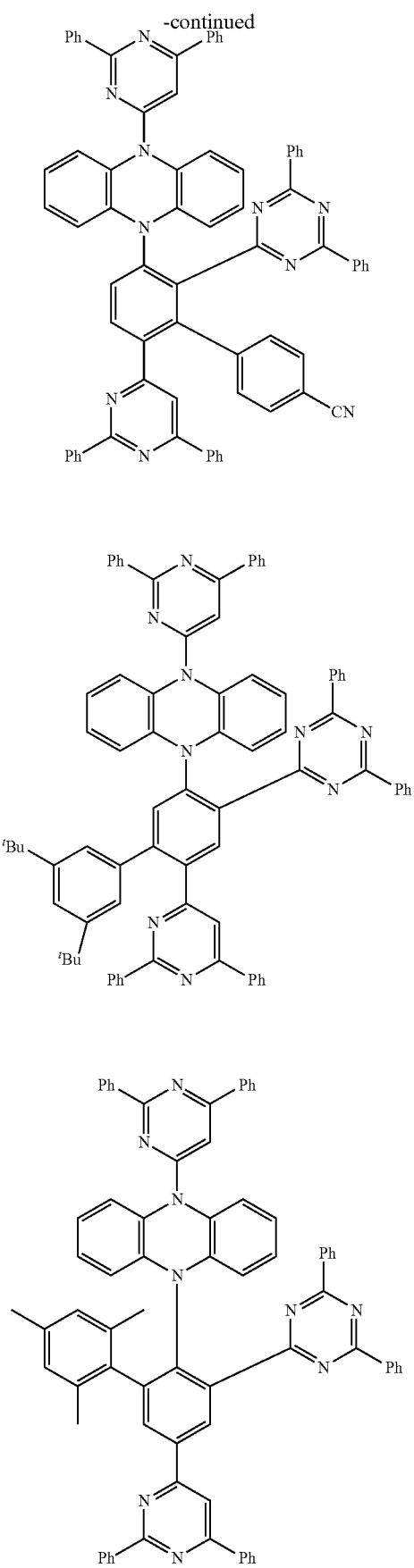
138
-continued
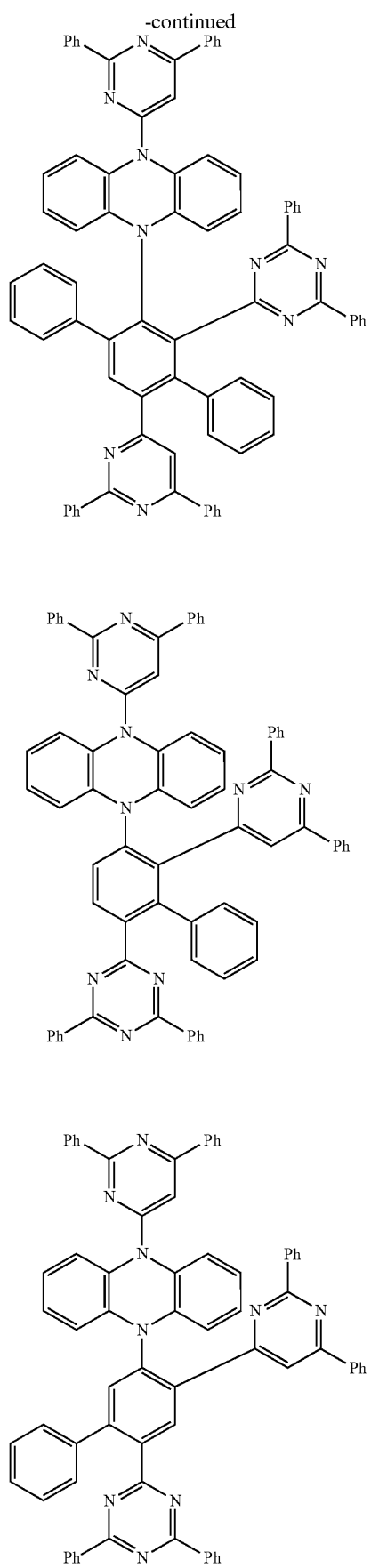

-continued
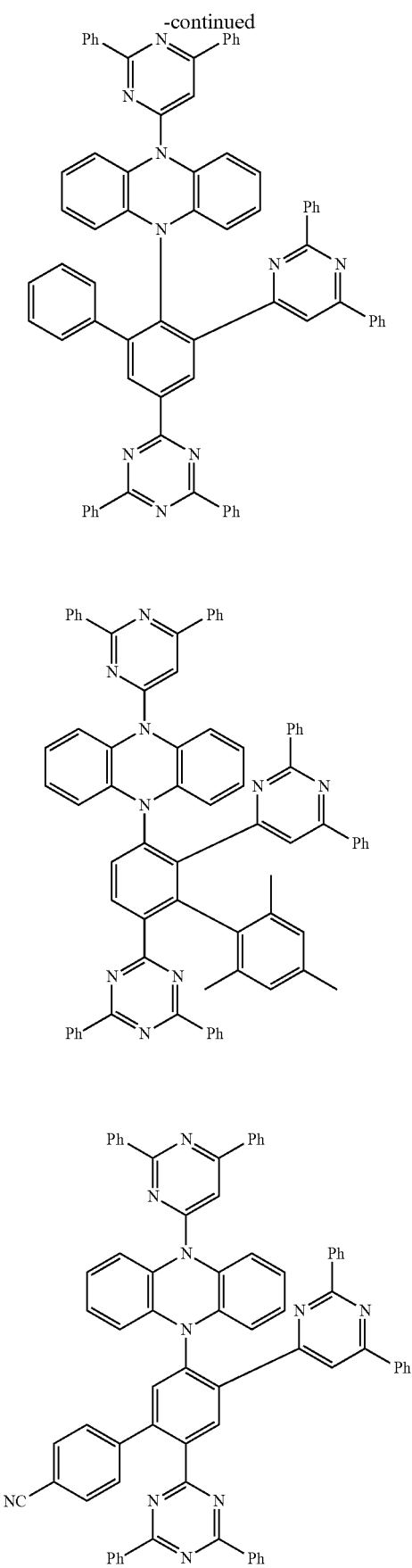
-continued
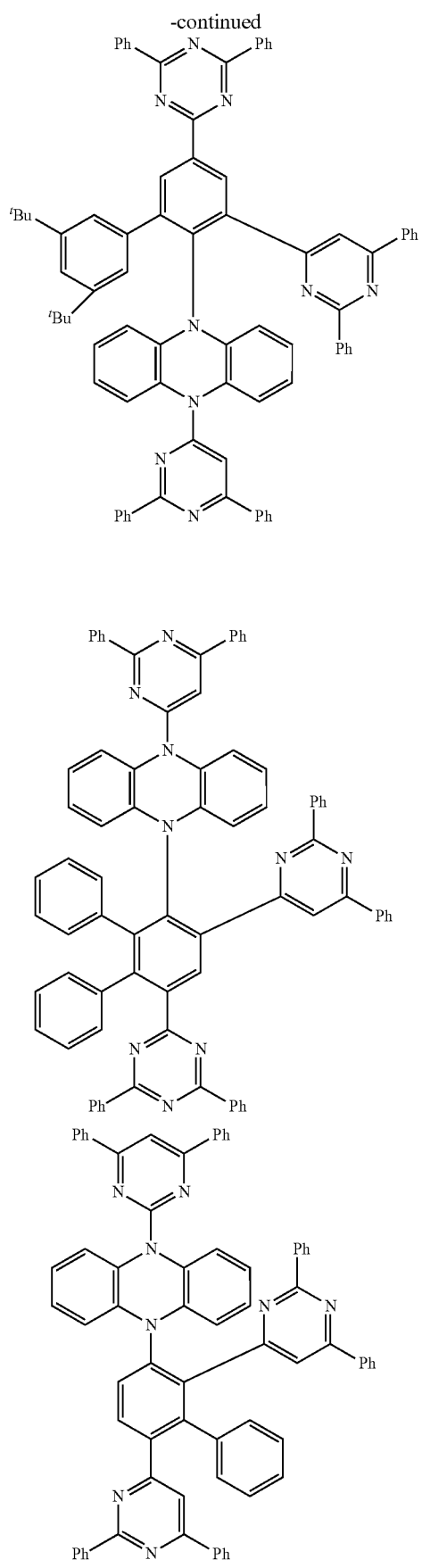

141
-continued
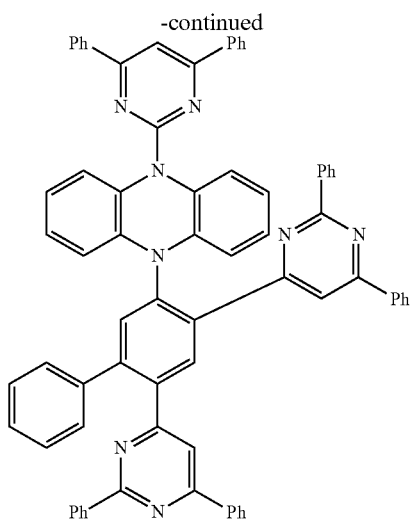
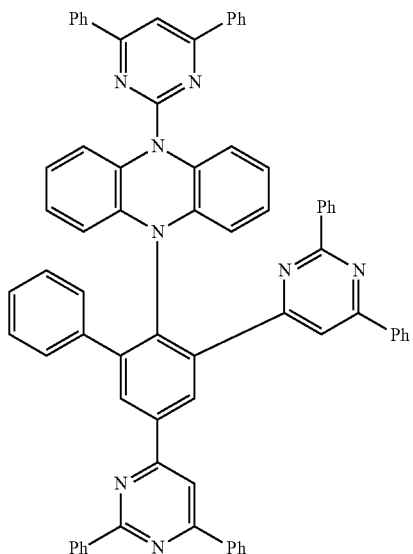
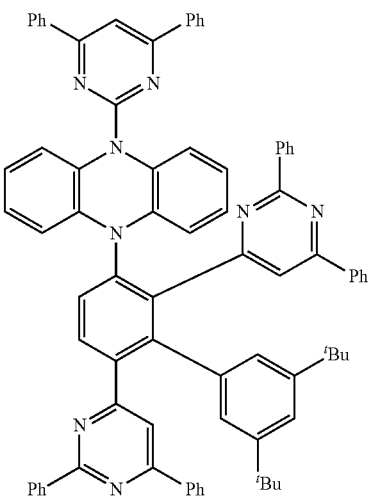
142
-continued
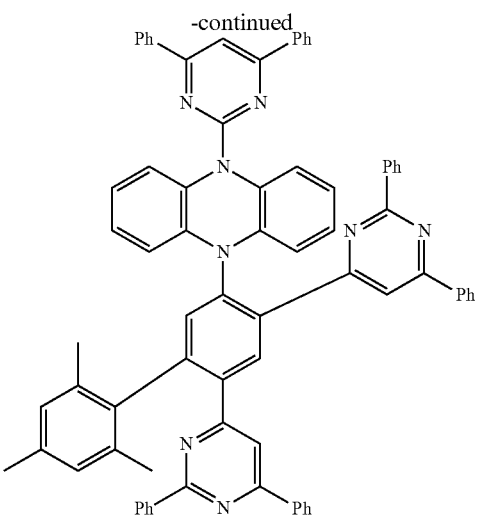
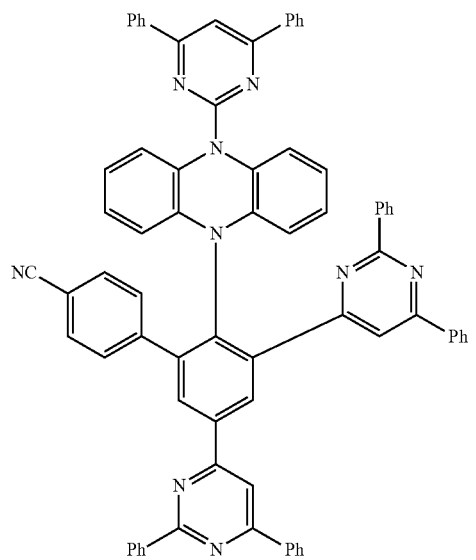
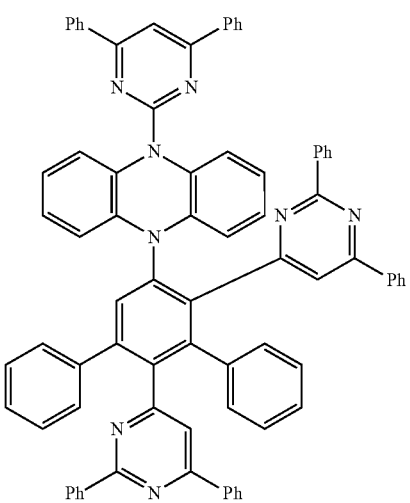 [SMILES: c1ccc(-c2cc(-c3c(-c4ccccc4)cc(N4c5ccccc5N(c5nc(-c6ccccc6)cc(-c6ccccc6)n5)c5ccccc54)c(-c4cc(-c5ccccc5)nc(-c5ccccc5)n4)c3-c3ccccc3)nc(-c3ccccc3)n2)cc1]

-continued
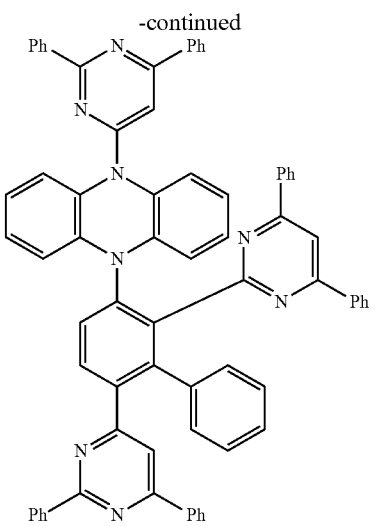
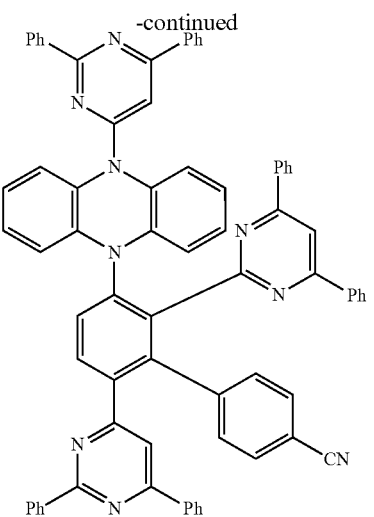
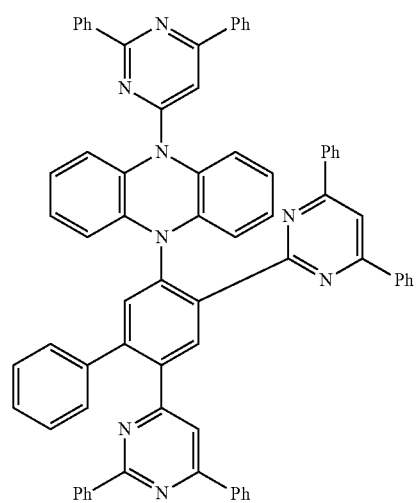
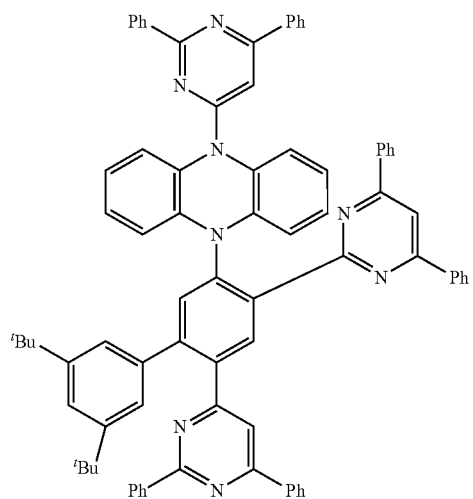
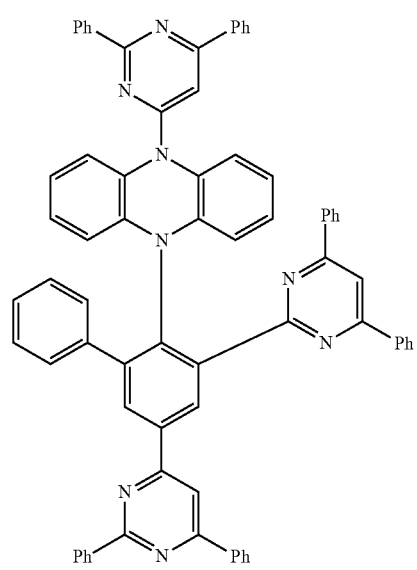 [SMILES: c1ccc(-c2cc(-c3cc(-c4ccccc4)c(N4c5ccccc5N(c5cc(-c6ccccc6)nc(-c6ccccc6)n5)c5ccccc54)c(-c4nc(-c5ccccc5)cc(-c5ccccc5)n4)c3-c3ccccc3)nc(-c3ccccc3)n2)cc1]
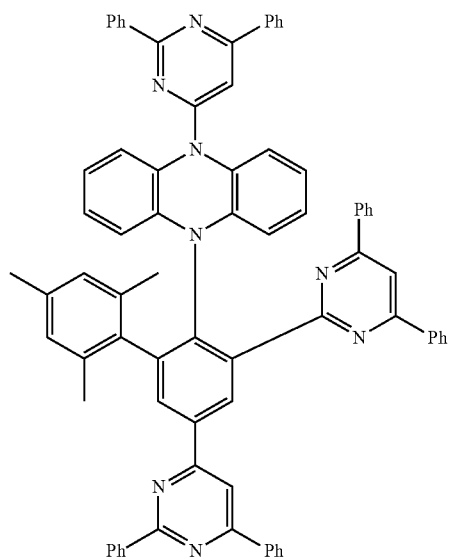

-continued
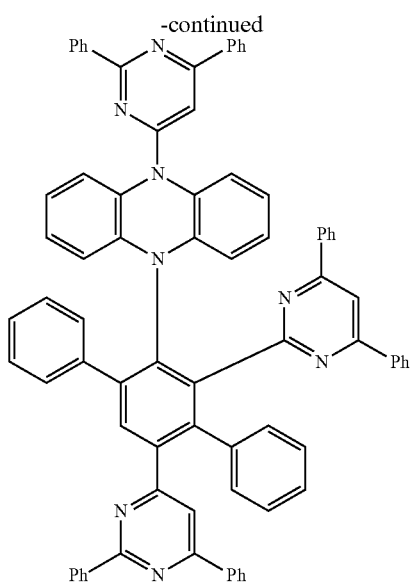
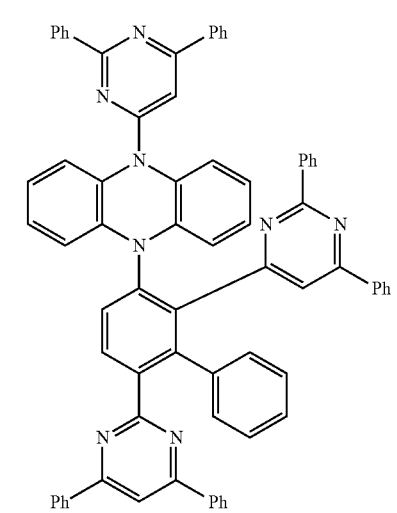
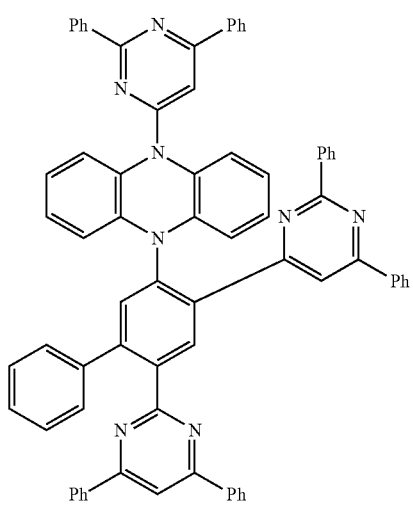
-continued
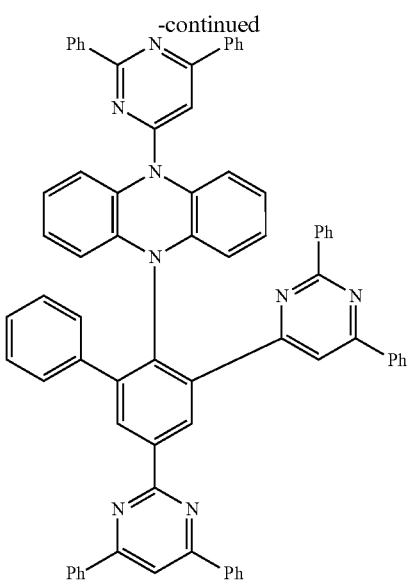
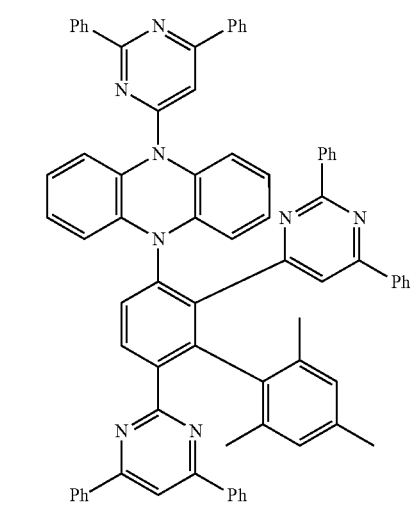
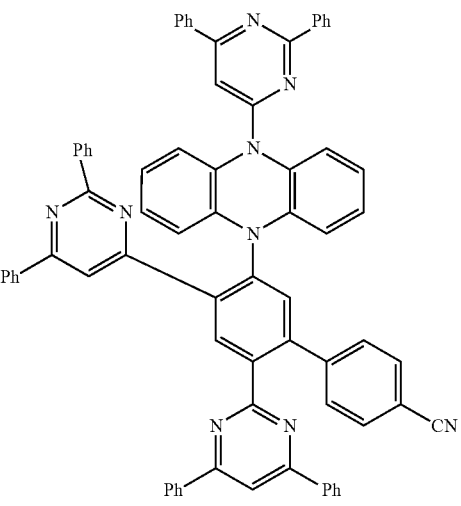

-continued
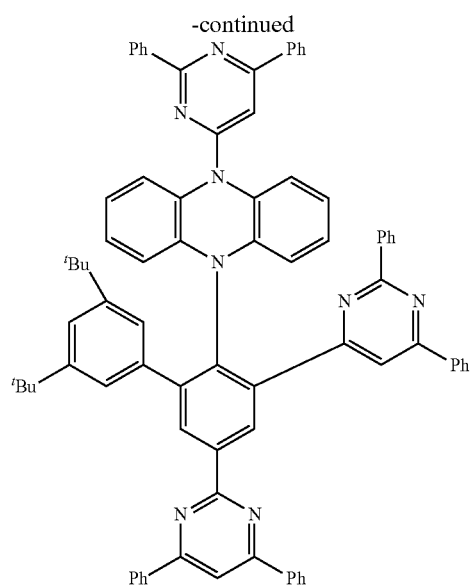
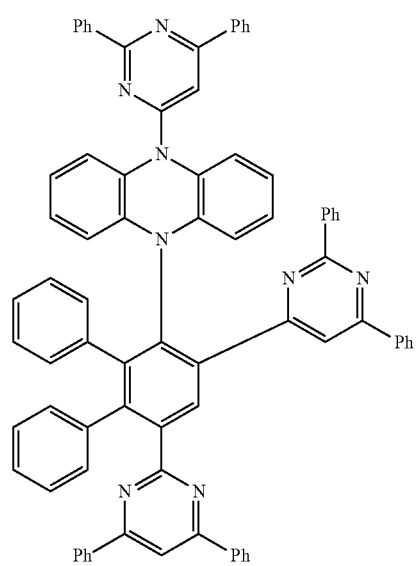 [SMILES: c1ccc(-c2cc(-c3cc(-c4nc(-c5ccccc5)cc(-c5ccccc5)n4)c(-c4ccccc4)c(-c4ccccc4)c3N3c4ccccc4N(c4cc(-c5ccccc5)nc(-c5ccccc5)n4)c4ccccc43)nc(-c3ccccc3)n2)cc1]
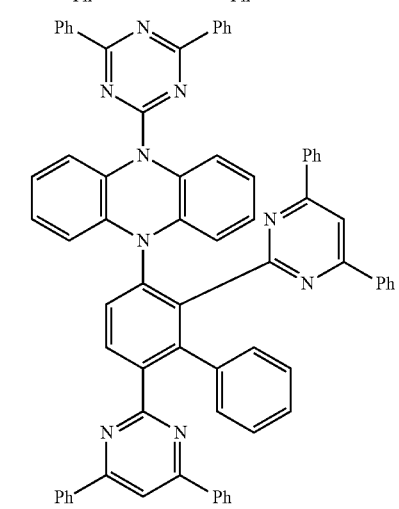
-continued
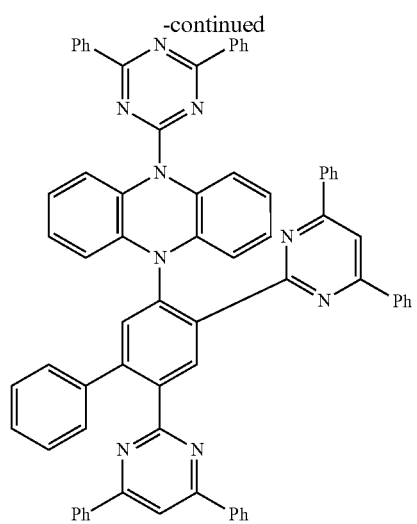
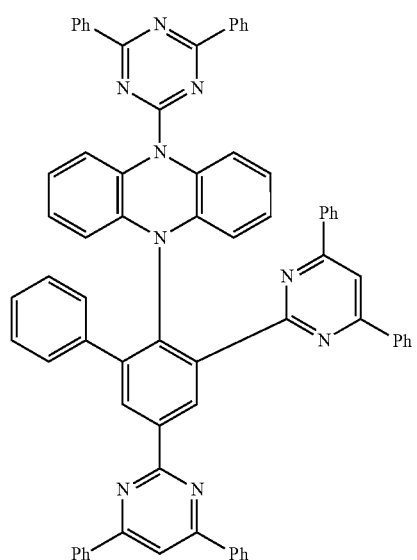
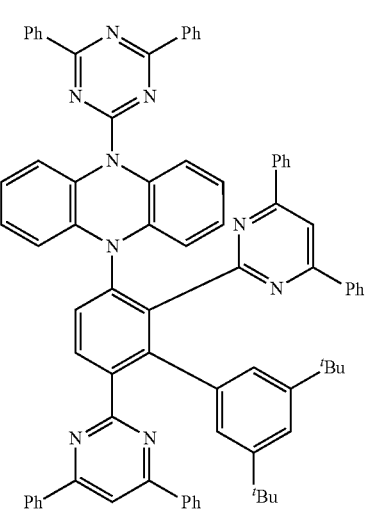

149
-continued
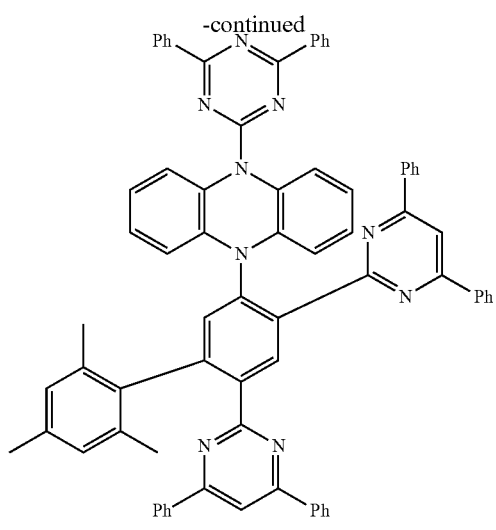
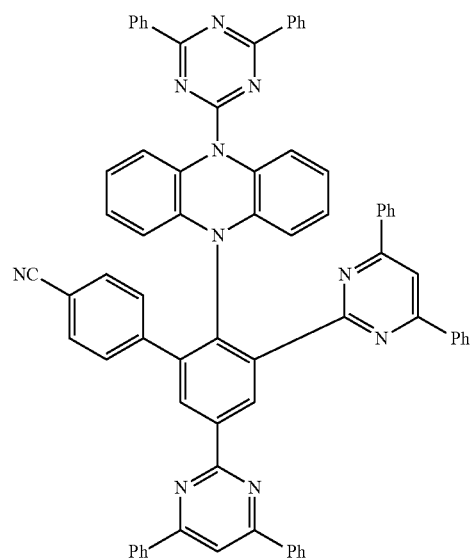
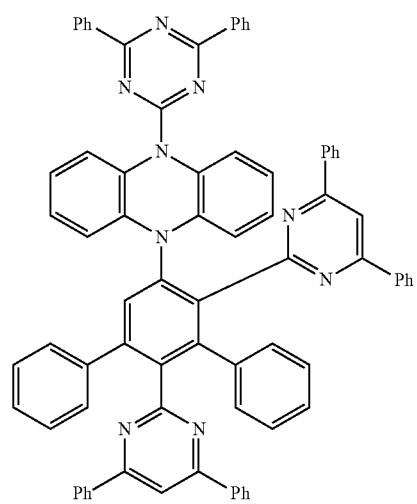 [SMILES: c1ccc(-c2cc(-c3ccccc3)nc(-c3c(-c4ccccc4)cc(N4c5ccccc5N(c5nc(-c6ccccc6)nc(-c6ccccc6)n5)c5ccccc54)c(-c4nc(-c5ccccc5)cc(-c5ccccc5)n4)c3-c3ccccc3)n2)cc1]
150
-continued
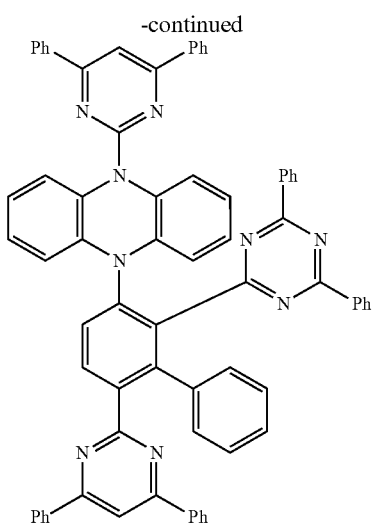
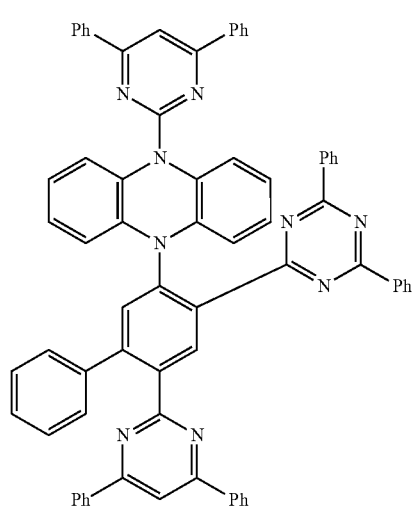
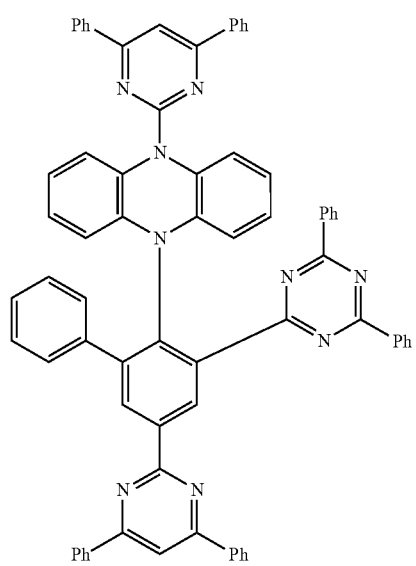

-continued
151
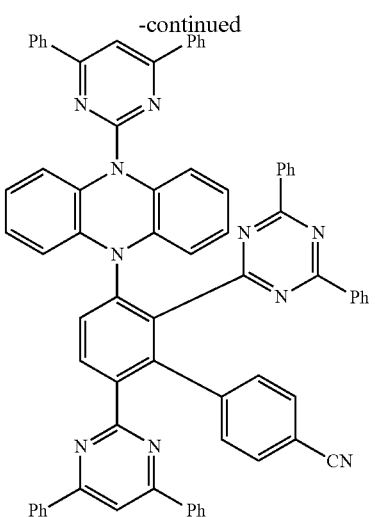
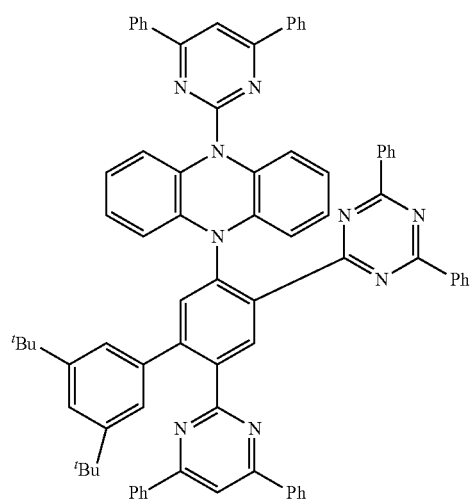
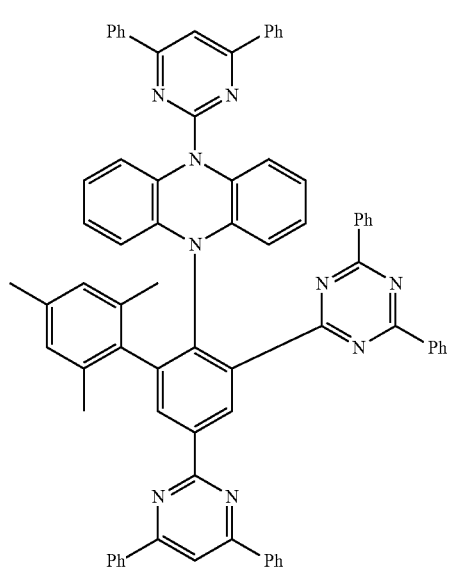
-continued
152
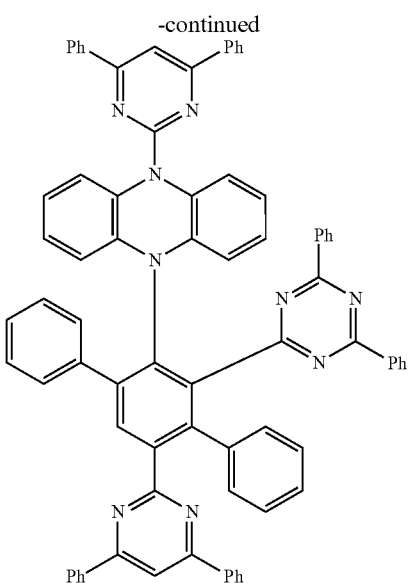
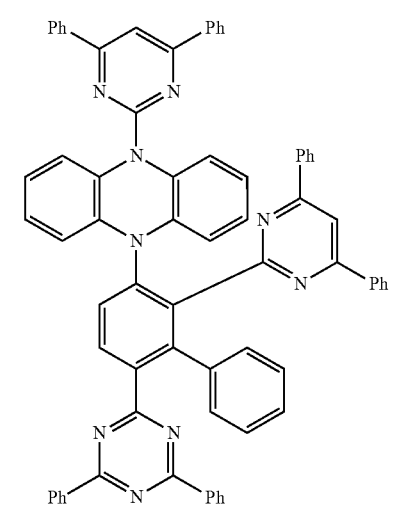
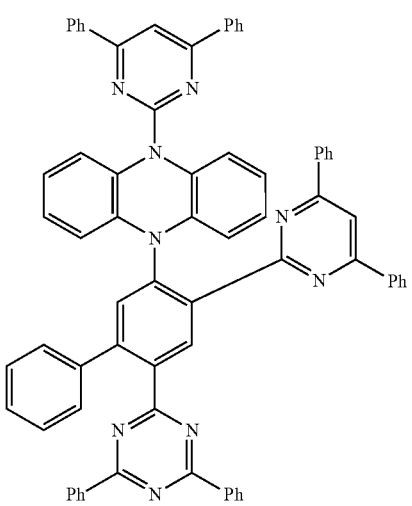

153
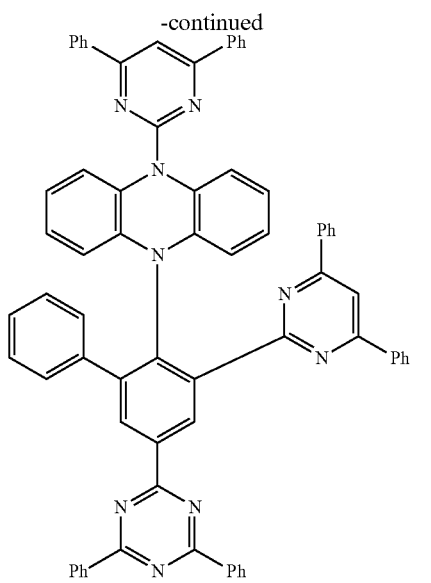
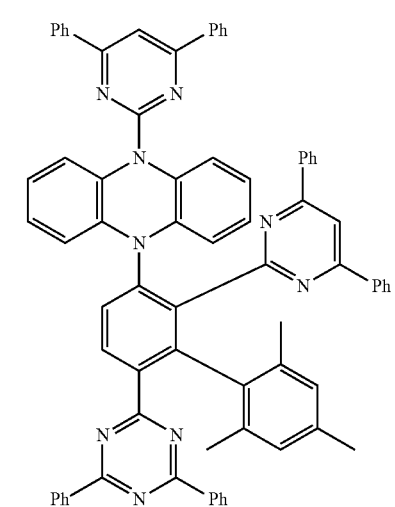
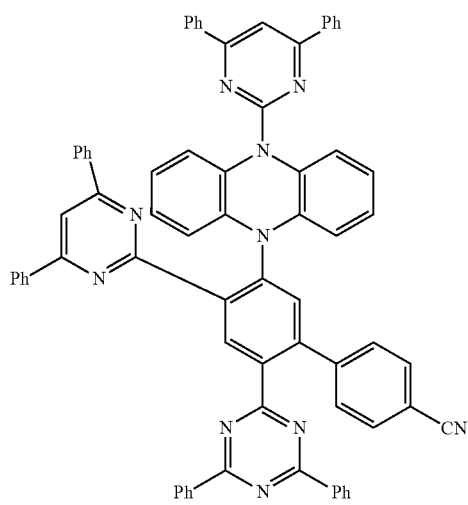
154
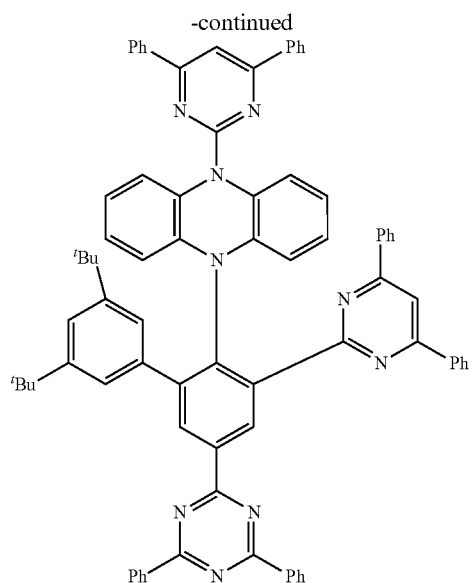
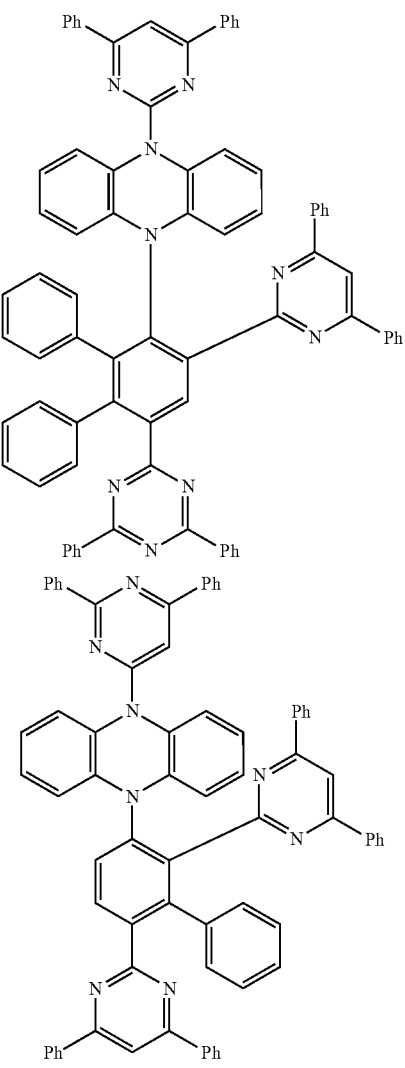

-continued
155
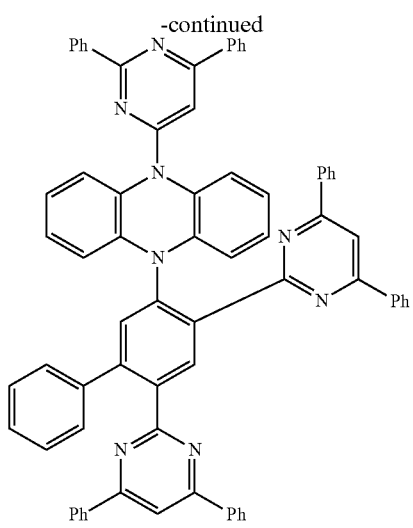
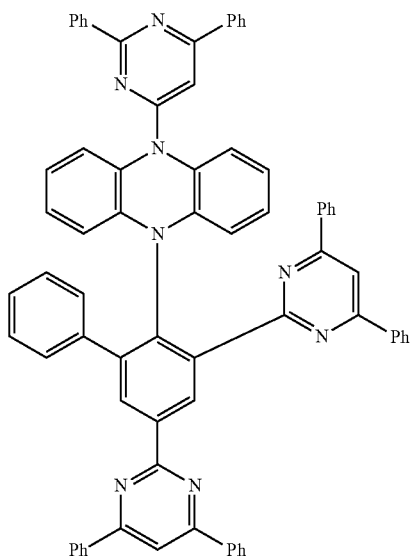
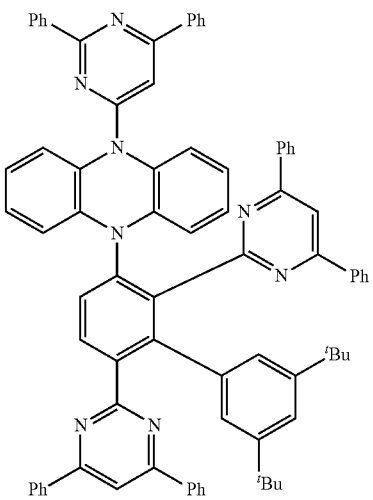
-continued
156
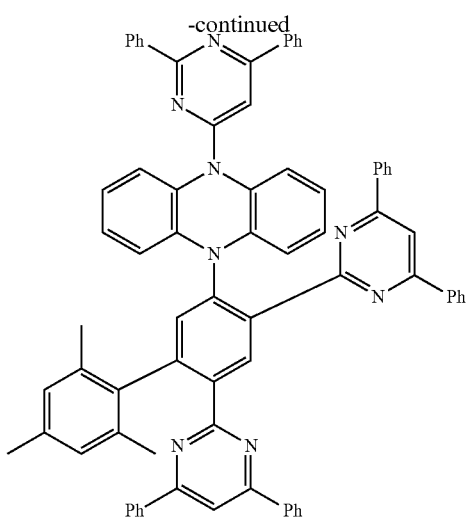
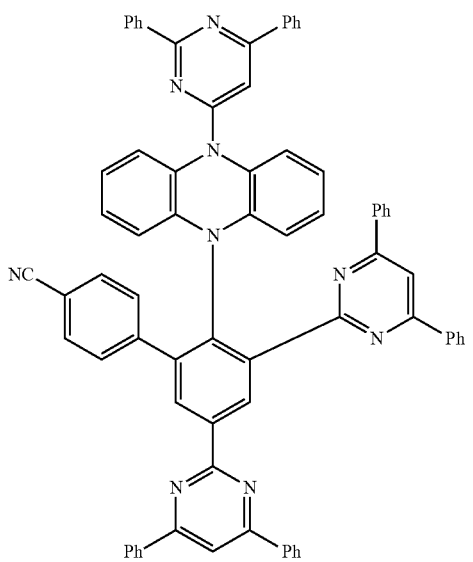
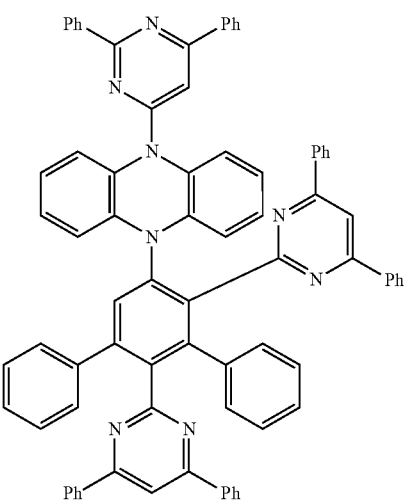 [SMILES: c1ccc(-c2cc(N3c4ccccc4N(c4cc(-c5ccccc5)c(-c5nc(-c6ccccc6)cc(-c6ccccc6)n5)c(-c5ccccc5)c4-c4nc(-c5ccccc5)cc(-c5ccccc5)n4)c4ccccc43)nc(-c3ccccc3)n2)cc1]

-continued
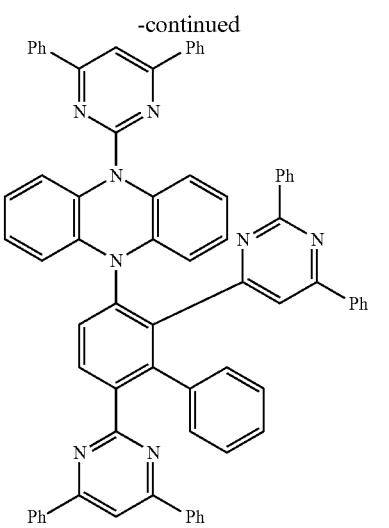
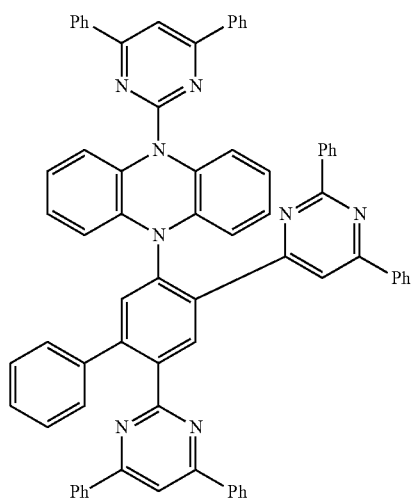
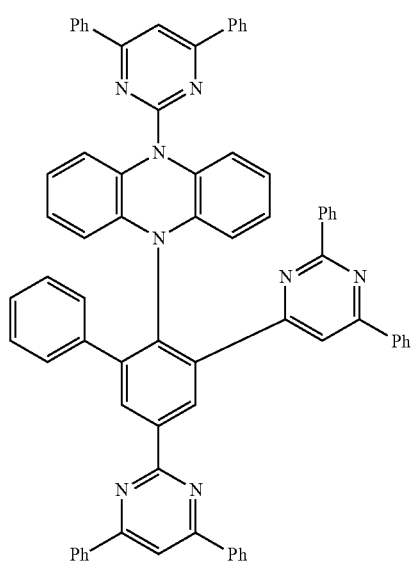 [SMILES: c1ccc(-c2cc(-c3c(-c4ccccc4)c(-c4nc(-c5ccccc5)cc(-c5ccccc5)n4)cc(-c4ccccc4)c3N3c4ccccc4N(c4nc(-c5ccccc5)cc(-c5ccccc5)n4)c4ccccc43)nc(-c3ccccc3)n2)cc1]
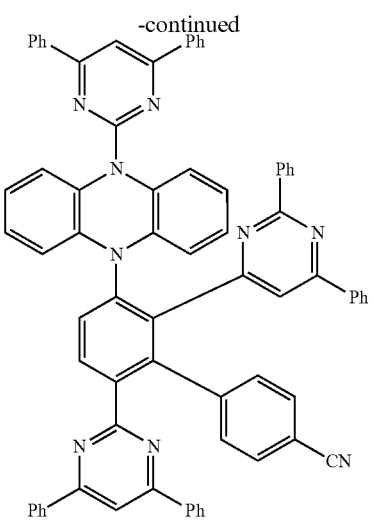
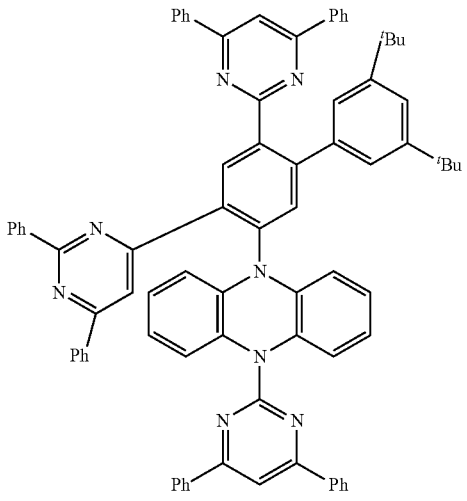
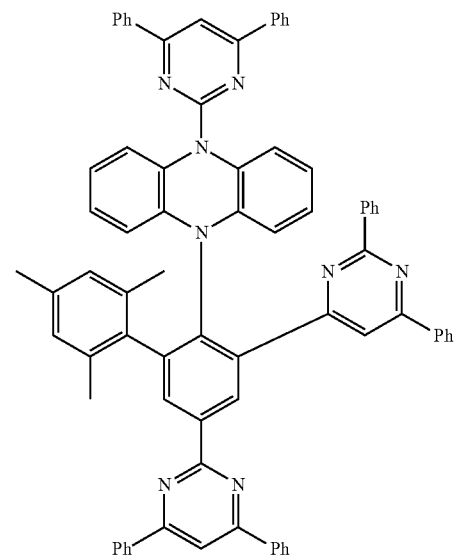

159
-continued
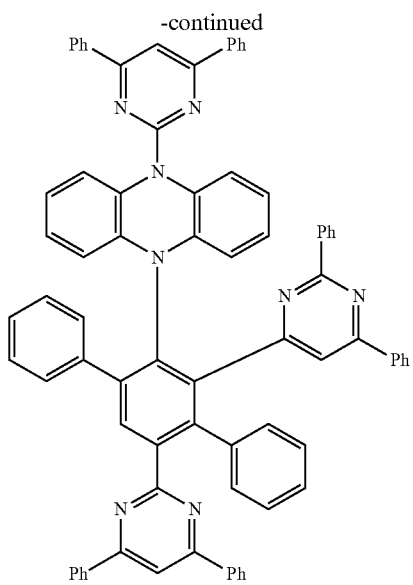
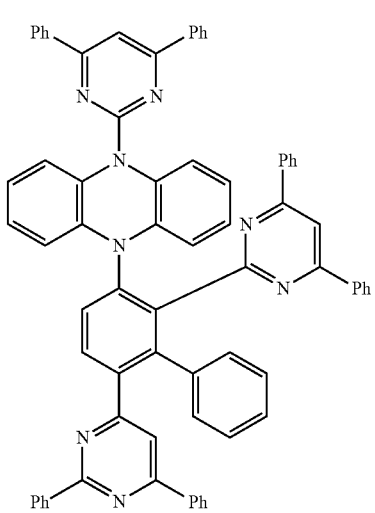
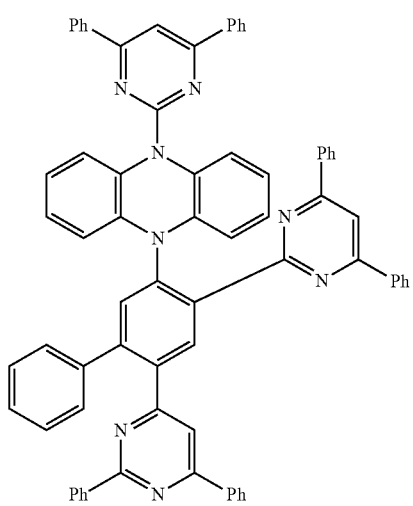
160
-continued
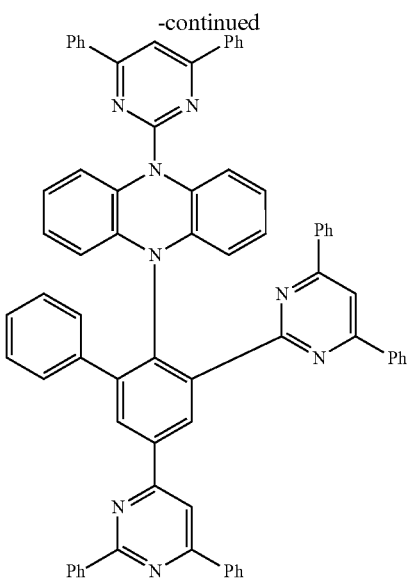
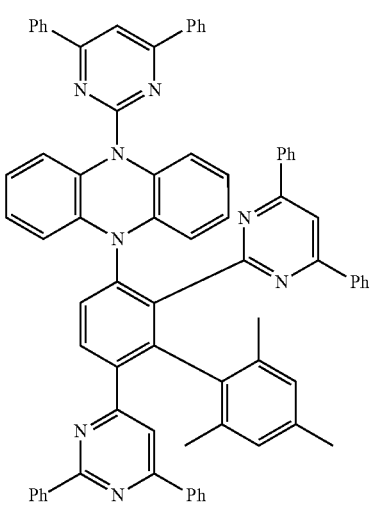
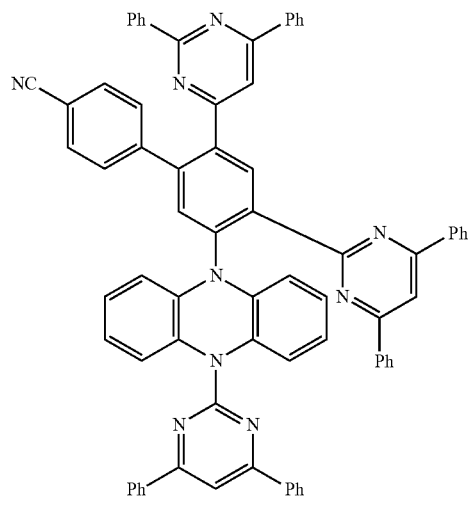

161
-continued
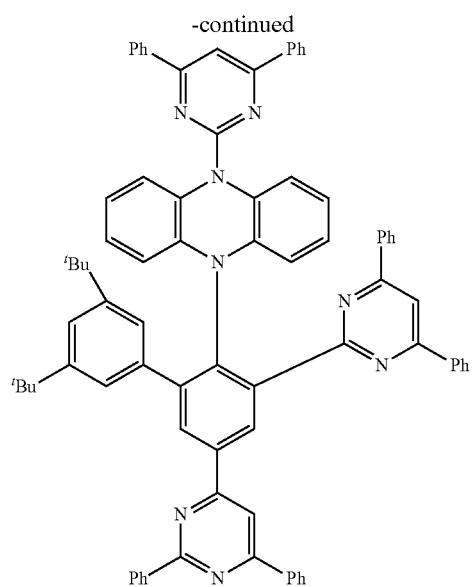
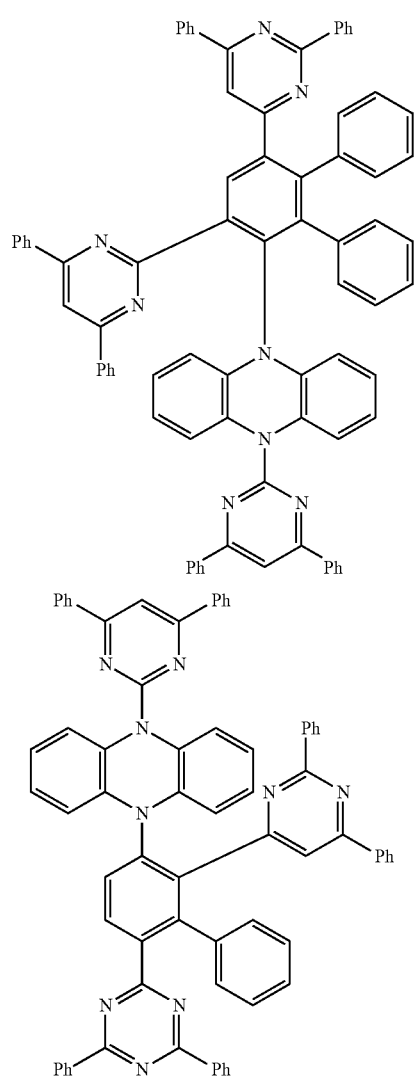
162
-continued
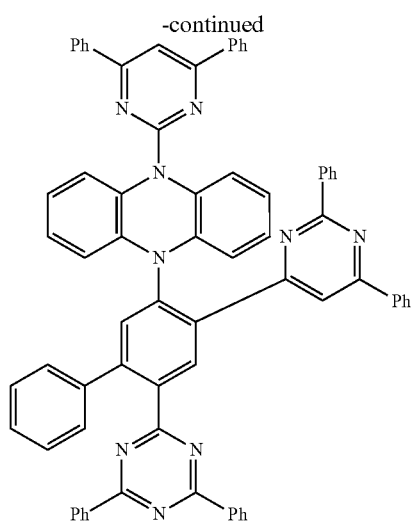
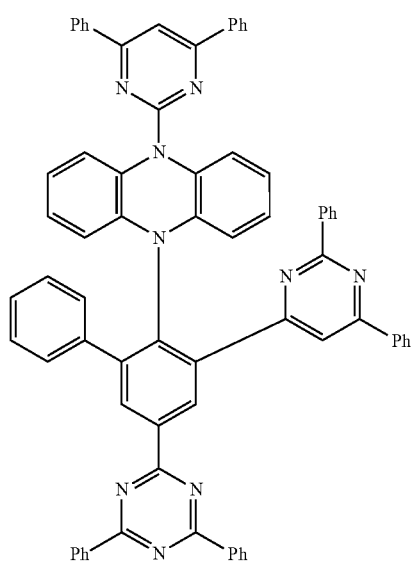
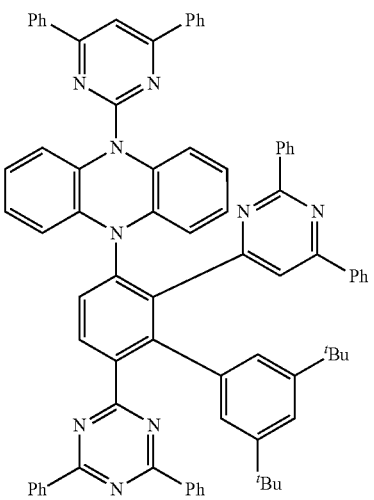

-continued
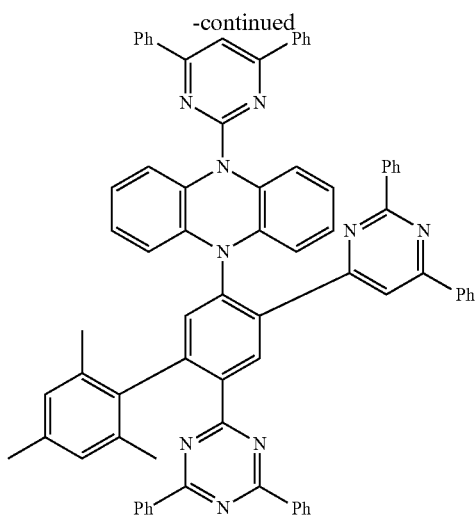
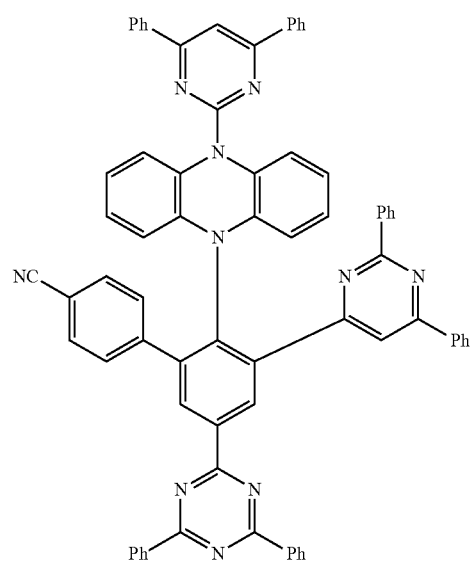
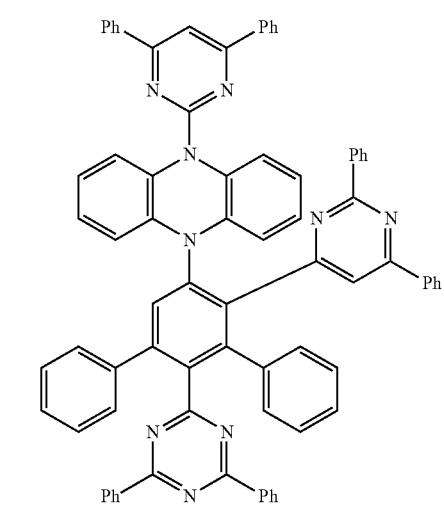 [SMILES: c1ccc(-c2cc(-c3c(N4c5ccccc5N(c5nc(-c6ccccc6)cc(-c6ccccc6)n5)c5ccccc54)cc(-c4ccccc4)c(-c4nc(-c5ccccc5)nc(-c5ccccc5)n4)c3-c3ccccc3)nc(-c3ccccc3)n2)cc1]
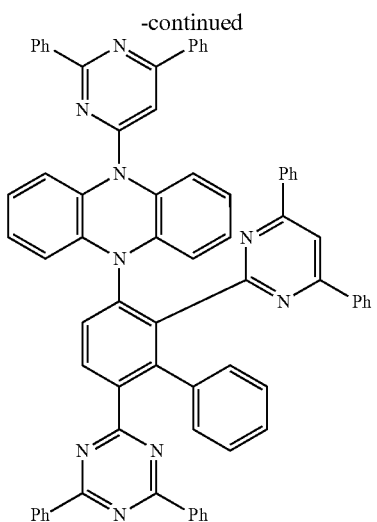
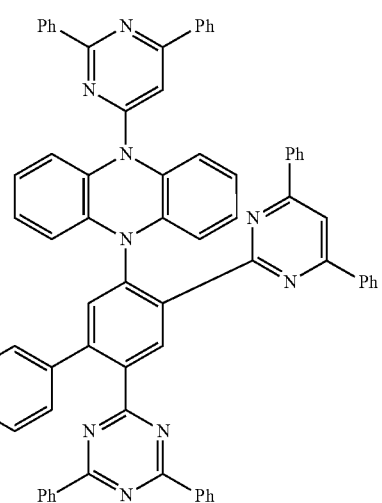
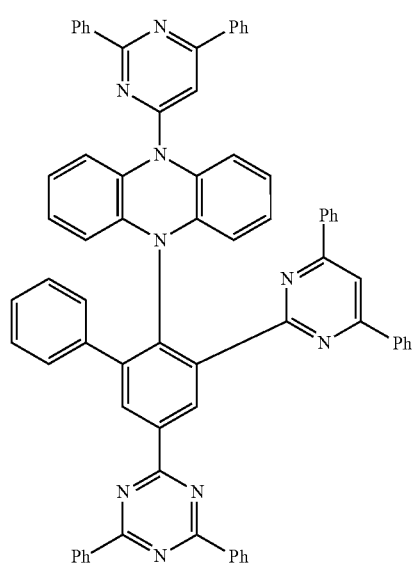 [SMILES: c1ccc(-c2cc(N3c4ccccc4N(c4c(-c5ccccc5)cc(-c5nc(-c6ccccc6)nc(-c6ccccc6)n5)c(-c5ccccc5)c4-c4nc(-c5ccccc5)cc(-c5ccccc5)n4)c4ccccc43)nc(-c3ccccc3)n2)cc1]

-continued
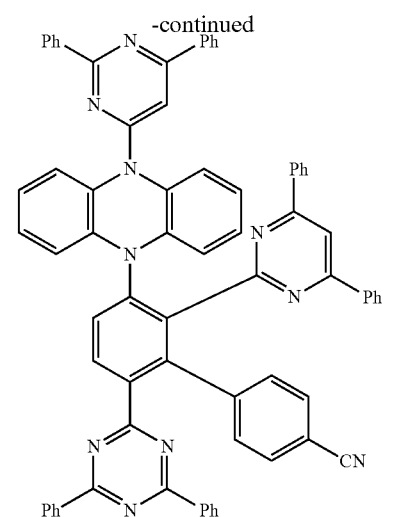
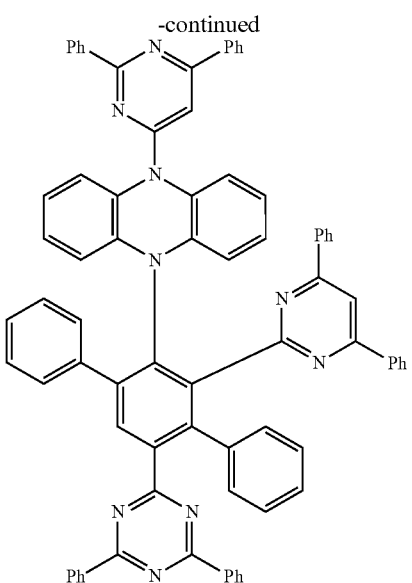
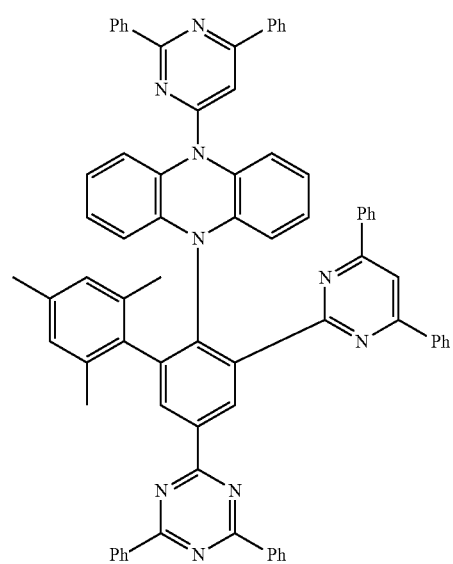
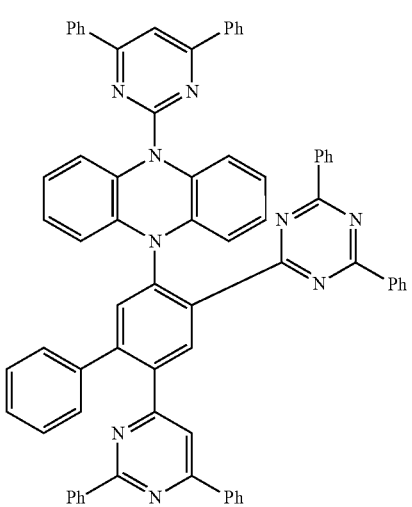

167
-continued
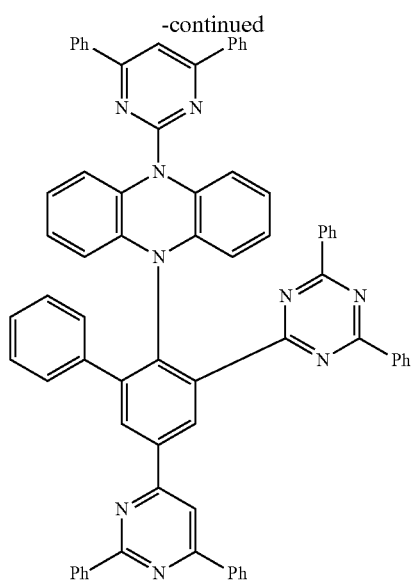
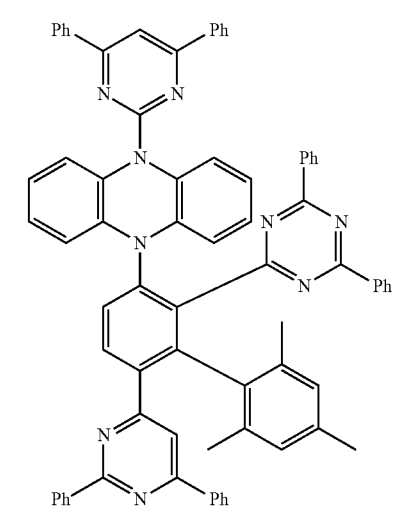
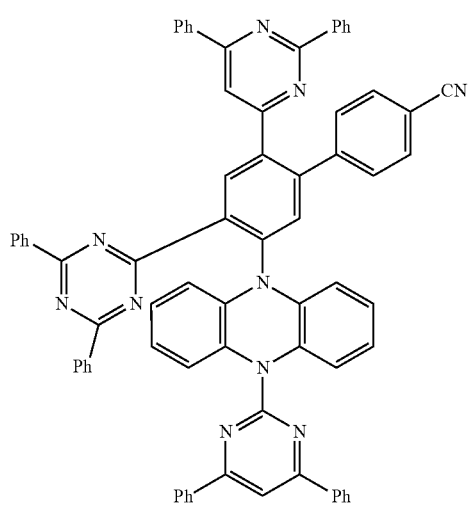
168
-continued
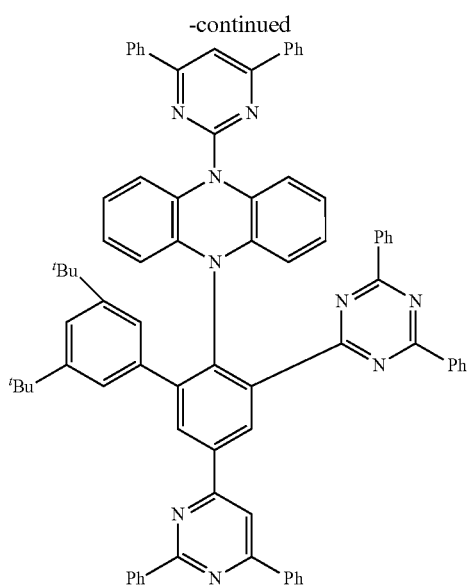
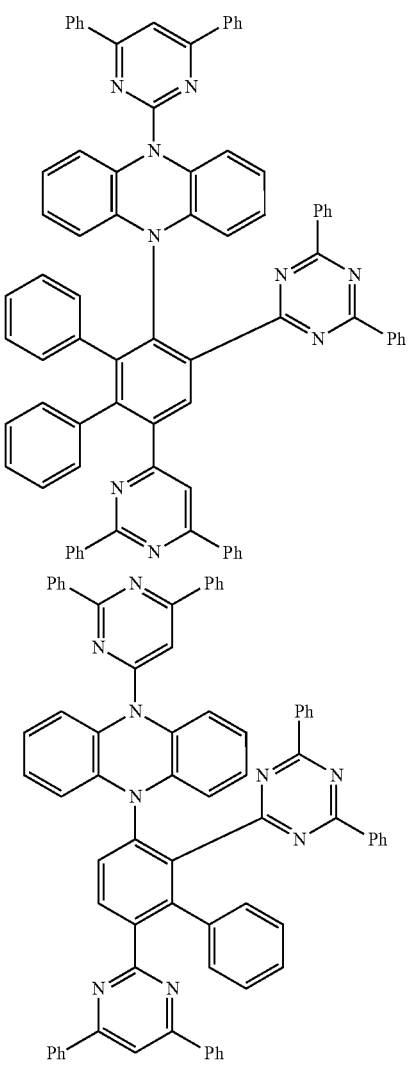

169
-continued
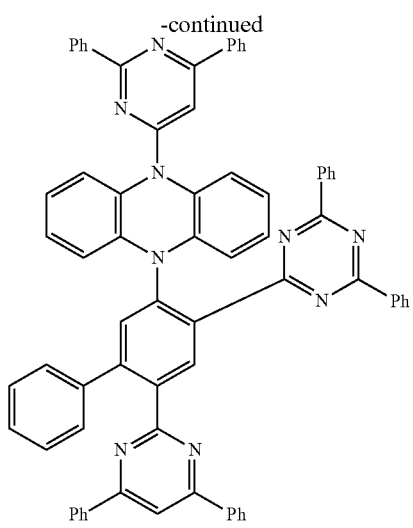
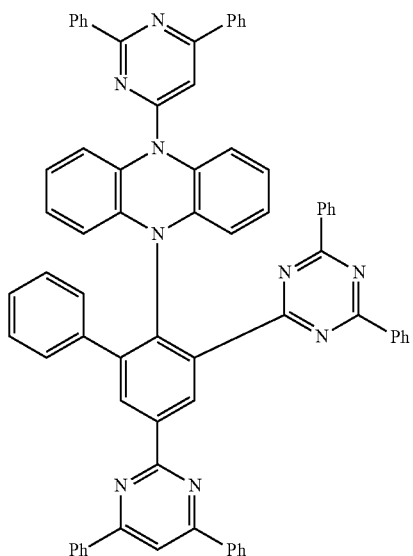
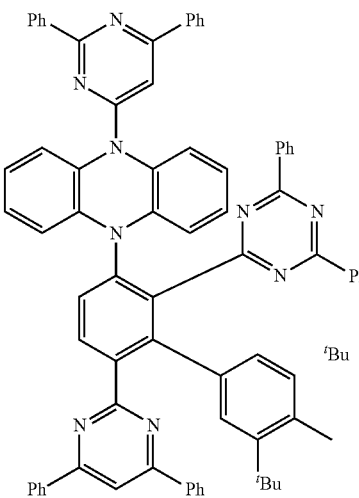
170
-continued
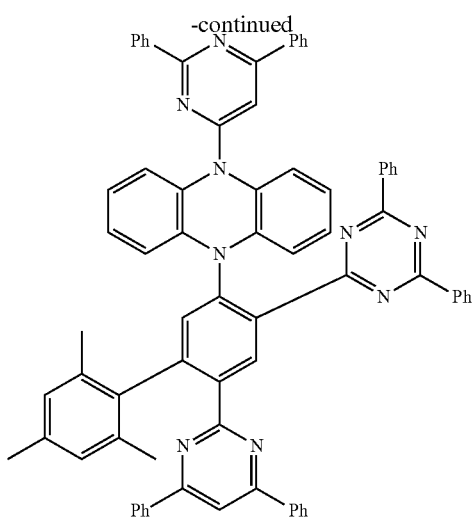
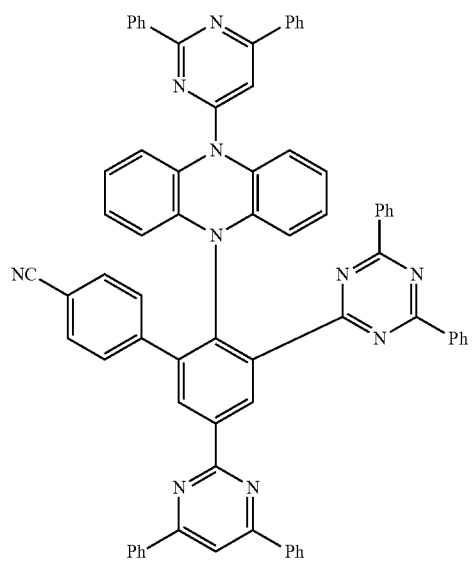
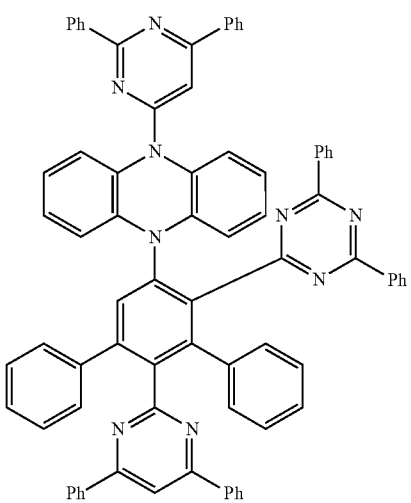 [SMILES: c1ccc(-c2cc(N3c4ccccc4N(c4cc(-c5ccccc5)c(-c5nc(-c6ccccc6)cc(-c6ccccc6)n5)c(-c5ccccc5)c4-c4nc(-c5ccccc5)nc(-c5ccccc5)n4)c4ccccc43)nc(-c3ccccc3)n2)cc1]

-continued
171
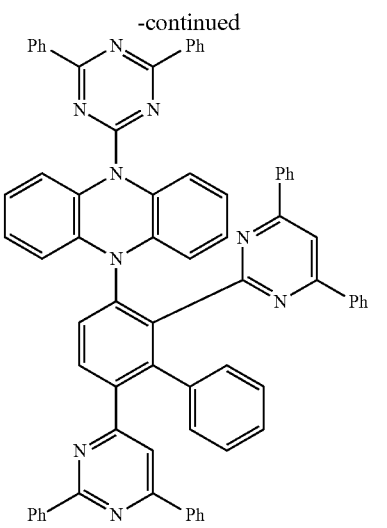
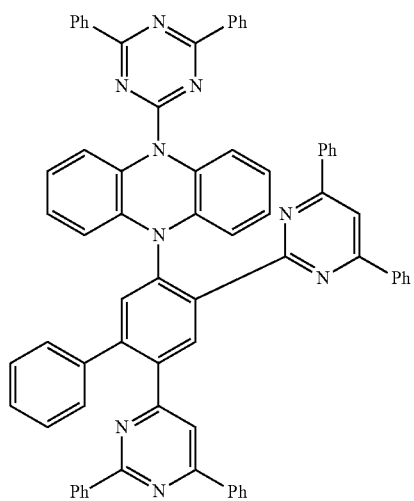
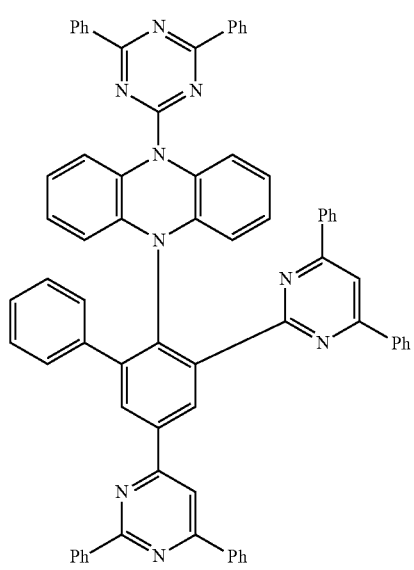 [SMILES: c1ccc(-c2cc(-c3cc(-c4ccccc4)c(N4c5ccccc5N(c5nc(-c6ccccc6)nc(-c6ccccc6)n5)c5ccccc54)c(-c4nc(-c5ccccc5)cc(-c5ccccc5)n4)c3-c3ccccc3)nc(-c3ccccc3)n2)cc1]
172
-continued
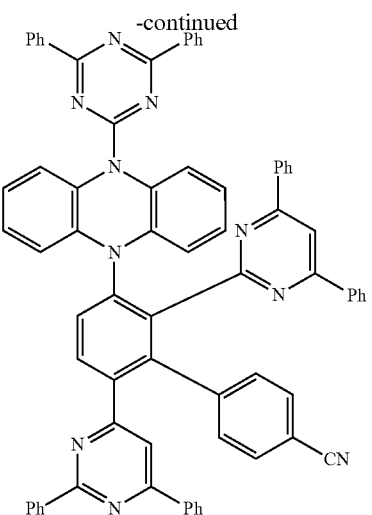
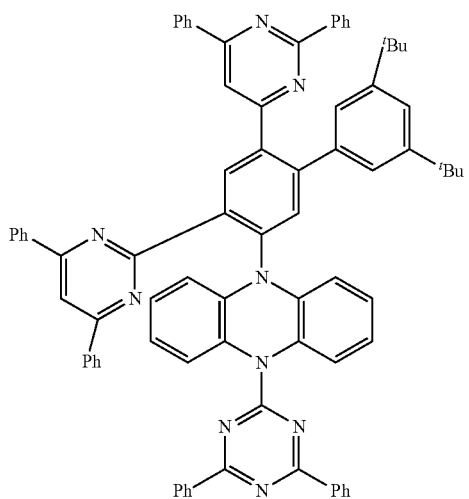
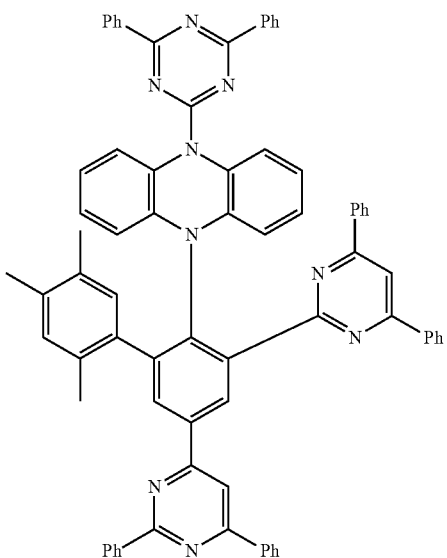

173
-continued
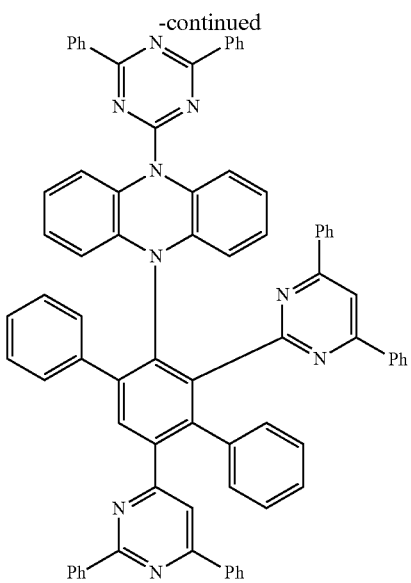
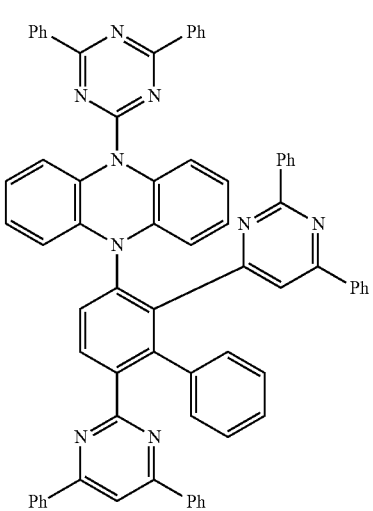
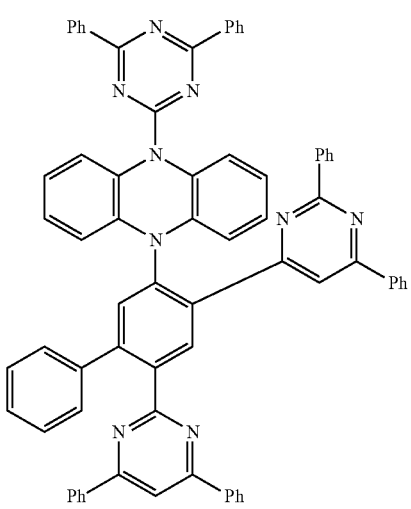
174
-continued
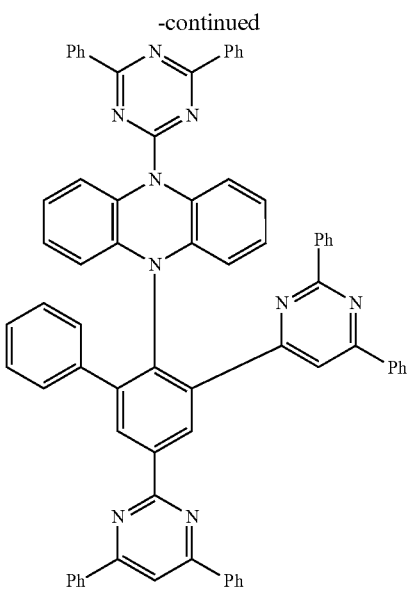
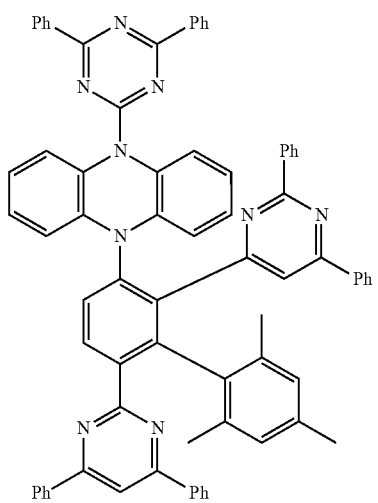
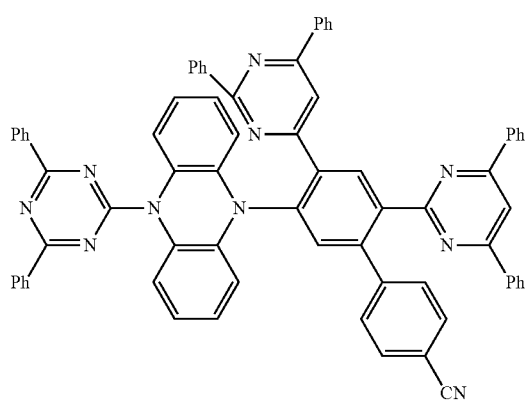

175
-continued
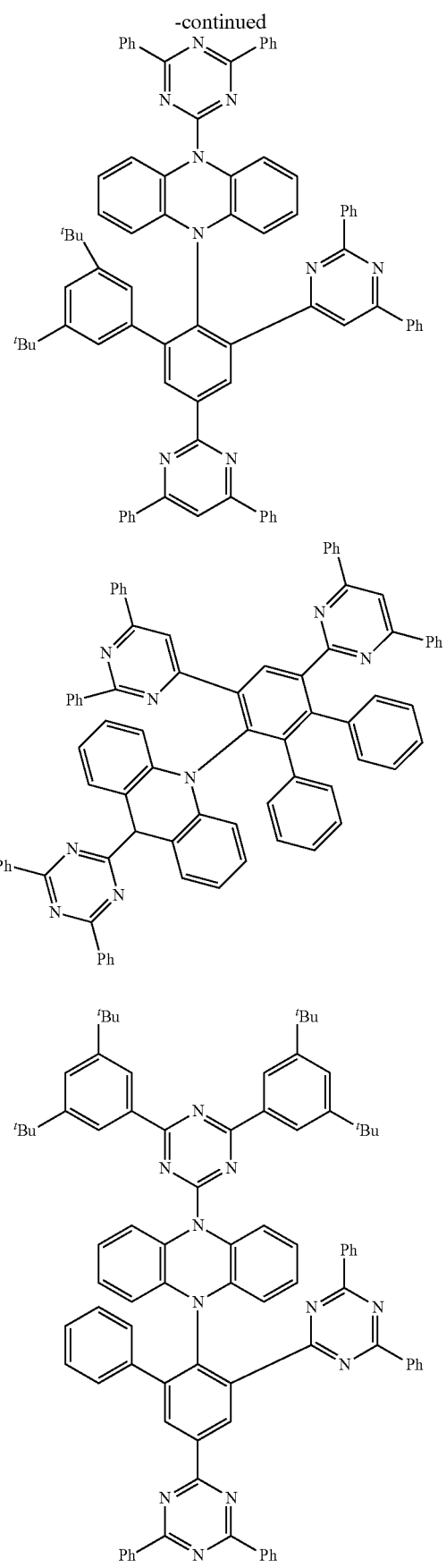
176
-continued
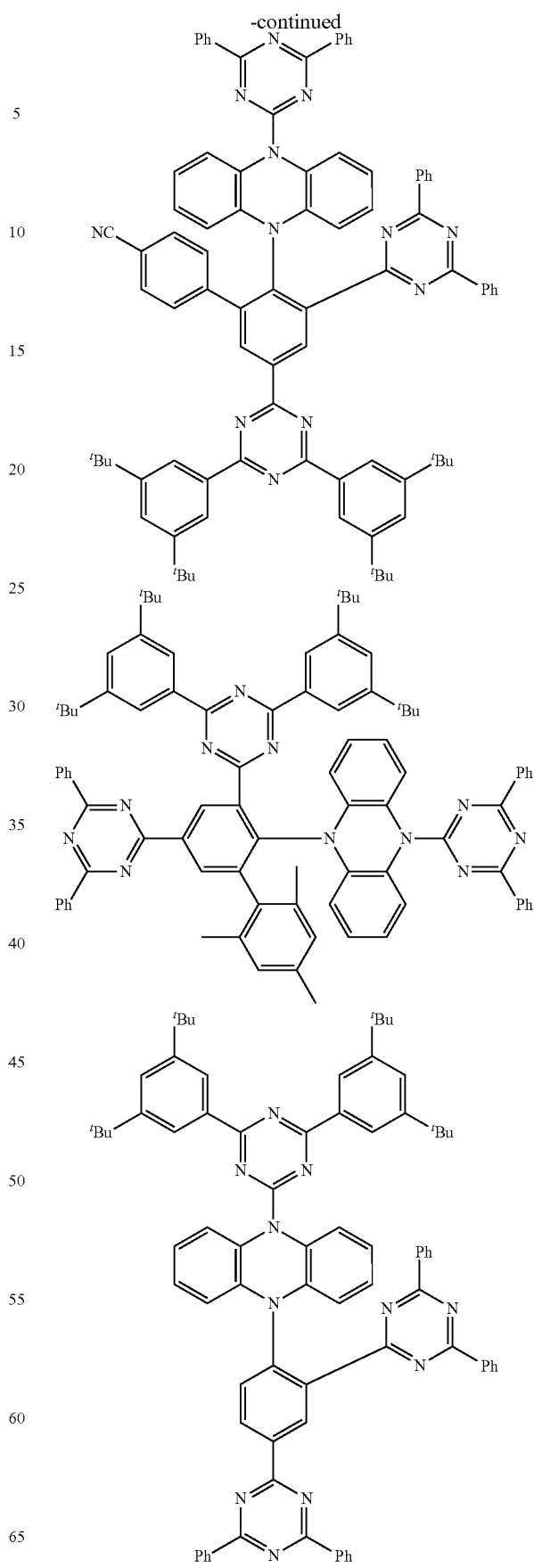

-continued

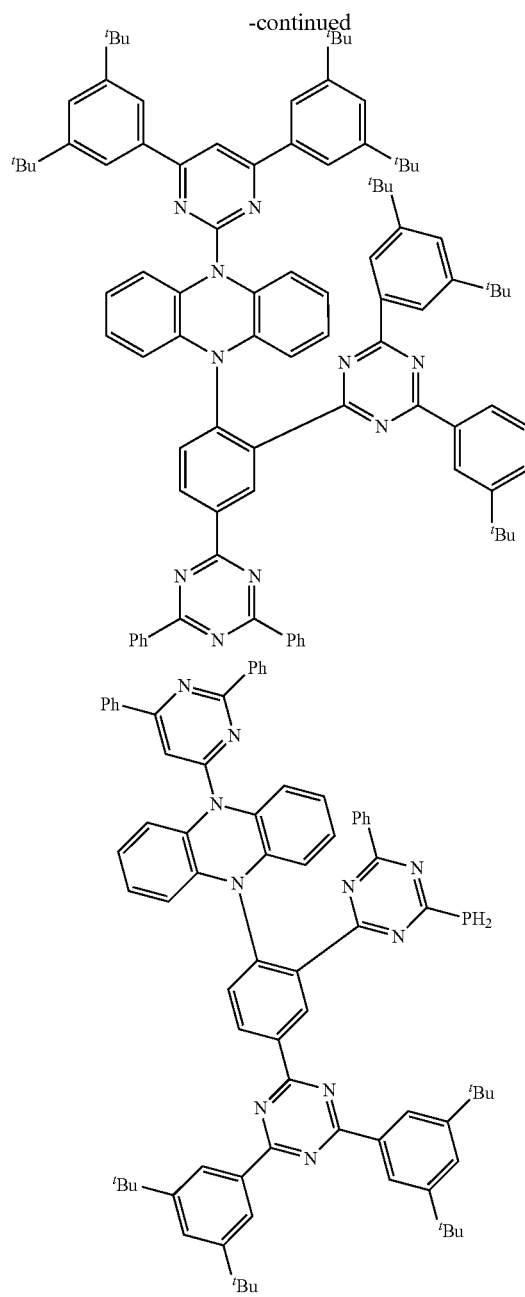

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An optoelectronic device comprising:
a substrate;
a first electrode;
a second electrode, wherein the first electrode or the second electrode is applied to the substrate; and
at least one light-emitting layer disposed between the first electrode and the second electrode and which comprises a compound of formula I:

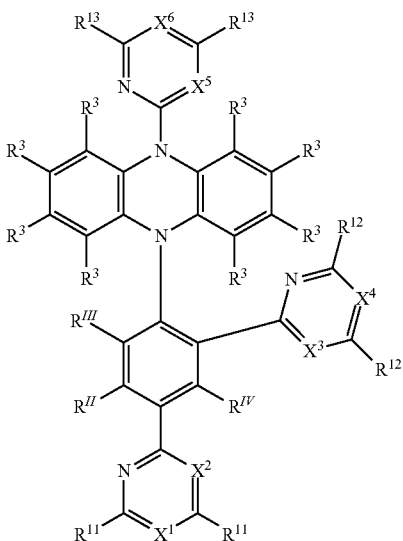

Formula I wherein
$X^1$ and $X^2$ are at each occurrence independently selected from the group consisting of $CR^{21}$ and N;
$X^3$ and $X^4$ are at each occurrence independently selected from the group consisting of $CR^{22}$ and N;
$X^5$ and $X^6$ are at each occurrence independently selected from the group consisting of $CR^{23}$ and N;
$R^{11}$ is at each occurrence independently selected from the group consisting of hydrogen, deuterium, $C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$;
$R^{12}$ is at each occurrence independently selected from the group consisting of hydrogen, deuterium, $C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$;
$R^{13}$ is at each occurrence independently selected from the group consisting of hydrogen, deuterium, $C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$;
$R^{21}$ is at each occurrence independently selected from the group consisting of hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$;
$R^{22}$ is at each occurrence independently selected from the group consisting of hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$;
$R^{23}$ is at each occurrence independently selected from the group consisting of hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl;
wherein one or more hydrogen atoms are optionally substituted by deuterium;
$C_6$-$C_{18}$-aryl,
which is optionally substituted with one or more substituents $R^6$; and
$C_3$-$C_{17}$-heteroaryl,
which is optionally substituted with one or more substituents $R^6$;
$R^{II}$, $R^{III}$ and $R^{IV}$ are independently selected from the group consisting of hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents $R^6$;
$R^a$ is at each occurrence independently selected from the group consisting of: hydrogen, deuterium, $N(R^5)_2$, $OR^5$, $Si(R^5)_3$, $B(OR^5)_2$, $OSO_2R^5$, $CF_3$, $CN$, F, Br, I,
$C_1$-$C_{40}$-alkyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-alkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $O=O$, $C=S$, $C=Se$, $C=NR^5$, $P(=O)(R^5)$, SO, $SO_2$, $NR^5$, O, S or $CONR^5$;
$C_1$-$C_{40}$-thioalkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkenyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkynyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_6$-$C_{60}$-aryl,
which is optionally substituted with one or more substituents $R^5$; and
$C_3$-$C_{57}$-heteroaryl, which is optionally substituted with one or more substituents $R^5$;
$R^5$ is at each occurrence independently selected from the group consisting of: hydrogen, deuterium, $N(R^6)_2$, $OR^6$, $Si(R^6)_3$, $B(OR^6)_2$, $OSO_2R^6$, $CF_3$, $CN$, F, Br,
$C_1$-$C_{40}$-alkyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $O=O$, $C=S$, $C=Se$, $C=NR^6$, $P(=O)(R^6)$, SO, $SO_2$, $NR^6$, O, S or $CONR^6$;

$C_1$-$C_{40}$-alkoxy,
which is optionally substituted with one or more substituents $R^6$ and
wherein one or more non-adjacent $CH_2$-groups are optionally substituted by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_1$-$C_{40}$-thioalkoxy,
which is optionally substituted with one or more substituents $R^6$ and
wherein one or more non-adjacent $CH_2$-groups are optionally substituted by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_2$-$C_{40}$-alkenyl,
which is optionally substituted with one or more substituents $R^6$ and
wherein one or more non-adjacent $CH_2$-groups are optionally substituted by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_2$-$C_{40}$-alkynyl,
which is optionally substituted with one or more substituents $R^6$ and
wherein one or more non-adjacent $CH_2$-groups are optionally substituted by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_6$-$C_{60}$-aryl,
which is optionally substituted with one or more substituents $R^6$; and
$C_3$-$C_{57}$-heteroaryl,
which is optionally substituted with one or more substituents $R^6$;
$R^6$ is at each occurrence independently selected from the group consisting of: hydrogen, deuterium, OPh, $CF_3$, CN, F,
$C_1$-$C_5$ alkyl,
wherein one or more hydrogen atoms are optionally, independently substituted by deuterium, CN, $CF_3$, or F;
$C_1$-$C_5$-alkoxy,
wherein one or more hydrogen atoms are optionally, independently substituted by deuterium, CN, $CF_2$, or F;
$C_1$-$C_5$-thioalkoxy,
wherein one or more hydrogen atoms are optionally, independently substituted by deuterium, CN, $CF_3$, or F;
$C_2$-$C_5$ alkenyl,
wherein one or more hydrogen atoms are optionally, independently substituted by deuterium, CN, $CF_3$, or F;
$C_2$-$C_5$-alkynyl,
wherein one or more hydrogen atoms are optionally, independently substituted by deuterium, CN, $CF_3$, or F:
$C_6$-$C_{18}$-aryl,
which is optionally substituted with one or more $C_1$-$C_5$-alkyl substituents;
$C_3$-$C_{17}$-heteroaryl,
which is optionally substituted with one or more $C_1$-$C_5$-alkyl substituents;
$N(C_6$-$C_{18}$-aryl$)_2$;
$N(C_3$-$C_{17}$-heteroaryl$)_2$, and
$N(C_3$-$C_{17}$-heteroaryl$)(C_6$-$C_{18}$-aryl);
wherein, optionally, the substituents $R^a$ or $R^5$ independently form a mono- or polycyclic, aliphatic, aromatic and/or benzo-fused ring system with one or more substituents $R^a$ or $R^5$;

wherein
at least one variable selected from the group consisting of $X^1$, $X^2$ is N;
at least one variable selected from the group consisting of $X^3$, $X^4$ is N; and
at least one variable selected from the group consisting of $X^5$, $X^6$ is N, and
wherein the compound of formula I has a $\Delta E_{ST}$ value of less than 5000 cm$^{-1}$, which corresponds to the energy difference between the first excited singlet state (S1) and the first excited triplet state (T1).

2. The optoelectronic device according to claim 1, wherein $R^{11}$, $R^{12}$, $R^{13}$, $R^{II}$, $R^{III}$ and $R^{IV}$ are at each occurrence independently selected from the group consisting of H, methyl and phenyl, which is optionally substituted with one or more substituents independently selected from the group consisting of Me, $^iPr$, $^tBu$, CN, $CF_3$, and Ph, and
$R^{21}$, $R^{22}$, $R^{23}$ are at each occurrence independently selected from the group consisting of H, methyl and phenyl, which is optionally substituted with one or more substituents independently selected from the group consisting of Me, $^iPr$, $^tBu$, CN, $CF_3$, and Ph, if only one of $X^1$ and $X^2$ is N, only one of $X^3$ and $X^4$ is N, and only one of $X^5$ and $X^6$ is N, respectively.

3. The optoelectronic device according to claim 1, wherein $X^1$, $X^2$, $X^3$, $X^4$, $X^5$ and $X^6$ are N at each occurrence.

4. The optoelectronic device according to claim 1, wherein
$R^{11}$, $R^{12}$, and $R^{13}$ are Ph at each occurrence, and
$R^{II}$, $R^{III}$, and $R^{IV}$ are H at each occurrence, and
one of $R^{21}$ is H, if only one of $X^1$ and $X^2$ is N, and
one of $R^{22}$ is H, if only one of $X^3$ and $X^4$ is N, and
one of $R^{23}$ is H, if only one of $X^5$ and $X^6$ is N.

5. The optoelectronic device according to claim 1, wherein $R^a$ is at each occurrence independently selected from the group consisting of hydrogen, Me, $^iPr$, $^tBu$, CN, $CF_3$, $SiMe_3$, $SiPh_3$, Ph, which is optionally substituted with one or more substituents independently selected from the group consisting of Me, $^iPr$, $^tBu$, CN, $CF_3$, and Ph,
pyridinyl, which is optionally substituted with one or more substituents independently selected from the group consisting of Me, $^iPr$, $^tBu$, CN, $CF_3$, and Ph,
pyrimidinyl, which is optionally substituted with one or more substituents independently selected from the group consisting of Me, $^iPr$, $^tBu$, CN, $CF_3$, and Ph,
carbazolyl, which is optionally substituted with one or more substituents independently selected from the group consisting of Me, $^iPr$, $^tBu$, CN, $CF_3$, and Ph,
triazinyl, which is optionally substituted with one or more substituents independently selected from the group consisting of Me, $^iPr$, $^tBu$, CN, $CF_3$, and Ph, and $N(Ph)_2$.

6. The optoelectronic device according to claim 1, wherein $R^a$ is at each occurrence independently selected from the group consisting of hydrogen, Me, $^iPr$, $^tBu$, CN, $CF_3$, $SiMe_3$, $SiPh_3$, Ph, which is optionally substituted with one or more substituents independently selected from the group consisting of Me, $^iPr$, $^tBu$, CN, $CF_3$, and Ph,
pyridinyl, which is optionally substituted with one or more substituents independently selected from the group consisting of Me, $^iPr$, $^tBu$, CN, $CF_2$, and Ph,
pyrimidinyl, which is optionally substituted with one or more substituents independently selected from the group consisting of Me, $^iPr$, $^tBu$, CN, $CF_3$, and Ph, and
triazinyl, which is optionally substituted with one or more substituents independently selected from the group consisting of Me, $^iPr$, $^tBu$, CN, $CF_3$, and Ph.

7. The optoelectronic device according to claim 1, wherein $R^a$ is at each occurrence independently selected from the group consisting of hydrogen, methyl, i-propyl (OH(CH$_3$)$_2$) ($^i$Pr), t-butyl, phenyl, CN, CF$_3$, and diphenylamine.

8. The optoelectronic device according to claim 1, the light-emitting layer further comprising one or more emitter and/or host materials different from the compound of formula 1.

9. The optoelectronic device according to claim 1, the light-emitting layer further comprising a host compound H.

10. The optoelectronic device according to claim 9,
wherein the host compound H has a highest occupied molecular orbital HOMO(H) having an energy $E^{HOMO}$(H) in the range of from −5 eV to −6.5 eV,
wherein the compound of formula I has a highest occupied molecular orbital HOMO(E) having an energy $E^{HOMO}$(E), and
wherein $E^{HOMO}$(H)>$E^{HOMO}$(E).

11. The optoelectronic device according to claim 9,
wherein the host compound H has a lowest unoccupied molecular orbital LUMO(H) having an energy $E^{LUMO}$(H),
wherein the compound of formula I has a lowest unoccupied molecular orbital LUMO(E) having an energy $E^{LUMO}$(E), and
wherein $E^{LUMO}$(H)>$E^{LUMO}$(E).

12. The optoelectronic device according to claim 1, the compound of formula I has an emission peak in the range of a wavelength of from 380 to 800 nm, wherein a full width at half maximum of the emission peak is less than 0.50 eV.

13. The optoelectronic device according to claim 1, the light-emitting layer further comprising an emitter compound F.

14. The optoelectronic device according to claim 13, the emitter compound F is a TADF emitter.

15. The optoelectronic device according to claim 13, the emitter compound F is a fluorescent and/or phosphorescent emitter.

16. The optoelectronic device according to claim 1, further comprising two or more emission layers between the first electrode and the second electrode.

17. The optoelectronic device according to claim 16, further comprising at least one of a charge generation layer, a blocking layer, or a transporting layer between the emission layers.

18. The optoelectronic device according to claim 1, wherein the optoelectronic device is an organic light-emitting diode, light-emitting electrochemical cell, organic light-emitting sensor, an organic diode, an organic solar cell, an organic transistor, an organic field-effect transistor, an organic laser or a down-conversion element.

* * * * *